(12) United States Patent
Van Deynze et al.

(10) Patent No.: US 11,744,220 B2
(45) Date of Patent: Sep. 5, 2023

(54) PEPPER PLANTS BEARING FRUIT HAVING A LOW DESTEMMING FORCE

(71) Applicant: The Regents of the University of California, Oakland, CA (US)

(72) Inventors: Allen E. Van Deynze, Davis, CA (US); Theresa A. Hill, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/042,467

(22) PCT Filed: Mar. 29, 2019

(86) PCT No.: PCT/US2019/024986
§ 371 (c)(1),
(2) Date: Sep. 28, 2020

(87) PCT Pub. No.: WO2019/191675
PCT Pub. Date: Oct. 3, 2019

(65) Prior Publication Data
US 2021/0015069 A1    Jan. 21, 2021

Related U.S. Application Data

(60) Provisional application No. 62/650,203, filed on Mar. 29, 2018.

(51) Int. Cl.
*A01H 5/08*    (2018.01)
*A01H 6/82*    (2018.01)
*A01H 1/04*    (2006.01)

(52) U.S. Cl.
CPC ............... *A01H 6/822* (2018.05); *A01H 1/04* (2013.01); *A01H 5/08* (2013.01)

(58) Field of Classification Search
None
See application file for complete search history.

(56) References Cited

FOREIGN PATENT DOCUMENTS

| JP | 2017/147975 A | 8/2017 |
| WO | 2014/145514 A1 | 9/2014 |
| WO | WO 2014/145514 A1 * | 9/2014 |

OTHER PUBLICATIONS

Spencer, R.D., 1999. Cultivated plants and the codes of nomenclature—towards the resolution of a demarcation dispute. In: S. Andrews, A.C. Leslie and C. Alexander (Editors), Taxonomy of Cultivated Plants: Third International Symposium, pp. 171-181, Royal Botanic Gardens, Kew.*
Ben-Chaim A. and Paran I., 2000, Genetic Analysis of Quantitative Traits in Pepper (*Capsicum annuum*), J. Amer. Soc. Hort. Sci. 125: 66-70.*
Van Deynze, Proposal Van Deynze Pepper Commission 2015, California Pepper Commission, 2014-2015, available at https://www.calpeppers.com/page.php?s=10&c=64, accessed Nov. 3, 2021.*
University of California Davis Office of Research, Pepper Plant with Abscising Fruit and Petiole for Easy Harvest, Tech ID: 31886/UC Case 2015-633-0 (inventors: Hill, Theresa A.; Van Deynze, Allen E.), 2015, available at https://techtransfer.universityofcalifornia.edu/NCD/31886.html, accessed Novembers, 2021.*
Chabaane et al., 2021, Domestication of Chili Pepper Has Altered Fruit Traits Affecting the Oviposition and Feeding Behavior of the Pepper Weevil, Insects 12, 630, pp. 1-17.*
Bernacchi et al. Theor Appl Genet (1998) 97:381-397.*
Gersch et al. J. Amer. Soc. Hort. Sci 123(4):550-555 (1998).*
International Search Report and Written Opinion from PCT/US2019/024986 dated Jun. 5, 2019; 28 pages.
Setiamihardja, R. et al.; "Association of Pedicel Length and Ease of Fruit Length and Diameter and Ease of Fruit Detachment in Pepper"; *Journal of the American Society for Horticultural Science*: vol. 115, No. 4; Jul. 1, 1990; pp. 677-681.
Werner, D.J. et al.; "Inheritance of Fruit Detachment Force in Pepper"; *Journal of the American Society for Horticultural Science*: vol. 105, No. 6; 1980; pp. 805-807.
Walker, S. et al.; "'NuMex Garnet' Paprika"; *Hortscience*; vol. 39, No. 3; Jun. 1, 2004; pp. 629-630.
Gubert, C.M. et al.; "HAESA and HAESA-LIKE2 activate organ abscission downstream of Nevershed and Evershed in *Arabidopsis* flowers"; *Plant Signaling and Behavior*: vol. 9, No. 7; 2014; pp. e29115.
Arpaci, B.B. et al.; "Interspecific (*Capsicum chacoense* Hunz. and *Capsicum annuum* L.) Inheritance of Fruit Detachment Force Trait in Hot Pepper"; *Scientific Papers, Series B, Horticulture*: vol. LXII; Jun. 1, 2018; pp. 391-394.
Ben-Chaim A. et al.; Genetic Analysis of Quantitative Traits in Pepper (*Capsicum annuum*); *J. Amer. Soc. Hort. Sci.*; vol. 125, No. 1; 2000; pp. 66-70.
Chaim, A.B. et al.; QTL mapping of fruit-related traits in pepper (*Capsicum annuum*); *Theor. Appl. Genet.*: vol. 102; 2001; pp. 1016-1028.
Naegele, R.P. et al.; "Genetic Diversity, Population Structure, and Heritabaility of Fruit Traits in *Capsicum annuum*"; *PLOS One*; Jul. 14, 2016; 17 pages.

* cited by examiner

*Primary Examiner* — Medina A Ibrahim
(74) *Attorney, Agent, or Firm* — Kilpatrick Townsend and Stockton LLP

(57) ABSTRACT

The present invention provides methods of preparing a cultivated pepper plant bearing fruit having a low destemming force, as well as methods of preparing a cultivated pepper plant bearing clustered fruit. The invention also provides cultivated pepper plants prepared by these methods.

3 Claims, 7 Drawing Sheets
Specification includes a Sequence Listing.

CA. 10X.CHR2_143240262

ANALYSIS OF VARIANCE

| SOURCE | DF | SUM OF SQUARES | MEAN SQUARE | F RATIO | PROB > F |
|---|---|---|---|---|---|
| CA.10X.CHR2_143240262 | 2 | 147.1425 | 73.5713 | 8.7339 | 0.0003* |
| ERROR | 129 | 1086.6533 | 8.4237 | | |
| C.TOTAL | 131 | 1233.7959 | | | |

MEANS FOR ONEWAY ANOVA

| LEVEL | NUMBER | MEAN | STD ERROR | LOWER 95% | UPPER 95% |
|---|---|---|---|---|---|
| C | 27 | 27.5458 | 0.55856 | 26.438 | 28.648 |
| T | 31 | 30.2176 | 0.52128 | 29.186 | 31.249 |
| Y | 74 | 30.1344 | 0.33739 | 29.467 | 30.802 |

STD ERROR USES A POOLED ESTIMATE OF ERROR VARIANCE

FIG. 5A

| ANALYSIS OF VARIANCE | | | | | |
|---|---|---|---|---|---|
| SOURCE | DF | SUM OF SQUARES | MEAN SQUARE | F RATIO | PROB > F |
| CA.10X.CHR10_172967183 | 2 | 0.4976712 | 0.248836 | 12.4276 | <.0001* |
| ERROR | 127 | 2.5428971 | 0.020023 | | |
| C.TOTAL | 129 | 3.0405683 | | | |

| MEANS OF ONEWAY ANOVA | | | | | |
|---|---|---|---|---|---|
| LEVEL | NUMBER | MEAN | STD ERROR | LOWER 95% | UPPER 95% |
| C | 32 | 0.629853 | 0.02501 | 0.58035 | 0.67935 |
| T | 28 | 0.450114 | 0.02674 | 0.39720 | 0.50303 |
| Y | 70 | 0.524257 | 0.01691 | 0.49079 | 0.55772 |

STD ERROR USES A POOLED ESTIMATE OF ERROR VARIANCE

FIG. 6A

| | | FORCE | | | | | FORCE | | FORCE | FREQUENCY | |
|---|---|---|---|---|---|---|---|---|---|---|---|
| | MARKER POS (BP) | CHR2 142,933,906 | CHR2 143,240,262 | CHR2 143,710,406 | CHR2 148,097,513 | CHR3 245,138,565 | CHR3 245,358,487 | CHR3 246,172,201 | CHR7 213,622,437 | CHR10 164,006,069 | CHR10 172,967,183 |
| FAVORABLE ALLELE | | A | C | A | G | G | T | G | A | T | C |
| FREQUENCY FORCE (N) | | | | | | | | | | | |
| UCD-14 | 69% 19.1 | A | C | A | G | G | T | G | G | T | C |
| MAOR | 0% NA | C | T | G | A | A | C | A | A | C | T |
| MUC14-200 | 50% 22.9 | C | T | G | A | G | T | G | A | T | C |
| MUC14-297 | 54% 23.0 | A | C | A | G | A | C | A | G | T | C |
| MUC14-228 | 58% 26.9 | A | T | G | G | R | Y | R | R | T | C |
| MUC14-37 | 71% 28.0 | C | T | G | A | G | T | G | A | T | Y |
| MUC14-17 | 82% 30.0 | C | T | G | A | G | T | G | A | T | C |
| MUC14-30 | 87% 32.9 | C | T | G | A | G | T | G | A | T | C |
| MUC14-330 | 79% 35.5 | C | T | G | A | A | C | A | A | C | T |

FIG. 6B

| | | FORCE | | | | | FORCE | | FORCE | FREQUENCY | |
|---|---|---|---|---|---|---|---|---|---|---|---|
| | MARKER POS (BP) | CHR2 142,933,906 | CHR2 143,240,262 | CHR2 143,710,406 | CHR2 148,097,513 | CHR3 245,138,565 | CHR3 245,358,487 | CHR3 246,172,201 | CHR7 213,622,437 | CHR10 164,006,069 | CHR10 172,967,183 |
| FAVORABLE ALLELE | | A | C | A | G | G | T | G | A | T | C |
| FREQUENCY FORCE (N) | | | | | | | | | | | |
| UCD-14 | 69% 19.1 | A | C | A | G | G | T | G | G | T | C |
| MAOR | 0% NA | C | T | G | A | A | C | A | A | C | T |
| MUC14-200 | 50% 22.9 | C | T | G | A | G | T | G | A | T | C |
| MUC14-228 | 58% 26.9 | A | T | G | G | R | Y | R | R | T | C |
| MUC14-297 | 54% 23.0 | A | C | A | G | A | C | A | G | T | C |

SEQUENCE LISTING

```
<160> NUMBER OF SEQ ID NOS: 13

<210> SEQ ID NO 1
<211> LENGTH: 101
<212> TYPE: DNA
<213> ORGANISM: Capsicum sp.

<400> SEQUENCE: 1
tccaaacttt caatttatca ttcacaaccc ccagcgtctc atcaatcaaa cctacatcat      60
ccggaaatag catataccaa ggatcttttc cttgaatacg c                        101

<210> SEQ ID NO 2
<211> LENGTH: 101
<212> TYPE: DNA
<213> ORGANISM: Capsicum sp.

<400> SEQUENCE: 2
aaaaaactta ttgagaatga aagagactct caaacatgag gaagtaagaa ttttgtatag      60
ggctacagtg gatacatact agaagaggca tatcatggct a                        101

<210> SEQ ID NO 3
<211> LENGTH: 101
<212> TYPE: DNA
<213> ORGANISM: Capsicum sp.

<400> SEQUENCE: 3
tgcttctgat caacctacag cattagtgta accaacaaca gcaactgtac gaatttcttg      60
accatctgtt cctccatgcc tcttacgagc agcacgctgc a                        101

<210> SEQ ID NO 4
<211> LENGTH: 101
<212> TYPE: DNA
<213> ORGANISM: Capsicum sp.

<400> SEQUENCE: 4
aaacttattt actgatccac tggacggtat ctagtaagac ttagactttc atcattcaaa      60
accttagttt caaactgatg tgtgctttca actttcctat t                        101

<210> SEQ ID NO 5
<211> LENGTH: 101
<212> TYPE: DNA
<213> ORGANISM: Capsicum sp.

<400> SEQUENCE: 5
gatgcaattt cacagacacc ctgggaccat gaaccgtgct ttgataccaa atttgtcacg      60
acccaaattg gggccctagc cgtgacgagc attctcgaac t                        101

<210> SEQ ID NO 6
<211> LENGTH: 101
<212> TYPE: DNA
<213> ORGANISM: Capsicum sp.

<400> SEQUENCE: 6
```

```
ttccaaaagt tgtaagactt accctacttc aggtgtcgtt ttggcctcat actgtccttt    60
ctttctaacc ctatccaaaa ttcaagttac aaccaaagaa a                       101

<210> SEQ ID NO 7
<211> LENGTH: 101
<212> TYPE: DNA
<213> ORGANISM: Capsicum sp.

<400> SEQUENCE: 7
gagcagactg tataatcaat attaacacaa atgcagaatc agagagtaga ctgtaatatt    60
aacacaaata cacagacaga gagcagactg taatattaac a                       101

<210> SEQ ID NO 8
<211> LENGTH: 101
<212> TYPE: DNA
<213> ORGANISM: Capsicum sp.

<400> SEQUENCE: 8
atcggaattg accttaacag tattgagtct gttgttacac aaacagctgg atattataat    60
gggagtgatt cttttgtccc tttgaatatg cgtactgggc a                       101

<210> SEQ ID NO 9
<211> LENGTH: 101
<212> TYPE: DNA
<213> ORGANISM: Capsicum sp.

<400> SEQUENCE: 9
ataaagtttt ggcccagact actgtgcccc acacactcta gaattacttt cttgcatagt    60
ttgaacagac tcatctgtgc ccaaacaacg taagagtact c                       101

<210> SEQ ID NO 10
<211> LENGTH: 101
<212> TYPE: DNA
<213> ORGANISM: Capsicum sp.

<400> SEQUENCE: 10
tttatgttct atgtaattgt acaaaatggt tacaggtaga ggagaaaatt taatgaatca    60
ttctattggt aggaaaagaa gtgaaaaagg taaagagat g                        101

<210> SEQ ID NO 11
<211> LENGTH: 101
<212> TYPE: DNA
<213> ORGANISM: Capsicum sp.

<400> SEQUENCE: 11
cacaaaaaac tgctatagct tgaataatca gattgagtcc ctaataatga ggggtataat    60
caaattcacc accatagctc caaatatgaa caataatgcc t                       101

<210> SEQ ID NO 12
<211> LENGTH: 101
<212> TYPE: DNA
<213> ORGANISM: Capsicum sp.

<400> SEQUENCE: 12
atcatcacaa cttataaaat catggatgct aaatgtaaat gactcacata ggcttgagaa    60
gtccttaaac tgaatatcat aaatcatgat taatatagca t                       101

<210> SEQ ID NO 13
```

-continued

```
<211> LENGTH: 101
<212> TYPE: DNA
<213> ORGANISM: Capsicum sp.

<400> SEQUENCE: 13
catgataaaa aatctacgta atgcagtttg tctgactccc tgggactcta aaaaaaactt      60
aggctctgat accaagtttg taacgccctg aaacttggtc t                        101
```

PEPPER PLANTS BEARING FRUIT HAVING A LOW DESTEMMING FORCE

CROSS-REFERENCES TO RELATED APPLICATIONS

The present application is a US National Phase Application Under Section 371 of PCT/US2019/024986, filed Mar. 29, 2019, which claims benefit of priority to U.S. Provisional Patent Application No. 62/650,203, filed Mar. 29, 2018, which are incorporated by reference for all purposes.

SEQUENCE LISTING

The instant application contains a Sequence Listing which has been submitted electronically in ASCII format and is hereby incorporated by reference in its entirety. Said ASCII copy, created on Sep. 18, 2020, is named 081906-1210428-228220US_SL.txt and is 3,163 bytes in size.

BACKGROUND OF THE INVENTION

Cultivated *Capsicum* spp., including *C. annuum*, *C. frutescens*, *C. chinense*, *C. buccatum* and *C. pubescens*, are grown for vegetable, spice, ornamental, medicinal and lachrymator uses and are a rich source of vitamins A, B and C and consumed to improve diets around the world. They are also high in iron, potassium and magnesium. Chile peppers comprise 18% of the $898.6M (US farm value, 30% by area). By value, California produces 54% of bells and Florida 29%. For chile production, 61% is in CA and 31% in NM with the rest in TX and AZ (12). The per acre production costs for bell peppers are $13,235 for fresh market and $6,650 for processing. Harvesting costs account for 20-50% of the total production costs for both fresh and processing bell pepper production in CA (10,11). Hand-harvest labor accounts for approximately 50-60% of overall production costs for New Mexico type green chile. Estimated costs are similar to bells and can be even greater in smaller-fruited specialty peppers such as jalapeños. In addition, peppers destined for processing, as opposed to fresh market, have a lower dollar return to growers. Stakeholders (seed industry, growers) have identified jalapeños, bells and green chiles (New Mexico type) as a main market for pickling, sauce and salsa. The majority of bell and chile pepper varieties grown in California are hybrids with an upright growth habit that may require multiple manual harvests. In New Mexico and other states, open-pollinated varieties and hybrids are grown.

Mechanical harvesting of peppers has been attempted since the 1960's by adapting tomato harvesters. Germplasm development has resulted in peppers that detach well from the stem while leaving the pedicel on the fruit. Efforts have been made to optimize fruit detachment for mechanical harvesters by several breeding programs. For example, advancements have been made in varieties such as NuMex Garnet, which was bred specifically for mechanical harvesting. However, other specialty peppers such as New Mexico type green chiles, continue to be completely hand-harvested. This has resulted in the continued loss of green chile acreage from the US to countries with much lower labor costs. Destemming, along with fruit damage, are intransigent challenges that have prevented mechanical harvest adoption in NM type green chile. Green chiles and bell types pose particular challenges to mechanization, as more force is needed to detach the pedicel from the stem than ripe (red) fruits. Additionally, the calyx/receptacle and stem must be removed from the fruit (destemming or decapping) for processing. Removal of the calyx/receptacle and stem from the fruit is critical for processing. This extraneous material presents quality and safety issue in processed peppers. For example, compared to red fruit used for drying, bruising of green fruit is not tolerated in the market.

Additional requirements for mechanical harvesting include fruit clustering, determinacy, a more erect plant architecture, reduced basal branching and uniformity of maturity as well as specific fruit placement. Even though significant research has been done in testing pepper varieties and harvesters that optimize detachment of fruit from the stem, an additional destemming step post-harvest is still necessary. The present invention addresses these and other needs.

BRIEF SUMMARY OF THE INVENTION

The present invention provides methods of preparing a cultivated pepper plant bearing fruit having a low destemming force. The method comprise crossing a first parent pepper plant with a second parent pepper plant bearing fruit with a low destemming force; and selecting progeny plants bearing fruit having a lower destemming force as compared to fruit from the first parent pepper plant. The second parent pepper plant may be UCD-14. The step of selecting the progeny plants may be carried out by measuring destemming force using a straight pull with a force gauge, a torque watch gauge, or by selecting a plant having a favorable allele identified in Table 1. The invention also provides cultivated pepper plants made by the method of the invention.

In some embodiments, the step of selecting includes selecting a plant having a favorable allele identified in Table 1 or Table 4.

In some embodiments, the second parent pepper plant has one or more (e.g., all) favorable allele identified in Table 1 or Table 4.

In some embodiments, the second parent pepper and/or the progeny is heterozygous or homozygous for an allele of UCD-14 from a region of chromosome 2 and 4; or 2 and 10; or 2 and 4 and 10; or 3 and 10; or 2 and 3 and 4 and 10, wherein the region is as defined in Table 3A.

In some embodiments, the second parent pepper and/or the progeny is heterozygous or homozygous for an allele of Maor from a region of chromosome 7, wherein the region is as defined in Table 3A. In some embodiments, the second parent pepper and/or the progeny is heterozygous or homozygous for an allele of Maor from a region of chromosome 7, wherein the region is as defined in Table 3A. In some embodiments, the second parent pepper and/or the progeny is heterozygous or homozygous for an allele of UCD-14 for any 1, 2, or 3 genes of: HSL2, EVR, or CST.

Also provided is a cultivated pepper plant having one or more (e.g., all) favorable allele identified in Table 1 or 4. In some embodiments, the pepper is heterozygous or homozygous for an allele of UCD-14 from a region of chromosome 2 and 4; or 2 and 10; or 2 and 4 and 10; or 3 and 10; or 2 and 3 and 4 and 10, wherein the region is as defined in Table 3A. In some embodiments, the pepper is further heterozygous or homozygous for an allele of Maor from a region of chromosome 7, wherein the region is as defined in Table 3A.

In some embodiments, the pepper is heterozygous or homozygous for an allele of Maor from a region of chromosome 7, wherein the region is as defined in Table 3A.

In some embodiments, the pepper is heterozygous or homozygous for an allele of UCD-14 for any 1, 2, or 3 genes of: HSL2, EVR, or CST.

Also provided is a method of harvesting peppers. In some embodiments, the method comprises removing pepper fruit from one or more cultivated pepper as described above or elsewhere herein. In some embodiments, the peppers are removed by shaking (e.g., mechanical shaking) the pepper plant.

The term, "detachment" and related terms refer to the separation of pedicel from the stem.

The term "destemming" and related terms refer to the separation of the fruit from the pedicel, receptacle and calyx. A fruit having a "low destemming force" is one in which the force required to separate the fruit from the receptacle and calyx in a healthy plant is equal to the force required to separate the fruit in UCD14, plus one standard deviation. This force will typically be less than about 40 Newton (N), usually less than about 30 N, and more often less than about 20 N using a straight pull with a force gauge, as described below. Alternatively, a fruit having a "low destemming force" can be identified as one in which the force required to separate the fruit from the receptacle and calyx in a healthy plant is less than about 55 N, usually less than about 45 N, and more often less than about 35 N using a torque watch gauge, as described below. A fruit having a "high destemming force" is one in which the force required to separate the fruit from the receptacle and calyx in a healthy plant is greater than about 40 N, usually greater than about 30 N, more often greater than about 20 N using the straight pull assay or greater than about 55 N, usually greater than about 45 N, and more often greater than about 35 N, using the torque watch assay.

Destemming "frequency" is the fraction of fruits where the calyx is completely removed from the fruit without tearing through the pericarp by a torque assay using the thumb or torque watch fitted with a fork.

A plant bearing "clustered fruit" is one bearing more than one, usually 3 or more, fruit per node.

BRIEF DESCRIPTION OF THE DRAWINGS

FIGS. 5A and 5B show diamond plots based on oneway ANOVA for destemming force (A) and destemming rate (B) by SNP allele for SNP markers on chromosome 2 and 10, respectively. This analysis is based on the data shown in FIG. 4 and SNPs found in Table 1.

FIG. 6 shows the genotype of various top progeny having reduced destemming force.

DETAILED DESCRIPTION OF THE INVENTION

Figure 1:
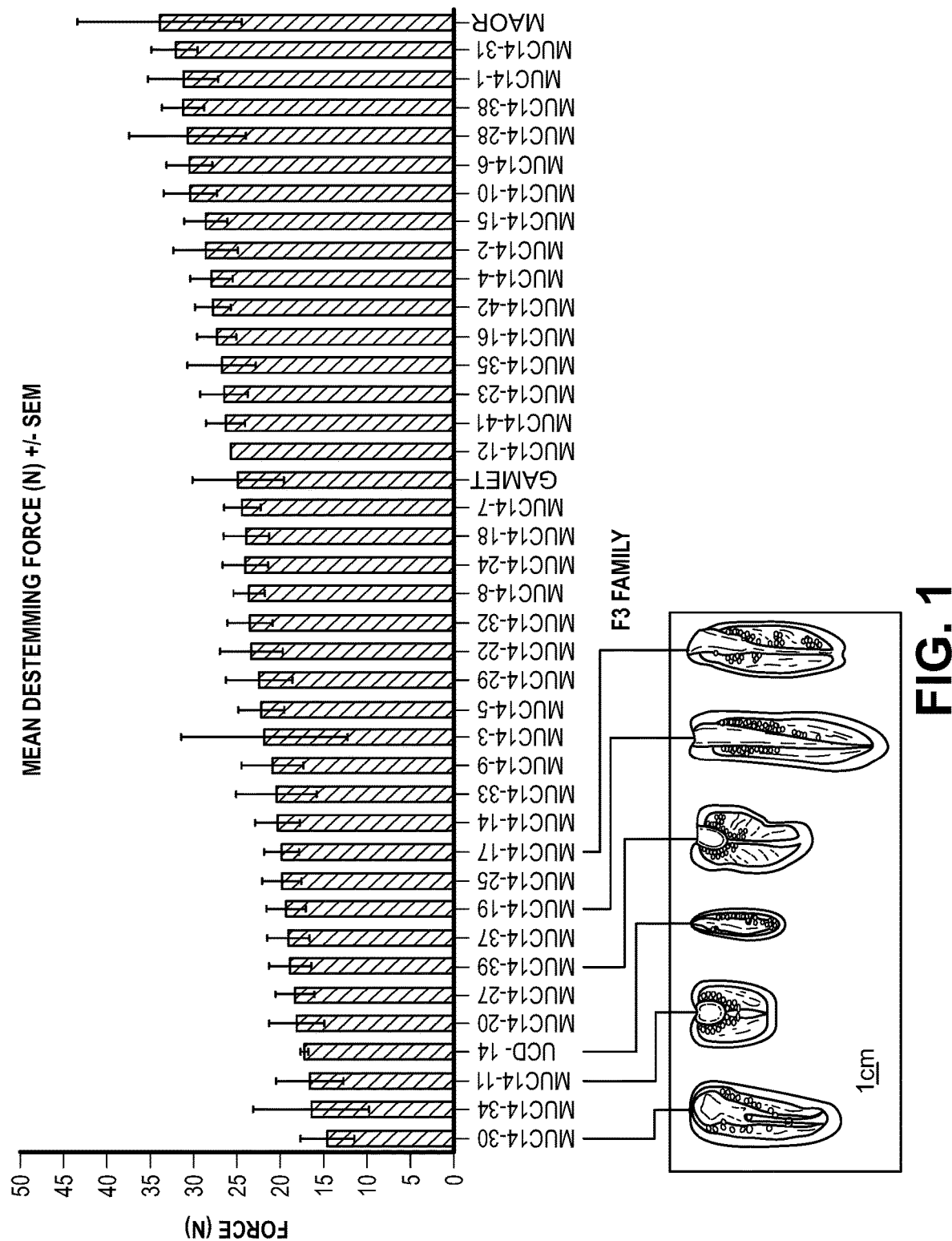
FIG. 1 shows mean destemming force among Maor x UCD-14 (MUC-14) F3 families. Scans of representative fruits for families having low destemming force shown below demonstrating variation in fruit size and shape among lines with low destemming force.

Successful mechanical harvesting requires a systems approach to combine harvesting technologies with varieties that can tolerate the process and maintain yield and quality. Several traits are essential, including erect stems, uniform ripening and fruit distribution, a thick pericarp tolerant of bruising and breakage combined with destemming of the fruit for processing (13).

The processing tomato industry was revolutionized by the combination of genetic self-pruning, a determinate trait conferred by a mutation in the SELF PRUNING gene, and the JOINTLESS gene which plays a role in the formation of the pedicel abscission zone and regulates the separation of the calyx from the fruit (destemming) in tomato. Although mutation in pepper fasciculate (fa), ortholog of the tomato SELF PRUNING gene, gives a similar determinate flowering phenotype in pepper, the JOINTLESS gene does not result in abscission of fruit in pepper. The fa mutation, commonly found in ornamental peppers, confers significantly reduced secondary internode length and vestigial leaves resulting in a phenotype with multiple fruit clustering and determination of flowering branches, i.e. a uniform ripening determinate phenotype that is early maturing.

The proposed S locus in pepper confers deciduous red ripe fruit, thus easy removal of the pedicel during picking, but a pleiotropic or tightly linked effect, the undesirable softening of the pericarp, has precluded its use. Wild peppers often have the S locus traits. We have recently identified a unique line conferring significantly lower destemming force at the receptacle, leaving a clean fruit without calyx that also has a moderately thick, firm pericarp. This trait is being transferred into jalapeños, New Mexico and bell types combining firm pericarps and green fruit destemming, unlike the S locus.

Destemming force varies between pepper species. In addition, in some species, the destemming force varies with fruit location within the canopy (6). Some researchers have found that fruit destemming force is correlated with fruit size and mass (1;8). Miles et al (9) conducted a study of the physical properties of the chile plant that indicated that red fruit could be best removed by inducing bending stresses in the stems causing a failure at the abscission point. When applied force placed the stem in tension, the mean force to remove the fruit was 21 Newton (N). In contrast, when they induced bending stresses in the stem, most fruit were removed when the applied forces were less than 4 N, a five-fold decrease. An engineering analysis of the internal stresses in a biological tissue will show that during bending, one side of the pedicel is exposed to tensile stresses while the opposite side exposed to compressive stresses. This condition causes the internal shear stress between cells inside the pedicel to be maximized. Under the condition where the ultimate shear strength of the tissue is below the ultimate tensile strength, the tissue will fail in shear before it will fail in tension. The experimental results by Miles et al., showing a five-fold decrease in pepper removal force when bending the stem, would suggest that this is the case in chile pepper. Research by Chen and Sun (2) has shown, however, that the loading rate, will affect the stress at failure in viscoelastic materials, like biological tissue, and nearly all published studies on destemming force levels have been done at slow loading rates, below the rates applied in mechanical harvesters.

Production of Plants

Pepper plants bearing clustered fruit and/or fruit with a low destemming force can be produced using breeding methods well known to those of skill in the art. For example, desired plants can be produced by crossing a first parent pepper plant (e.g., a cultivated pepper) bearing fruit having a high mean destemming force with a second parent plant bearing fruit having a low mean destemming force. Progeny bearing fruit with a mean destemming force lower than that of the first parent are selected. Pepper plants bearing clustered fruit can be produced by crossing a first parent pepper plant bearing one fruit per node with a second parent plant bearing clustered fruit. Progeny bearing more than one fruit per node are selected.

Introgression of a locus conferring either the clustered fruit phenotype or the low destemming force phenotype into a pepper cultivar lacking such a locus can be used to improve mechanical harvesting of fruit from the cultivar. Any related species (for example in the genus *Capsicum*) bearing clustered fruit or fruit having a low mean destemming force can be used to introgress the loci into the pepper cultivar.

Chromosome coordinates of the low destemming force loci in pepper have been determined. They are presented in Table 1 and Table 3. Accordingly, peppers with low destemming force include (e.g., are heterozygous for or homozygous for) those that include one or more (e.g., 1, 2, 3, 4, 5, 6, 7, 8, 9, 10 or more) favorable alleles as shown in Table 1 or Table 3 or Table 5. In some embodiments, the pepper with low destemming force has (e.g., are heterozygous for or homozygous for) at least one favorable allele in at least 1, 2, 3, 4, 5 of the following regions: chromosome 2, 3, 4, 7, or 10 in the regions shown in Table 3A. It will be appreciated that in many cases, because different polymorphic markers within a particular chromosomal region, the presence of one favorable marker in a particular region or locus will indicate a high likelihood of other favorable alleles in the same region or locus unless a rare recombination event has occurred. As can be seen from Table 5, peppers with desirable low destemming force include those as follows: Having (e.g., are heterozygous for or homozygous for) at least one or more favorable allele(s) at the regions defined in 1, 2, 3, 4 or all 5 of the regions defined in Table 3A for chromosomes 2, 3, 4, 7, and 10. For example, in some embodiments, the pepper has (e.g., are heterozygous for or homozygous for) an allele of UCD-14 from chromosome 2 and 4; or 2 and 10; or 2 and 4 and 10; or 3 and 10; or 2 and 3 and 4 and 10, wherein the region is as defined in Table 3A. In some embodiments, any of the previous combinations are combined with a Maor allele (e.g., heterozygous or homozygous) from the region defined in chromosome 7. All of the regions are defined relative to the pepper genome in Table 3. SNPs for measuring the presence or absence of alleles in this region can be found in Table 1 and 4. Exemplary sequences surrounding the SNPs of Table 1 are shown in Table 2.

Any number of standard breeding schemes can be used to introgress the desired locus into a pepper cultivar. The particular scheme used is not critical to the invention, so long as the locus is stably incorporated into the genome of the cultivar.

Desired plants can be screened by detecting fruit clusters and/or determining destemming force for fruit on progeny of the cross, as discussed in more detail below.

Alternatively, marker genes which are tightly linked with the phenotype can be used to identify the desired plants.

Exemplary types of applicable pepper plants include but are not limited to chile (including but not limited to green chiles) and green blocky peppers. The methods described herein are of particular use for pepper varieties that are harvested while not completely ripe.

EXAMPLES

We have screened a set of wild and semi-domesticated pepper accessions recently collected in regions of Mexico for disease resistance and horticultural traits. Among these is a semi-domesticated *C. annuum* accession, UCD-14, that has oblong fruit with firm texture and medium pericarp thickness that easily abscises when picked at the mature green stage, leaving the pedicel and calyx behind (destemmed). This line has been crossed with jalapeño, New Mexican ('NuMex Garnet') and blocky ('Maor') types. We have shown that the destemming trait can be readily transferred through a phenotypic evaluation in the field of 115 Garnet x UCD-14 and 39 Maor x UCD-14 F3 families (FIG. 1) and an additional 228 F3 families from these crosses.

We measured destemming force at the hard green stage when removing the fruit from the calyx with a straight pull with a MARK-10 force gauge (Copiague, N.Y.) from 15 fruit/replicate derived from 5 plants/plot in 2 replicates (including parental controls). The straight-pull measurement is a conservative estimate of destemming force compared with bending. It was used in this initial screen due to its high reproducibility. Initial results indicate that heritability is high, 60-70%, for both destemming force and frequency (fraction of fruit destemmed without breaking) and suggest that two genes control destemming ability. There were several lines with similar scores as UCD-14 and F3 selections outperformed commercial processing hybrids for destemming in green jalapeños.

Figure 2:
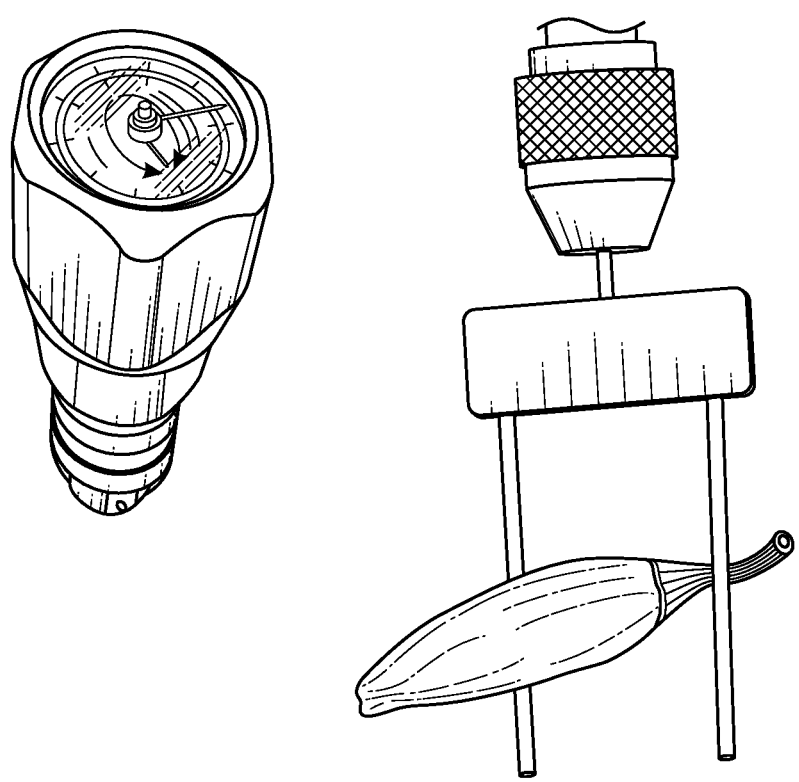
FIG. 2 shows Torque Watch with custom fork to measure bending force of peppers fruit. This instrument measures the maximum bending force at breaking of pedicel from fruit when twisting.
Figure 3:
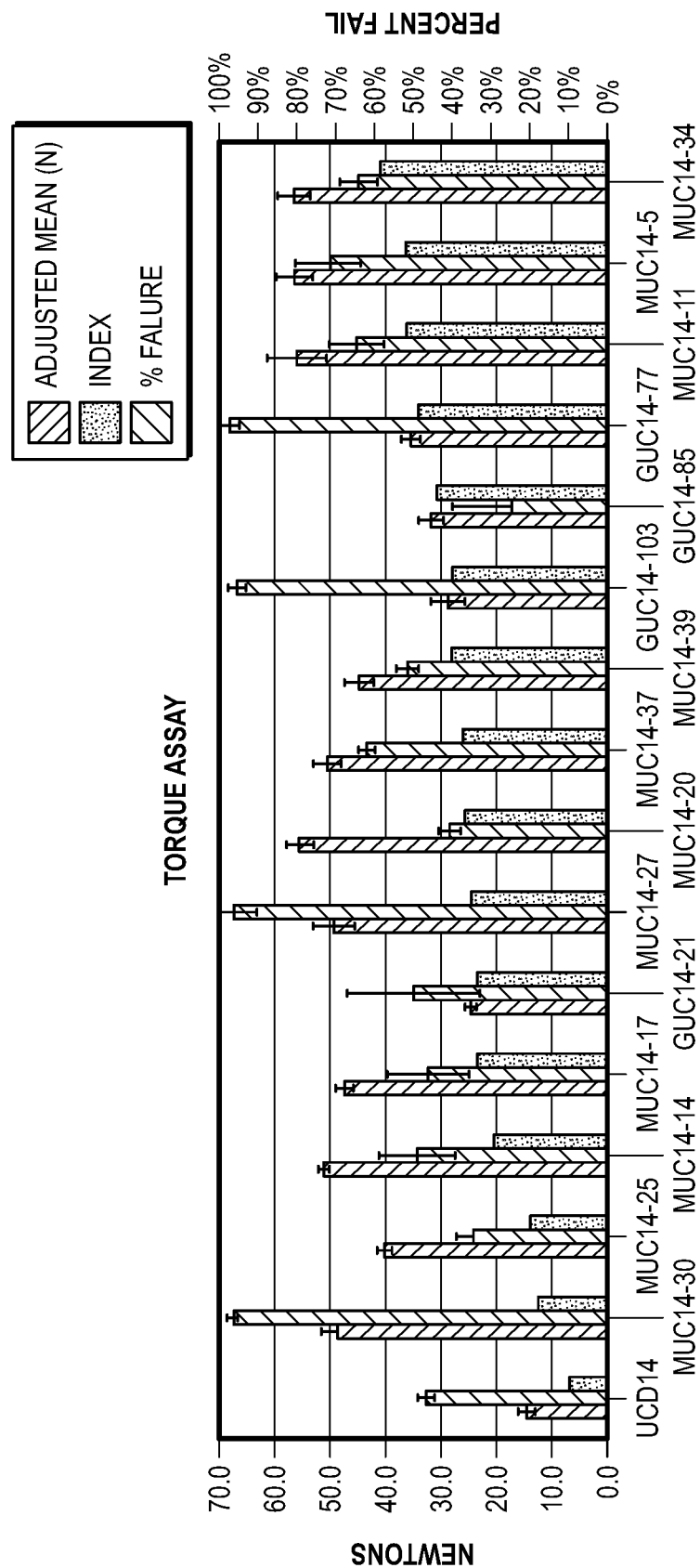
FIG. 3 shows destemming values for 21 MUC14 selections, 4 unrelated checks and UCD-14. Several lines have similar torque force (N) as UCD-14 parent.

We have also evaluated 15 F3-F4 families (with parental controls) in replicated trials (3 replicates of 10 plants/plot with 30 fruit samples per replicate) for destemming force using the MARK-10 force gauge and bending forces using a Torque Watch Gauge 651 (Honeywell, Columbus, Ohio, FIG. 2 and FIG. 3); fruit size/shape and pericarp thickness (FIG. 3). We developed an index that combined destemming force and failure rate. Index=Force (N)*destemming failure rate (%). The Torque watch method was reproducible and much more efficient than the pull method. The results from the replicated trial identified selections with similar destemming bending and pull forces as UCD-14.

Correlation between the pull and bending forces were 0.87 (P<0.002) and 0.72 for indices (P<0.001). We also measured bending forces at two different growth stages resulting in a 0.77 (p<0.001) correlation between stages.

Figure 4:
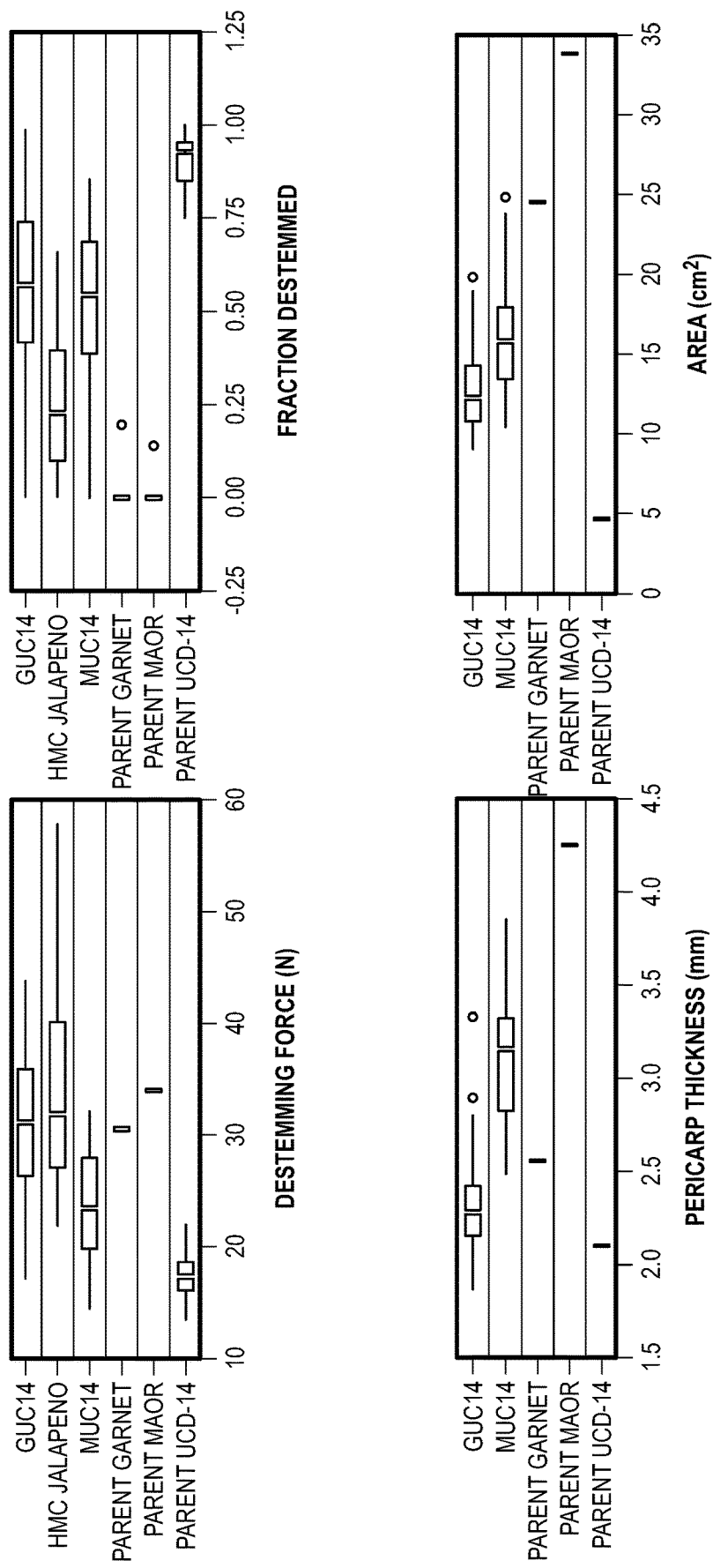
FIG. 4 shows distributions for fruit traits in F3 populations derived from Garnet and Maor crossed with UCD-14. Measurements were taken from a randomized complete block design with two replications and five plants sampled per replicate. (B to E) outlier box plots for the distributions of destemming (B, C), fruit pericarp thickness (D) and fruit size (E) for the Garnet x UCD-14 (GUC14) and the Maor x UCD-14 (MUC14) F3 populations and parental lines. For the destemming traits, lines in both populations had superior destemming properties, lower force and higher frequency than current red chile processing line, Garnet.
Figure 5B:
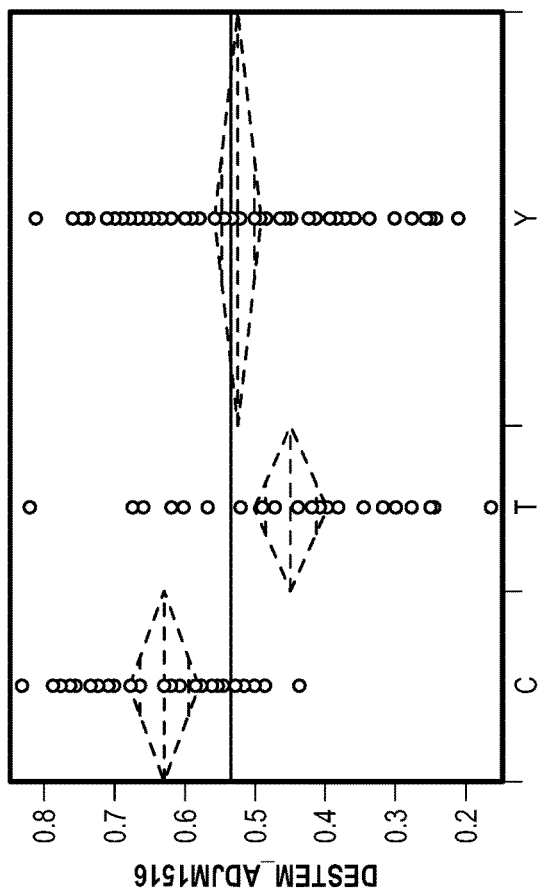

In trials, there were no significant correlations between destemming force, destemming frequency, and overall fruit size and pericarp thickness (FIG. 4). The distribution of phenotypic values for size, pericarp thickness and destemming along with the lack of trait correlations in both populations indicate that low destemming force, high destemming rate and favorable fruit traits can be combined through breeding. The Maor x UCD-14 population performed better than the Garnet x UCD-14 population in destemming while also producing larger fruit. The variation in fruit size in the Maor x UCD-14 population indicates that it may be valuable for transferring the destemming trait to a variety of pepper types.

We have identified a number of alleles associated with the low destemming force and high destemming frequency. These alleles are described in Table 1. The sequence of each 100 bp chromosomal segment surrounding each allele is identified in Table 1 is presented in Table 2.

TABLE 1

| rs# | alleles | Garnet | Maor | UCD14 | FavorableAllele | Trait | chrom | pos | Start | End |
|---|---|---|---|---|---|---|---|---|---|---|
| CA.10X.chr2__142933906 | C/A | C | C | A | A | Low Destem Force | chr02 | 142,933,906 | 142933856 | 142933956 |
| CA.10X.chr2__143240262 | T/C | T | T | C | C | Low Destem Force | chr02 | 143,240,262 | 143240212 | 143240312 |
| CA.10X.chr2__143710406 | G/A | G | G | A | A | Low Destem Force | chr02 | 143,710,406 | 143710356 | 143710456 |
| CA.10X.chr2__148097513 | G/A | A | A | G | G | Low Destem Force | chr02 | 148,097,513 | 148097463 | 148097563 |
| CA.10X.chr3__244366188 | A/G | A | A | G | G | Low Destem Force | chr03 | 244,366,188 | 244366138 | 244366238 |
| CA.10X.chr3__245138565 | G/A | A | A | G | G | Low Destem Force | chr03 | 245,138,565 | 245138515 | 245138615 |
| CA.10X.chr3__245358487 | T/C | C | C | T | T | Low Destem Force | chr03 | 245,358,487 | 245358437 | 245358537 |
| CA.10X.chr3__246172201 | A/G | A | A | G | G | Low Destem Force | chr03 | 246,172,201 | 246172151 | 246172251 |
| CA.10X.chr10__164006069 | C/T | C | C | T | T | High Destem Rate | chr10 | 164,006,069 | 164006019 | 164006119 |
| CA.10X.chr10__172967183 | T/C | T | T | C | C | High Destem Rate | chr10 | 172,967,183 | 172967133 | 172967233 |
| CA.10X.chr10__179169962 | G/A | G | G | A | A | High Destem Rate | chr10 | 179,169,962 | 179169912 | 179170012 |
| CA.10X.chr7__213622437 | G/A | G | A | R | A | Low Destem Force | chr7 | 213,622,437 | 213622387 | 213622487 |
| CA.10X.chr7__216504965 | C/A | A | A | M | A | Low Destem Force | chr7 | 216,504,965 | 216504915 | 216505015 |

TABLE 2

| rs# | Sequence |
|---|---|
| CA.10X.chr2_142933906 | TCCAAACTTTCAATTTATCATTCACAACCCCCAGCGTCTCATCAATCAAA[C]CTACATCATCCGGAAATAGCATATACCAAGGATCTTTTCCTTGAATACGC |
| CA.10X.chr2_143240262 | AAAAAACTTATTGAGAATGAAAGAGACTCTCAAACATGAGGAAGTAAGAA[T]TTTGTATAGGGCTACAGTGGATACATACTAGAAGAGGCATATCATGGCTA |
| CA.10X.chr2_143710406 | TGCTTCTGATCAACCTACAGCATTAGTGTAACCAACAACAGCAACTGTAC[G]AATTTCTTGACCATCTGTTCCTCCATGCCTCTTACGAGCAGCACGCTGCA |
| CA.10X.chr2_148097513 | AAACTTATTTACTGATCCACTGGACGGTATCTAGTAAGACTTAGACTTTC[A]TCATTCAAAACCTTAGTTTCAAACTGATGTGTGCTTTCAACTTTCCTATT |
| CA.10X.chr3_244366188 | GATGCAATTTCACAGACACCCTGGGACCATGAACCGTGCTTTGATACCAA[A]TTTGTCACGACCCAAATTGGGGCCCTAGCCGTGACGAGCATTCTCGAACT |
| CA.10X.chr3_245138565 | TTCCAAAAGTTGTAAGACTTACCCTACTTCAGGTGTCGTTTTGGCCTCAT[A]CTGTCCTTTCTTTCTAACCCTATCCAAAATTCAAGTTACAACCAAAGAAA |
| CA.10X.chr3_245358487 | GAGCAGACTGTATAATCAATATTAACACAAATGCAGAATCAGAGAGTAGA[C]TGTAATATTAACACAAATACACAGACAGAGAGCAGACTGTAATATTAACA |
| CA.10X.chr3_246172201 | ATCGGAATTGACCTTAACAGTATTGAGTCTGTTGTTACACAAACAGCTGG[A]TATTATAATGGGAGTGATTCTTTTGTCCCTTTGAATATGCGTACTGGGCA |
| CA.10X.chr10_164006069 | ATAAAGTTTTGGCCCAGACTACTGTGCCCCACACACTCTAGAATTACTTT[C]TTGCATAGTTTGAACAGACTCATCTGTGCCCAAACAACGTAAGAGTACTC |
| CA.10X.chr10_172967183 | TTTATGTTCTATGTAATTGTACAAAATGGTTACAGGTAGAGGAGAAAATT[T]AATGAATCATTCTATTGGTAGGAAAAGAAGTGAAAAAGGTAAAAGAGATG |
| CA.10X.chr10_179169962 | CACAAAAAACTGCTATAGCTTGAATAATCAGATTGAGTCCCTAATAATGA[G]GGGTATAATCAAATTCACCACCATAGCTCCAAATATGAACAATAATGCCT |
| CA.10X.chr7_213622437 | ATCATCACAACTTATAAAATCATGGATGCTAAATGTAAATGACTCACATA[G]GCTTGAGAAGTCCTTAAACTGAATATCATAAATCATGATTAATATAGCAT |

TABLE 2-continued

| rs# | Sequence |
|---|---|
| CA.10X.chr7_216504965 | CATGATAAAAAATCTACGTAATGCAGTTTGTCTGACTCCCTGGGACTCTA[A]AAAAAACTTAGGCTCTGATACCAAGTTTGTAACGCCCTGAAACTTGGTCT |

The genetic mechanism for ripe fruit abscission as developed for tomato (JOINTLESS) and pepper are believed to be different from those for green fruit and flowers. For example, the S locus confers easy abscission for ripe fruit in pepper with a tightly linked or pleiotropic effect of soft pericarp, unlike our pepper line. The abscission-signaling cascade is induced by the secreted peptide INFLORESCENCE DEFICIENT IN ABSCISSION (IDA). The IDA peptide is bound by two receptor-like protein kinases (RLKs), HEASA and HEASA-LIKE2 (HEA/HSL2). The IDA ligand promotes heterodimerization of HEA/HSL2 with LRR-RLK proteins that are members of the SOMATIC EMBRYOGENESIS RECEPTOR KINASE (SERK) family. The ligand receptor complex activates a MAP-kinase cascade activating KNOX transcription factors that induce the expression of cell wall remodeling and cell wall degrading enzymes. Interactions between the RLKs may be mediated via endosomal trafficking which is regulated by NEVERSHED (NEV), an ADP-ribosylation factor-GPase activating factor (ARF-GAP). This membrane trafficking may be regulated by the interaction of RLKs CAST AWAY (CST) and EVERSHED (EVR), which are thought to act as an inhibitors of abscission through interactions with HEA/HSL2. The timing and location of abscission may be modulated by interactions between the RLKs; EVR, CST, SERKs and HEA/HSL2 in the plasma membrane (Gubert, Catherine M., et al., *Plant signaling & behavior* 9.7 (2014): e29115; Leslie, Michelle E., et al. *Development* 137.3 (2010): 467-476; Taylor I, et al. *PLoS One.* 2016; 11(1):e0147203). In our analysis, we find three prominent genes in the organ abscission pathway, HSL2, CST and EVR, (underlined above) are segregating with destemming force and frequency in pepper.

Table 3A lists chromosomal regions defining a particular QTL position (numbered relative to the Pepper Genome UCD10X v1.0) and describing a region bound by "LOD 1.5 Left" and "LOD 1.5 Right." Any reference to a "region" of a chromosome as used herein refers to the region as bounded by these locations ("LOD 1.5 Left" and "LOD 1.5 Right") listed in Table 3A. Thus Table 3A provides regions within chromosomes 2, 3, 4, 7, and 10 at which QTL loci map for low destemming force or high destemming frequency. The markers shown in Table 1 map to the regions of Table 3A. Table 1 and Table 4 display polymorphic markers for QTL regions that have been identified as linked to the favorable low destemming force or high destemming frequency phenotype. The favorable allele, i.e., the allele linked to low destemming force or high destemming frequency, is indicated in both Table 1 and Table 4. Notably while most of the favorable alleles linked to the low destemming force are the UCD-14 allele, alleles in the region in chromosome 7 are from the Maor variety, indicating that in some cases lower destemming force can be at least partially aided by having the presence of an allele form the region of chromosome 7 from Maor.

TABLE 3A

Quantitative Trait Loci for destemming in pepper

| QTL Name | Trait Name | Chr | QTL Position* | LOD 1.5 Left | LOD 1.5 Right | LOD | Marker FDR p-value | Variance explained (%) | Candidate gene |
|---|---|---|---|---|---|---|---|---|---|
| dforc2 | Force | 2 | 143,684,899 | 140,090,900 | end | 3.0 | 0.048 | 15.7 | HSL2 |
| dforc3.2 | Force | 3 | 244,647,658 | 242,024,443 | end | 2.8 | 0.141 | 9.6 | EVR |
| dfreq4 | Frequency | 4 | 12,418,623 | 11,668,746 | 13,447,996 | 4.4 | na | 15.3 | CST |
| dforc7 | Force | 7 | 204,449,263 | 211,688,868 | 217,054,483 | 3.0 | 0.027 | 13.3 | |
| dfreq10 | Frequency | 10 | 159,807,690 | 155,833,663 | 166,509,209 | 5.1 | 0.001 | 17.7 | |
| | Frequency | 10 | 174,878,287 | 157,994,635 | 176,856,677 | 6.3 | 0.001 | 22.3 | |

All positions based on Pepper Genome UCD10X v1.0 (Hulse-Kemp et al. 2018).

TABLE 3B

Pepper candidate genes found under quantitative trait loci for destemming force.

| Arabidopsis ortholog | Symbol | Description | Pepper Chromosome | Pepper Gene v1.55 |
|---|---|---|---|---|
| AT5G65710.1 | HSL2 | haesa-like 2 | 2 | CA02g24590 |
| AT2G31880.1 | EVR,SOBIR1 | suppressor of bir1 1,evershed | 3 | CA03g26340 |
| AT4G35600.2 | CST | CST,Kin4,CX32 | 4 | CA04g05240 |

TABLE 4

| QTL | Marker | alleles | chrom | pos | Garnet | Maor | UCD14 | favorable allele |
|---|---|---|---|---|---|---|---|---|
| dforc2 | CA10X.chr2__140271520 | A/T | chr02 | 140,271,520 | A | A | T | T |
| dforc2 | CA10X.chr2__140278644 | G/A | chr02 | 140,278,644 | G | G | A | A |
| dforc2 | CA10X.chr2__140278671 | T/G | chr02 | 140,278,671 | T | T | G | G |
| dforc2 | CA10X.chr2__140278678 | C/T | chr02 | 140,278,678 | C | C | T | T |
| dforc2 | CA10X.chr2__140283214 | T/C | chr02 | 140,283,214 | T | T | C | C |
| dforc2 | CA10X.chr2__140283418 | A/G | chr02 | 140,283,418 | G | G | A | A |
| dforc2 | CA10X.chr2__140283431 | G/A | chr02 | 140,283,431 | A | A | G | G |
| dforc2 | CA10X.chr2__140283512 | T/C | chr02 | 140,283,512 | T | T | C | C |
| dforc2 | CA10X.chr2__140292077 | T/C | chr02 | 140,292,077 | T | T | C | C |
| dforc2 | CA10X.chr2__140292166 | T/G | chr02 | 140,292,166 | G | G | T | T |
| dforc2 | CA10X.chr2__140292171 | C/T | chr02 | 140,292,171 | T | T | C | C |
| dforc2 | CA10X.chr2__140292209 | G/A | chr02 | 140,292,209 | G | G | A | A |
| dforc2 | CA10X.chr2__140292297 | C/T | chr02 | 140,292,297 | T | T | C | C |
| dforc2 | CA10X.chr2__140292326 | T/C | chr02 | 140,292,326 | C | C | T | T |
| dforc2 | CA10X.chr2__140292442 | T/C | chr02 | 140,292,442 | C | C | T | T |
| dforc2 | CA10X.chr2__140292479 | C/T | chr02 | 140,292,479 | T | T | C | C |
| dforc2 | CA10X.chr2__140292526 | A/G | chr02 | 140,292,526 | A | A | G | G |
| dforc2 | CA10X.chr2__140292556 | C/T | chr02 | 140,292,556 | C | C | T | T |
| dforc2 | CA10X.chr2__140292572 | G/C | chr02 | 140,292,572 | G | G | C | C |
| dforc2 | CA10X.chr2__140293251 | T/C | chr02 | 140,293,251 | C | C | T | T |
| dforc2 | CA10X.chr2__140293260 | C/T | chr02 | 140,293,260 | T | T | C | C |
| dforc2 | CA10X.chr2__140293268 | G/A | chr02 | 140,293,268 | G | G | A | A |
| dforc2 | CA10X.chr2__140293279 | C/G | chr02 | 140,293,279 | G | G | C | C |
| dforc2 | CA10X.chr2__140293308 | T/C | chr02 | 140,293,308 | C | C | T | T |
| dforc2 | CA10X.chr2__140293309 | A/G | chr02 | 140,293,309 | G | G | A | A |
| dforc2 | CA10X.chr2__140293353 | G/A | chr02 | 140,293,353 | A | A | G | G |
| dforc2 | CA10X.chr2__140293364 | G/A | chr02 | 140,293,364 | G | G | A | A |
| dforc2 | CA10X.chr2__140293382 | C/A | chr02 | 140,293,382 | A | A | C | C |
| dforc2 | CA10X.chr2__140293428 | A/G | chr02 | 140,293,428 | G | G | A | A |
| dforc2 | CA10X.chr2__140293435 | A/G | chr02 | 140,293,435 | G | G | A | A |
| dforc2 | CA10X.chr2__140295485 | T/A | chr02 | 140,295,485 | A | A | T | T |
| dforc2 | CA10X.chr2__140295606 | T/C | chr02 | 140,295,606 | C | C | T | T |
| dforc2 | CA10X.chr2__140295646 | A/G | chr02 | 140,295,646 | A | A | G | G |
| dforc2 | CA10X.chr2__140295651 | C/T | chr02 | 140,295,651 | T | T | C | C |
| dforc2 | CA10X.chr2__140295677 | C/T | chr02 | 140,295,677 | T | T | C | C |
| dforc2 | CA10X.chr2__140295722 | G/A | chr02 | 140,295,722 | A | A | G | G |
| dforc2 | CA10X.chr2__140302683 | T/G | chr02 | 140,302,683 | G | G | T | T |
| dforc2 | CA10X.chr2__140302687 | A/G | chr02 | 140,302,687 | A | A | G | G |
| dforc2 | CA10X.chr2__140304787 | G/A | chr02 | 140,304,787 | G | G | A | A |
| dforc2 | CA10X.chr2__140304806 | T/C | chr02 | 140,304,806 | C | C | T | T |
| dforc2 | CA10X.chr2__140309443 | A/C | chr02 | 140,309,443 | A | A | C | C |
| dforc2 | CA10X.chr2__140309508 | A/G | chr02 | 140,309,508 | G | G | A | A |
| dforc2 | CA10X.chr2__140309582 | T/A | chr02 | 140,309,582 | T | T | A | A |
| dforc2 | CA10X.chr2__140309628 | G/C | chr02 | 140,309,628 | C | C | G | G |
| dforc2 | CA10X.chr2__140309675 | A/G | chr02 | 140,309,675 | A | A | G | G |
| dforc2 | CA10X.chr2__140309678 | T/C | chr02 | 140,309,678 | C | C | T | T |
| dforc2 | CA10X.chr2__140309687 | A/C | chr02 | 140,309,687 | A | A | C | C |
| dforc2 | CA10X.chr2__140309698 | A/G | chr02 | 140,309,698 | A | A | G | G |
| dforc2 | CA10X.chr2__140309710 | A/G | chr02 | 140,309,710 | A | A | G | G |
| dforc2 | CA10X.chr2__140309787 | G/A | chr02 | 140,309,787 | G | G | A | A |
| dforc2 | CA10X.chr2__140431296 | G/A | chr02 | 140,431,296 | G | G | A | A |
| dforc2 | CA10X.chr2__140435768 | T/A | chr02 | 140,435,768 | A | A | T | T |
| dforc2 | CA10X.chr2__141070305 | T/C | chr02 | 141,070,305 | C | C | T | T |
| dforc2 | CA10X.chr2__141121234 | A/G | chr02 | 141,121,234 | A | A | G | G |
| dforc2 | CA10X.chr2__141121343 | A/T | chr02 | 141,121,343 | T | T | A | A |
| dforc2 | CA10X.chr2__141122337 | C/T | chr02 | 141,122,337 | C | C | T | T |
| dforc2 | CA10X.chr2__141124695 | T/G | chr02 | 141,124,695 | T | T | G | G |
| dforc2 | CA10X.chr2__141124738 | T/C | chr02 | 141,124,738 | C | C | T | T |
| dforc2 | CA10X.chr2__141124743 | C/T | chr02 | 141,124,743 | C | C | T | T |
| dforc2 | CA10X.chr2__141144265 | A/G | chr02 | 141,144,265 | A | A | G | G |
| dforc2 | CA10X.chr2__141144290 | G/A | chr02 | 141,144,290 | G | G | A | A |
| dforc2 | CA10X.chr2__141227265 | C/T | chr02 | 141,227,265 | C | C | T | T |
| dforc2 | CA10X.chr2__141330019 | A/G | chr02 | 141,330,019 | G | G | A | A |
| dforc2 | CA10X.chr2__141330031 | C/T | chr02 | 141,330,031 | T | T | C | C |
| dforc2 | CA10X.chr2__141330089 | A/G | chr02 | 141,330,089 | G | G | A | A |
| dforc2 | CA10X.chr2__142029026 | G/A | chr02 | 142,029,026 | G | G | A | A |
| dforc2 | CA10X.chr2__142029027 | C/T | chr02 | 142,029,027 | C | C | T | T |
| dforc2 | CA10X.chr2__142029109 | C/G | chr02 | 142,029,109 | C | C | G | G |
| dforc2 | CA10X.chr2__142175256 | C/A | chr02 | 142,175,256 | C | C | A | A |
| dforc2 | CA10X.chr2__142175280 | A/G | chr02 | 142,175,280 | G | G | A | A |
| dforc2 | CA10X.chr2__142193602 | A/T | chr02 | 142,193,602 | A | A | T | T |
| dforc2 | CA10X.chr2__142368535 | G/T | chr02 | 142,368,535 | G | G | T | T |
| dforc2 | CA10X.chr2__142385303 | T/G | chr02 | 142,385,303 | T | T | G | G |
| dforc2 | CA10X.chr2__142400058 | A/G | chr02 | 142,400,058 | A | A | G | G |
| dforc2 | CA10X.chr2__142400059 | T/C | chr02 | 142,400,059 | T | T | C | C |
| dforc2 | CA10X.chr2__142400060 | C/G | chr02 | 142,400,060 | C | C | G | G |
| dforc2 | CA10X.chr2__142416568 | T/G | chr02 | 142,416,568 | T | T | G | G |

TABLE 4-continued

| QTL | Marker | alleles | chrom | pos | Garnet | Maor | UCD14 | favorable allele |
|---|---|---|---|---|---|---|---|---|
| dforc2 | CA10X.chr2__142538976 | T/C | chr02 | 142,538,976 | T | T | C | C |
| dforc2 | CA10X.chr2__142662404 | C/T | chr02 | 142,662,404 | C | C | T | T |
| dforc2 | CA10X.chr2__142933773 | C/T | chr02 | 142,933,773 | C | C | T | T |
| dforc2 | CA10X.chr2__142933906 | C/A | chr02 | 142,933,906 | C | C | A | A |
| dforc2 | CA10X.chr2__143119583 | A/G | chr02 | 143,119,583 | G | G | A | A |
| dforc2 | CA10X.chr2__143126393 | C/A | chr02 | 143,126,393 | C | C | A | A |
| dforc2 | CA10X.chr2__143126443 | C/T | chr02 | 143,126,443 | C | C | T | T |
| dforc2 | CA10X.chr2__143166645 | G/T | chr02 | 143,166,645 | T | T | G | G |
| dforc2 | CA10X.chr2__143166646 | A/T | chr02 | 143,166,646 | T | T | A | A |
| dforc2 | CA10X.chr2__143166706 | G/A | chr02 | 143,166,706 | A | A | G | G |
| dforc2 | CA10X.chr2__143170800 | G/T | chr02 | 143,170,800 | G | G | T | T |
| dforc2 | CA10X.chr2__143170812 | T/C | chr02 | 143,170,812 | C | C | T | T |
| dforc2 | CA10X.chr2__143171344 | C/T | chr02 | 143,171,344 | C | C | T | T |
| dforc2 | CA10X.chr2__143171390 | T/C | chr02 | 143,171,390 | T | T | C | C |
| dforc2 | CA10X.chr2__143171438 | G/A | chr02 | 143,171,438 | A | A | G | G |
| dforc2 | CA10X.chr2__143171876 | C/T | chr02 | 143,171,876 | T | T | C | C |
| dforc2 | CA10X.chr2__143241722 | T/G | chr02 | 143,241,722 | T | T | G | G |
| dforc2 | CA10X.chr2__143241736 | A/T | chr02 | 143,241,736 | A | A | T | T |
| dforc2 | CA10X.chr2__143708902 | A/C | chr02 | 143,708,902 | C | C | A | A |
| dforc2 | CA10X.chr2__143710406 | G/A | chr02 | 143,710,406 | G | G | A | A |
| dforc2 | CA10X.chr2__143734461 | A/C | chr02 | 143,734,461 | A | A | C | C |
| dforc2 | CA10X.chr2__144106168 | C/A | chr02 | 144,106,168 | A | A | C | C |
| dforc2 | CA10X.chr2__144363304 | C/T | chr02 | 144,363,304 | T | T | C | C |
| dforc2 | CA10X.chr2__144363317 | G/A | chr02 | 144,363,317 | A | A | G | G |
| dforc2 | CA10X.chr2__144363341 | G/A | chr02 | 144,363,341 | A | A | G | G |
| dforc2 | CA10X.chr2__144363351 | G/A | chr02 | 144,363,351 | G | G | A | A |
| dforc2 | CA10X.chr2__144405600 | A/G | chr02 | 144,405,600 | A | A | G | G |
| dforc2 | CA10X.chr2__144421048 | T/A | chr02 | 144,421,048 | T | T | A | A |
| dforc2 | CA10X.chr2__144421152 | C/A | chr02 | 144,421,152 | A | A | C | C |
| dforc2 | CA10X.chr2__144424280 | T/C | chr02 | 144,424,280 | T | T | C | C |
| dforc2 | CA10X.chr2__144424349 | G/A | chr02 | 144,424,349 | G | G | A | A |
| dforc2 | CA10X.chr2__144437422 | A/T | chr02 | 144,437,422 | T | T | A | A |
| dforc2 | CA10X.chr2__144440018 | G/A | chr02 | 144,440,018 | G | G | A | A |
| dforc2 | CA10X.chr2__144541225 | T/C | chr02 | 144,541,225 | T | T | C | C |
| dforc2 | CA10X.chr2__144541236 | A/G | chr02 | 144,541,236 | G | G | A | A |
| dforc2 | CA10X.chr2__144541240 | T/G | chr02 | 144,541,240 | G | G | T | T |
| dforc2 | CA10X.chr2__144541248 | T/A | chr02 | 144,541,248 | A | A | T | T |
| dforc2 | CA10X.chr2__144567163 | A/G | chr02 | 144,567,163 | G | G | A | A |
| dforc2 | CA10X.chr2__144567201 | T/C | chr02 | 144,567,201 | T | T | C | C |
| dforc2 | CA10X.chr2__144576881 | A/G | chr02 | 144,576,881 | G | G | A | A |
| dforc2 | CA10X.chr2__144687961 | A/T | chr02 | 144,687,961 | A | A | T | T |
| dforc2 | CA10X.chr2__144688034 | T/G | chr02 | 144,688,034 | G | G | T | T |
| dforc2 | CA10X.chr2__144713267 | T/C | chr02 | 144,713,267 | C | C | T | T |
| dforc2 | CA10X.chr2__144716639 | T/A | chr02 | 144,716,639 | T | T | A | A |
| dforc2 | CA10X.chr2__144716774 | G/A | chr02 | 144,716,774 | G | G | A | A |
| dforc2 | CA10X.chr2__144744023 | C/T | chr02 | 144,744,023 | C | C | T | T |
| dforc2 | CA10X.chr2__145523038 | A/C | chr02 | 145,523,038 | A | A | C | C |
| dforc2 | CA10X.chr2__146016845 | T/G | chr02 | 146,016,845 | G | G | T | T |
| dforc2 | CA10X.chr2__146499017 | G/A | chr02 | 146,499,017 | G | G | A | A |
| dforc2 | CA10X.chr2__146499285 | A/G | chr02 | 146,499,285 | A | A | G | G |
| dforc2 | CA10X.chr2__147034550 | C/A | chr02 | 147,034,550 | A | A | C | C |
| dforc2 | CA10X.chr2__147940382 | G/A | chr02 | 147,940,382 | G | G | A | A |
| dforc2 | CA10X.chr2__148212154 | A/C | chr02 | 148,212,154 | C | C | A | A |
| dforc2 | CA10X.chr2__148914502 | G/A | chr02 | 148,914,502 | G | G | A | A |
| dforc2 | CA10X.chr2__149185705 | T/C | chr02 | 149,185,705 | C | C | T | T |
| dforc2 | CA10X.chr2__149185727 | T/C | chr02 | 149,185,727 | C | C | T | T |
| dforc2 | CA10X.chr2__149185782 | C/T | chr02 | 149,185,782 | T | T | C | C |
| dforc2 | CA10X.chr2__149196565 | T/G | chr02 | 149,196,565 | T | T | G | G |
| dforc2 | CA10X.chr2__149196569 | G/T | chr02 | 149,196,569 | T | T | G | G |
| dforc2 | CA10X.chr2__149196570 | A/G | chr02 | 149,196,570 | A | A | G | G |
| dforc2 | CA10X.chr2__149196573 | T/G | chr02 | 149,196,573 | T | T | G | G |
| dforc2 | CA10X.chr2__149214259 | G/A | chr02 | 149,214,259 | A | A | G | G |
| dforc2 | CA10X.chr2__149322616 | T/C | chr02 | 149,322,616 | C | C | T | T |
| dforc2 | CA10X.chr2__149329581 | C/T | chr02 | 149,329,581 | C | C | T | T |
| dforc2 | CA10X.chr2__149330938 | T/C | chr02 | 149,330,938 | T | T | C | C |
| dforc2 | CA10X.chr2__149331246 | C/T | chr02 | 149,331,246 | T | T | C | C |
| dforc2 | CA10X.chr2__149331276 | T/C | chr02 | 149,331,276 | T | T | C | C |
| dforc2 | CA10X.chr2__149331450 | T/C | chr02 | 149,331,450 | T | T | C | C |
| dforc2 | CA10X.chr2__149334288 | C/T | chr02 | 149,334,288 | T | T | C | C |
| dforc2 | CA10X.chr2__149334355 | G/A | chr02 | 149,334,355 | A | A | G | G |
| dforc2 | CA10X.chr2__149358478 | A/G | chr02 | 149,358,478 | G | G | A | A |
| dforc2 | CA10X.chr2__149358561 | A/G | chr02 | 149,358,561 | G | G | A | A |
| dforc2 | CA10X.chr2__149358594 | C/A | chr02 | 149,358,594 | A | A | C | C |
| dforc2 | CA10X.chr2__149358603 | C/T | chr02 | 149,358,603 | C | C | T | T |
| dforc2 | CA10X.chr2__149358762 | A/G | chr02 | 149,358,762 | G | G | A | A |
| dforc2 | CA10X.chr2__149363218 | A/G | chr02 | 149,363,218 | G | G | A | A |
| dforc2 | CA10X.chr2__149363257 | G/A | chr02 | 149,363,257 | A | A | G | G |

TABLE 4-continued

| QTL | Marker | alleles | chrom | pos | Garnet | Maor | UCD14 | favorable allele |
|---|---|---|---|---|---|---|---|---|
| dforc2 | CA10X.chr2__149363259 | G/A | chr02 | 149,363,259 | G | G | A | A |
| dforc2 | CA10X.chr2__149363276 | G/A | chr02 | 149,363,276 | G | G | A | A |
| dforc2 | CA10X.chr2__149363315 | A/G | chr02 | 149,363,315 | A | A | G | G |
| dforc2 | CA10X.chr2__149372423 | C/T | chr02 | 149,372,423 | T | T | C | C |
| dforc2 | CA10X.chr2__149493893 | G/A | chr02 | 149,493,893 | A | A | G | G |
| dforc2 | CA10X.chr2__149493940 | A/G | chr02 | 149,493,940 | A | A | G | G |
| dforc2 | CA10X.chr2__149549958 | A/G | chr02 | 149,549,958 | G | G | A | A |
| dforc2 | CA10X.chr2__149554192 | T/G | chr02 | 149,554,192 | G | G | T | T |
| dforc2 | CA10X.chr2__149556075 | C/A | chr02 | 149,556,075 | C | C | A | A |
| dforc2 | CA10X.chr2__149556284 | T/C | chr02 | 149,556,284 | T | T | C | C |
| dforc2 | CA10X.chr2__149719254 | C/T | chr02 | 149,719,254 | C | C | T | T |
| dforc2 | CA10X.chr2__149890304 | C/A | chr02 | 149,890,304 | C | C | A | A |
| dforc2 | CA10X.chr2__149901182 | C/G | chr02 | 149,901,182 | C | C | G | G |
| dforc2 | CA10X.chr2__149951802 | C/T | chr02 | 149,951,802 | T | T | C | C |
| dforc2 | CA10X.chr2__151688917 | A/G | chr02 | 151,688,917 | G | G | A | A |
| dforc2 | CA10X.chr2__151688954 | G/A | chr02 | 151,688,954 | A | A | G | G |
| dforc2 | CA10X.chr2__151919040 | C/G | chr02 | 151,919,040 | G | G | C | C |
| dforc2 | CA10X.chr2__152078593 | T/C | chr02 | 152,078,593 | T | T | C | C |
| dforc2 | CA10X.chr2__152249855 | A/C | chr02 | 152,249,855 | A | A | C | C |
| dforc2 | CA10X.chr2__152249972 | T/C | chr02 | 152,249,972 | C | C | T | T |
| dforc2 | CA10X.chr2__152770165 | G/C | chr02 | 152,770,165 | G | G | C | C |
| dforc2 | CA10X.chr2__152770205 | A/T | chr02 | 152,770,205 | T | T | A | A |
| dforc2 | CA10X.chr2__153308977 | A/G | chr02 | 153,308,977 | G | G | A | A |
| dforc2 | CA10X.chr2__153694592 | A/G | chr02 | 153,694,592 | G | G | A | A |
| dforc2 | CA10X.chr2__153747259 | C/T | chr02 | 153,747,259 | C | C | T | T |
| dforc3.2 | CA10X.chr3__242310244 | A/C | chr03 | 242,310,244 | A | A | C | C |
| dforc3.2 | CA10X.chr3__242871661 | C/T | chr03 | 242,871,661 | T | T | C | C |
| dforc3.2 | CA10X.chr3__242882785 | T/C | chr03 | 242,882,785 | C | C | T | T |
| dforc3.2 | CA10X.chr3__243069605 | T/C | chr03 | 243,069,605 | T | T | C | C |
| dforc3.2 | CA10X.chr3__243126923 | C/T | chr03 | 243,126,923 | C | C | T | T |
| dforc3.2 | CA10X.chr3__243126979 | G/T | chr03 | 243,126,979 | G | G | T | T |
| dforc3.2 | CA10X.chr3__243127004 | G/A | chr03 | 243,127,004 | G | G | A | A |
| dforc3.2 | CA10X.chr3__243127010 | G/A | chr03 | 243,127,010 | A | A | G | G |
| dforc3.2 | CA10X.chr3__243130184 | G/A | chr03 | 243,130,184 | A | A | G | G |
| dforc3.2 | CA10X.chr3__243130207 | G/A | chr03 | 243,130,207 | G | G | A | A |
| dforc3.2 | CA10X.chr3__243131021 | G/A | chr03 | 243,131,021 | A | A | G | G |
| dforc3.2 | CA10X.chr3__243131127 | C/T | chr03 | 243,131,127 | C | C | T | T |
| dforc3.2 | CA10X.chr3__243131144 | G/A | chr03 | 243,131,144 | G | G | A | A |
| dforc3.2 | CA10X.chr3__243137836 | A/G | chr03 | 243,137,836 | A | A | G | G |
| dforc3.2 | CA10X.chr3__243138275 | T/C | chr03 | 243,138,275 | C | C | T | T |
| dforc3.2 | CA10X.chr3__243138283 | A/G | chr03 | 243,138,283 | A | A | G | G |
| dforc3.2 | CA10X.chr3__243172615 | G/T | chr03 | 243,172,615 | G | G | T | T |
| dforc3.2 | CA10X.chr3__243259655 | G/A | chr03 | 243,259,655 | A | A | G | G |
| dforc3.2 | CA10X.chr3__243259659 | T/C | chr03 | 243,259,659 | C | C | T | T |
| dforc3.2 | CA10X.chr3__243259663 | A/C | chr03 | 243,259,663 | A | A | C | C |
| dforc3.2 | CA10X.chr3__243259684 | G/A | chr03 | 243,259,684 | G | G | A | A |
| dforc3.2 | CA10X.chr3__243259905 | A/C | chr03 | 243,259,905 | A | A | C | C |
| dforc3.2 | CA10X.chr3__243420527 | G/A | chr03 | 243,420,527 | A | A | G | G |
| dforc3.2 | CA10X.chr3__243782120 | C/T | chr03 | 243,782,120 | C | C | T | T |
| dforc3.2 | CA10X.chr3__244330689 | T/C | chr03 | 244,330,689 | T | T | C | C |
| dforc3.2 | CA10X.chr3__244498277 | G/A | chr03 | 244,498,277 | G | G | A | A |
| dforc3.2 | CA10X.chr3__244542118 | G/A | chr03 | 244,542,118 | G | G | A | A |
| dforc3.2 | CA10X.chr3__244542124 | G/A | chr03 | 244,542,124 | A | A | G | G |
| dforc3.2 | CA10X.chr3__244542135 | T/G | chr03 | 244,542,135 | T | T | G | G |
| dforc3.2 | CA10X.chr3__244542136 | C/G | chr03 | 244,542,136 | C | C | G | G |
| dforc3.2 | CA10X.chr3__244542164 | C/T | chr03 | 244,542,164 | T | T | C | C |
| dforc3.2 | CA10X.chr3__244811887 | T/C | chr03 | 244,811,887 | C | C | T | T |
| dforc3.2 | CA10X.chr3__244811918 | T/A | chr03 | 244,811,918 | A | A | T | T |
| dforc3.2 | CA10X.chr3__245063507 | G/A | chr03 | 245,063,507 | G | G | A | A |
| dforc3.2 | CA10X.chr3__245071370 | A/C | chr03 | 245,071,370 | A | A | C | C |
| dforc3.2 | CA10X.chr3__245071395 | T/C | chr03 | 245,071,395 | C | C | T | T |
| dforc3.2 | CA10X.chr3__245071397 | G/T | chr03 | 245,071,397 | T | T | G | G |
| dforc3.2 | CA10X.chr3__245133936 | C/G | chr03 | 245,133,936 | G | G | C | C |
| dforc3.2 | CA10X.chr3__245133944 | C/G | chr03 | 245,133,944 | C | C | G | G |
| dforc3.2 | CA10X.chr3__245138416 | A/G | chr03 | 245,138,416 | G | G | A | A |
| dforc3.2 | CA10X.chr3__245138467 | C/A | chr03 | 245,138,467 | A | A | C | C |
| dforc3.2 | CA10X.chr3__245138481 | C/T | chr03 | 245,138,481 | C | C | T | T |
| dforc3.2 | CA10X.chr3__245175494 | G/A | chr03 | 245,175,494 | A | A | G | G |
| dforc3.2 | CA10X.chr3__245251368 | T/C | chr03 | 245,251,368 | C | C | T | T |
| dforc3.2 | CA10X.chr3__245358487 | T/C | chr03 | 245,358,487 | C | C | T | T |
| dforc3.2 | CA10X.chr3__246221782 | A/T | chr03 | 246,221,782 | T | T | A | A |
| dforc3.2 | CA10X.chr3__246236209 | T/G | chr03 | 246,236,209 | T | T | G | G |
| dforc3.2 | CA10X.chr3__246242383 | A/T | chr03 | 246,242,383 | A | A | T | T |
| dforc3.2 | CA10X.chr3__246628503 | A/T | chr03 | 246,628,503 | A | A | T | T |
| dforc3.2 | CA10X.chr3__247756058 | C/T | chr03 | 247,756,058 | C | C | T | T |
| dforc3.2 | CA10X.chr3__248516747 | A/T | chr03 | 248,516,747 | T | T | A | A |
| dforc3.2 | CA10X.chr3__249261569 | T/C | chr03 | 249,261,569 | T | T | C | C |

TABLE 4-continued

| QTL | Marker | alleles | chrom | pos | Garnet | Maor | UCD14 | favorable allele |
|---|---|---|---|---|---|---|---|---|
| dforc3.2 | CA10X.chr3__249915095 | T/A | chr03 | 249,915,095 | T | T | A | A |
| dforc3.2 | CA10X.chr3__249915355 | A/C | chr03 | 249,915,355 | C | C | A | A |
| dforc3.2 | CA10X.chr3__249915382 | C/T | chr03 | 249,915,382 | T | T | C | C |
| dforc3.2 | CA10X.chr3__249930469 | T/C | chr03 | 249,930,469 | C | C | T | T |
| dforc3.2 | CA10X.chr3__250630395 | G/T | chr03 | 250,630,395 | T | T | G | G |
| dforc3.2 | CA10X.chr3__251649186 | T/G | chr03 | 251,649,186 | G | G | T | T |
| dforc3.2 | CA10X.chr3__251959521 | G/C | chr03 | 251,959,521 | C | C | G | G |
| dforc3.2 | CA10X.chr3__251959535 | G/A | chr03 | 251,959,535 | A | A | G | G |
| dforc3.2 | CA10X.chr3__251959604 | C/T | chr03 | 251,959,604 | T | T | C | C |
| dforc3.2 | CA10X.chr3__251971131 | G/A | chr03 | 251,971,131 | A | A | G | G |
| dforc3.2 | CA10X.chr3__251989298 | A/G | chr03 | 251,989,298 | A | A | G | G |
| dforc3.2 | CA10X.chr3__252090461 | A/G | chr03 | 252,090,461 | A | A | G | G |
| dforc3.2 | CA10X.chr3__252090506 | C/A | chr03 | 252,090,506 | C | C | A | A |
| dforc3.2 | CA10X.chr3__252145157 | T/G | chr03 | 252,145,157 | T | T | G | G |
| dforc3.2 | CA10X.chr3__252158710 | A/G | chr03 | 252,158,710 | A | A | G | G |
| dforc3.2 | CA10X.chr3__252158764 | A/G | chr03 | 252,158,764 | G | G | A | A |
| dforc3.2 | CA10X.chr3__252158865 | C/T | chr03 | 252,158,865 | C | C | T | T |
| dforc3.2 | CA10X.chr3__252160966 | A/G | chr03 | 252,160,966 | G | G | A | A |
| dforc3.2 | CA10X.chr3__252161008 | G/A | chr03 | 252,161,008 | G | G | A | A |
| dforc3.2 | CA10X.chr3__252168599 | T/C | chr03 | 252,168,599 | C | C | T | T |
| dforc3.2 | CA10X.chr3__252448391 | C/T | chr03 | 252,448,391 | T | T | C | C |
| dforc3.2 | CA10X.chr3__252448413 | A/G | chr03 | 252,448,413 | A | A | G | G |
| dforc3.2 | CA10X.chr3__252470752 | C/T | chr03 | 252,470,752 | T | T | C | C |
| dforc3.2 | CA10X.chr3__252993135 | A/G | chr03 | 252,993,135 | G | G | A | A |
| dforc3.2 | CA10X.chr3__253634419 | G/A | chr03 | 253,634,419 | A | A | G | G |
| dforc3.2 | CA10X.chr3__253636971 | T/G | chr03 | 253,636,971 | G | G | T | T |
| dforc3.2 | CA10X.chr3__253650969 | C/T | chr03 | 253,650,969 | C | C | T | T |
| dforc3.2 | CA10X.chr3__253651059 | A/G | chr03 | 253,651,059 | G | G | A | A |
| dforc3.2 | CA10X.chr3__253664005 | T/G | chr03 | 253,664,005 | T | T | G | G |
| dforc3.2 | CA10X.chr3__253858650 | C/G | chr03 | 253,858,650 | G | G | C | C |
| dforc3.2 | CA10X.chr3__253860370 | C/T | chr03 | 253,860,370 | C | C | T | T |
| dforc3.2 | CA10X.chr3__254361443 | G/A | chr03 | 254,361,443 | G | G | A | A |
| dforc3.2 | CA10X.chr3__254789177 | C/T | chr03 | 254,789,177 | T | T | C | C |
| dforc3.2 | CA10X.chr3__255144876 | T/C | chr03 | 255,144,876 | C | C | T | T |
| dforc3.2 | CA10X.chr3__255226274 | T/C | chr03 | 255,226,274 | C | C | T | T |
| dforc3.2 | CA10X.chr3__255404767 | T/A | chr03 | 255,404,767 | A | A | T | T |
| dforc3.2 | CA10X.chr3__255652804 | A/C | chr03 | 255,652,804 | C | C | A | A |
| dforc3.2 | CA10X.chr3__256182539 | T/C | chr03 | 256,182,539 | C | C | T | T |
| dforc3.2 | CA10X.chr3__258040046 | A/G | chr03 | 258,040,046 | A | A | G | G |
| dforc3.2 | CA10X.chr3__258059700 | A/G | chr03 | 258,059,700 | G | G | A | A |
| dforc3.2 | CA10X.chr3__258087766 | T/C | chr03 | 258,087,766 | C | C | T | T |
| dforc3.2 | CA10X.chr3__258089569 | T/C | chr03 | 258,089,569 | T | T | C | C |
| dforc3.2 | CA10X.chr3__258090721 | A/G | chr03 | 258,090,721 | A | A | G | G |
| dforc3.2 | CA10X.chr3__258767345 | G/A | chr03 | 258,767,345 | A | A | G | G |
| dforc3.2 | CA10X.chr3__258829031 | C/T | chr03 | 258,829,031 | T | T | C | C |
| dforc3.2 | CA10X.chr3__259814536 | C/A | chr03 | 259,814,536 | C | C | A | A |
| dforc3.2 | CA10X.chr3__259867983 | T/C | chr03 | 259,867,983 | C | C | T | T |
| dforc3.2 | CA10X.chr3__260043700 | A/G | chr03 | 260,043,700 | G | G | A | A |
| dforc3.2 | CA10X.chr3__260586271 | G/A | chr03 | 260,586,271 | G | G | A | A |
| dforc3.2 | CA10X.chr3__261358999 | A/C | chr03 | 261,358,999 | C | C | A | A |
| dforc3.2 | CA10X.chr3__262199202 | A/G | chr03 | 262,199,202 | A | A | G | G |
| dforc3.2 | CA10X.chr3__262199268 | A/G | chr03 | 262,199,268 | A | A | G | G |
| dforc3.2 | CA10X.chr3__262813092 | C/T | chr03 | 262,813,092 | T | T | C | C |
| dforc3.2 | CA10X.chr3__263097987 | T/C | chr03 | 263,097,987 | C | C | T | T |
| dforc3.2 | CA10X.chr3__263287440 | G/A | chr03 | 263,287,440 | A | A | G | G |
| dforc3.2 | CA10X.chr3__264888829 | T/C | chr03 | 264,888,829 | T | T | C | C |
| dforc3.2 | CA10X.chr3__264888993 | G/C | chr03 | 264,888,993 | G | G | C | C |
| dforc3.2 | CA10X.chr3__264889002 | G/A | chr03 | 264,889,002 | A | A | G | G |
| dforc3.2 | CA10X.chr3__264889034 | T/A | chr03 | 264,889,034 | A | A | T | T |
| dforc3.2 | CA10X.chr3__264889070 | A/G | chr03 | 264,889,070 | G | G | A | A |
| dforc3.2 | CA10X.chr3__265311345 | A/G | chr03 | 265,311,345 | A | A | G | G |
| dforc3.2 | CA10X.chr3__265311371 | G/A | chr03 | 265,311,371 | A | A | G | G |
| dforc3.2 | CA10X.chr3__265311447 | A/G | chr03 | 265,311,447 | A | A | G | G |
| dforc3.2 | CA10X.chr3__265311557 | C/T | chr03 | 265,311,557 | T | T | C | C |
| dforc3.2 | CA10X.chr3__265442955 | T/C | chr03 | 265,442,955 | T | T | C | C |
| dforc3.2 | CA10X.chr3__265443041 | A/G | chr03 | 265,443,041 | A | A | G | G |
| dforc3.2 | CA10X.chr3__265443076 | A/G | chr03 | 265,443,076 | G | G | A | A |
| dforc3.2 | CA10X.chr3__265528976 | T/C | chr03 | 265,528,976 | C | C | T | T |
| dforc3.2 | CA10X.chr3__265751025 | G/T | chr03 | 265,751,025 | G | G | T | T |
| dforc3.2 | CA10X.chr3__265779725 | G/T | chr03 | 265,779,725 | T | T | G | G |
| dforc3.2 | CA10X.chr3__265810892 | T/A | chr03 | 265,810,892 | T | T | A | A |
| dforc3.2 | CA10X.chr3__266051647 | C/G | chr03 | 266,051,647 | C | C | G | G |
| dforc3.2 | CA10X.chr3__266125048 | G/A | chr03 | 266,125,048 | G | G | A | A |
| dforc3.2 | CA10X.chr3__266133344 | A/T | chr03 | 266,133,344 | T | T | A | A |
| dforc3.2 | CA10X.chr3__266137935 | T/C | chr03 | 266,137,935 | C | C | T | T |
| dforc3.2 | CA10X.chr3__266137944 | C/T | chr03 | 266,137,944 | C | C | T | T |
| dforc3.2 | CA10X.chr3__266137947 | A/G | chr03 | 266,137,947 | A | A | G | G |

TABLE 4-continued

| QTL | Marker | alleles | chrom | pos | Garnet | Maor | UCD14 | favorable allele |
|---|---|---|---|---|---|---|---|---|
| dforc3.2 | CA10X.chr3_266137963 | C/T | chr03 | 266,137,963 | T | T | C | C |
| dforc3.2 | CA10X.chr3_266325826 | A/G | chr03 | 266,325,826 | G | G | A | A |
| dforc3.2 | CA10X.chr3_266896958 | C/T | chr03 | 266,896,958 | T | T | C | C |
| dforc3.2 | CA10X.chr3_266897061 | C/A | chr03 | 266,897,061 | A | A | C | C |
| dforc3.2 | CA10X.chr3_267564928 | G/C | chr03 | 267,564,928 | G | G | C | C |
| dforc3.2 | CA10X.chr3_267880545 | A/C | chr03 | 267,880,545 | C | C | A | A |
| dforc3.2 | CA10X.chr3_268001563 | C/A | chr03 | 268,001,563 | A | A | C | C |
| dforc3.2 | CA10X.chr3_268017856 | T/C | chr03 | 268,017,856 | C | C | T | T |
| dforc3.2 | CA10X.chr3_268030053 | A/T | chr03 | 268,030,053 | T | T | A | A |
| dforc3.2 | CA10X.chr3_268047653 | T/C | chr03 | 268,047,653 | C | C | T | T |
| dforc3.2 | CA10X.chr3_268047663 | G/T | chr03 | 268,047,663 | G | G | T | T |
| dforc3.2 | CA10X.chr3_268054670 | G/A | chr03 | 268,054,670 | G | G | A | A |
| dforc3.2 | CA10X.chr3_268054719 | T/C | chr03 | 268,054,719 | C | C | T | T |
| dforc3.2 | CA10X.chr3_268054782 | T/C | chr03 | 268,054,782 | T | T | C | C |
| dforc3.2 | CA10X.chr3_268054818 | G/T | chr03 | 268,054,818 | T | T | G | G |
| dforc3.2 | CA10X.chr3_268061467 | A/G | chr03 | 268,061,467 | G | G | A | A |
| dforc3.2 | CA10X.chr3_268209516 | A/C | chr03 | 268,209,516 | A | A | C | C |
| dforc3.2 | CA10X.chr3_268215402 | A/T | chr03 | 268,215,402 | A | A | T | T |
| dforc3.2 | CA10X.chr3_268215443 | A/C | chr03 | 268,215,443 | A | A | C | C |
| dforc3.2 | CA10X.chr3_268215731 | A/G | chr03 | 268,215,731 | A | A | G | G |
| dforc3.2 | CA10X.chr3_268338573 | G/A | chr03 | 268,338,573 | A | A | G | G |
| dforc3.2 | CA10X.chr3_268420844 | C/T | chr03 | 268,420,844 | T | T | C | C |
| dforc3.2 | CA10X.chr3_268501891 | A/C | chr03 | 268,501,891 | C | C | A | A |
| dforc3.2 | CA10X.chr3_268514966 | C/T | chr03 | 268,514,966 | C | C | T | T |
| dforc3.2 | CA10X.chr3_268540480 | A/G | chr03 | 268,540,480 | A | A | G | G |
| dforc3.2 | CA10X.chr3_268540580 | G/A | chr03 | 268,540,580 | A | A | G | G |
| dforc3.2 | CA10X.chr3_268540604 | T/A | chr03 | 268,540,604 | A | A | T | T |
| dforc3.2 | CA10X.chr3_268588423 | C/A | chr03 | 268,588,423 | A | A | C | C |
| dforc3.2 | CA10X.chr3_268643387 | T/C | chr03 | 268,643,387 | T | T | C | C |
| dforc3.2 | CA10X.chr3_268645891 | T/C | chr03 | 268,645,891 | T | T | C | C |
| dforc3.2 | CA10X.chr3_268645908 | A/C | chr03 | 268,645,908 | C | C | A | A |
| dforc3.2 | CA10X.chr3_268645937 | C/T | chr03 | 268,645,937 | C | C | T | T |
| dforc3.2 | CA10X.chr3_268645971 | A/G | chr03 | 268,645,971 | G | G | A | A |
| dforc3.2 | CA10X.chr3_268645983 | A/G | chr03 | 268,645,983 | G | G | A | A |
| dforc3.2 | CA10X.chr3_268652758 | A/T | chr03 | 268,652,758 | A | A | T | T |
| dforc3.2 | CA10X.chr3_268652811 | A/G | chr03 | 268,652,811 | G | G | A | A |
| dforc3.2 | CA10X.chr3_268652941 | T/C | chr03 | 268,652,941 | C | C | T | T |
| dforc3.2 | CA10X.chr3_268652952 | C/G | chr03 | 268,652,952 | G | G | C | C |
| dforc3.2 | CA10X.chr3_268664903 | C/T | chr03 | 268,664,903 | C | C | T | T |
| dforc3.2 | CA10X.chr3_268664959 | A/G | chr03 | 268,664,959 | G | G | A | A |
| dforc3.2 | CA10X.chr3_268808741 | T/C | chr03 | 268,808,741 | C | C | T | T |
| dforc3.2 | CA10X.chr3_268846147 | C/A | chr03 | 268,846,147 | A | A | C | C |
| dforc3.2 | CA10X.chr3_268846354 | G/A | chr03 | 268,846,354 | A | A | G | G |
| dforc3.2 | CA10X.chr3_268846362 | A/T | chr03 | 268,846,362 | T | T | A | A |
| dforc3.2 | CA10X.chr3_268846363 | T/G | chr03 | 268,846,363 | T | T | G | G |
| dforc3.2 | CA10X.chr3_268846368 | G/A | chr03 | 268,846,368 | A | A | G | G |
| dforc3.2 | CA10X.chr3_268846393 | A/G | chr03 | 268,846,393 | A | A | G | G |
| dforc3.2 | CA10X.chr3_268846455 | T/C | chr03 | 268,846,455 | C | C | T | T |
| dforc3.2 | CA10X.chr3_268846489 | T/C | chr03 | 268,846,489 | T | T | C | C |
| dforc3.2 | CA10X.chr3_268850483 | A/C | chr03 | 268,850,483 | C | C | A | A |
| dforc3.2 | CA10X.chr3_268850484 | C/A | chr03 | 268,850,484 | C | C | A | A |
| dforc3.2 | CA10X.chr3_268850485 | A/T | chr03 | 268,850,485 | A | A | T | T |
| dforc3.2 | CA10X.chr3_269020103 | A/G | chr03 | 269,020,103 | G | G | A | A |
| dforc3.2 | CA10X.chr3_269030652 | G/T | chr03 | 269,030,652 | T | T | G | G |
| dforc3.2 | CA10X.chr3_269030685 | A/G | chr03 | 269,030,685 | A | A | G | G |
| dforc3.2 | CA10X.chr3_269030701 | T/C | chr03 | 269,030,701 | T | T | C | C |
| dforc3.2 | CA10X.chr3_269707488 | A/G | chr03 | 269,707,488 | G | G | A | A |
| dforc3.2 | CA10X.chr3_269707506 | G/A | chr03 | 269,707,506 | A | A | G | G |
| dforc3.2 | CA10X.chr3_269707574 | C/T | chr03 | 269,707,574 | C | C | T | T |
| dforc3.2 | CA10X.chr3_269707610 | A/T | chr03 | 269,707,610 | T | T | A | A |
| dforc3.2 | CA10X.chr3_269707742 | T/C | chr03 | 269,707,742 | C | C | T | T |
| dforc3.2 | CA10X.chr3_269785063 | A/G | chr03 | 269,785,063 | G | G | A | A |
| dforc3.2 | CA10X.chr3_269785066 | G/A | chr03 | 269,785,066 | A | A | G | G |
| dforc3.2 | CA10X.chr3_270087637 | A/G | chr03 | 270,087,637 | A | A | G | G |
| dforc7 | CA10X.chr7_211711944 | C/T | chr07 | 211,711,944 | C | C | T | C |
| dforc7 | CA10X.chr7_211721508 | A/C | chr07 | 211,721,508 | C | C | A | C |
| dforc7 | CA10X.chr7_211721537 | A/G | chr07 | 211,721,537 | G | G | A | G |
| dforc7 | CA10X.chr7_211721549 | G/A | chr07 | 211,721,549 | A | A | G | A |
| dforc7 | CA10X.chr7_211721815 | C/A | chr07 | 211,721,815 | A | A | C | A |
| dforc7 | CA10X.chr7_211721943 | A/G | chr07 | 211,721,943 | G | G | A | G |
| dforc7 | CA10X.chr7_211729229 | G/A | chr07 | 211,729,229 | A | A | G | A |
| dforc7 | CA10X.chr7_211731613 | C/A | chr07 | 211,731,613 | C | C | A | C |
| dforc7 | CA10X.chr7_211731694 | C/T | chr07 | 211,731,694 | C | C | T | C |
| dforc7 | CA10X.chr7_211732922 | T/C | chr07 | 211,732,922 | T | T | C | T |
| dforc7 | CA10X.chr7_211732955 | C/T | chr07 | 211,732,955 | C | C | T | C |
| dforc7 | CA10X.chr7_211733024 | G/T | chr07 | 211,733,024 | T | T | G | T |
| dforc7 | CA10X.chr7_211733234 | T/C | chr07 | 211,733,234 | C | C | T | C |

TABLE 4-continued

| QTL | Marker | alleles | chrom | pos | Garnet | Maor | UCD14 | favorable allele |
|---|---|---|---|---|---|---|---|---|
| dforc7 | CA10X.chr7__211765487 | G/A | chr07 | 211,765,487 | A | A | G | A |
| dforc7 | CA10X.chr7__211765535 | C/T | chr07 | 211,765,535 | T | T | C | T |
| dforc7 | CA10X.chr7__211765620 | A/G | chr07 | 211,765,620 | G | G | A | G |
| dforc7 | CA10X.chr7__211858467 | G/A | chr07 | 211,858,467 | G | G | A | G |
| dforc7 | CA10X.chr7__211858507 | T/C | chr07 | 211,858,507 | C | C | T | C |
| dforc7 | CA10X.chr7__211894527 | G/C | chr07 | 211,894,527 | G | G | C | G |
| dforc7 | CA10X.chr7__211894543 | A/G | chr07 | 211,894,543 | G | G | A | G |
| dforc7 | CA10X.chr7__211894560 | G/A | chr07 | 211,894,560 | A | A | G | A |
| dforc7 | CA10X.chr7__211937499 | A/G | chr07 | 211,937,499 | G | G | A | G |
| dforc7 | CA10X.chr7__211937500 | C/A | chr07 | 211,937,500 | A | A | C | A |
| dforc7 | CA10X.chr7__211939846 | T/C | chr07 | 211,939,846 | T | T | C | T |
| dforc7 | CA10X.chr7__211939948 | A/G | chr07 | 211,939,948 | A | A | G | A |
| dforc7 | CA10X.chr7__211942951 | T/C | chr07 | 211,942,951 | T | T | C | T |
| dforc7 | CA10X.chr7__211943014 | G/A | chr07 | 211,943,014 | A | A | G | A |
| dforc7 | CA10X.chr7__211943016 | A/C | chr07 | 211,943,016 | A | A | C | A |
| dforc7 | CA10X.chr7__211943100 | T/C | chr07 | 211,943,100 | C | C | T | C |
| dforc7 | CA10X.chr7__211945590 | C/T | chr07 | 211,945,590 | T | T | C | T |
| dforc7 | CA10X.chr7__211945634 | T/C | chr07 | 211,945,634 | C | C | T | C |
| dforc7 | CA10X.chr7__211990011 | T/C | chr07 | 211,990,011 | C | C | T | C |
| dforc7 | CA10X.chr7__212011152 | A/C | chr07 | 212,011,152 | A | A | C | A |
| dforc7 | CA10X.chr7__212073626 | C/T | chr07 | 212,073,626 | N | T | C | T |
| dforc7 | CA10X.chr7__212073646 | T/G | chr07 | 212,073,646 | N | G | T | G |
| dforc7 | CA10X.chr7__212073919 | G/C | chr07 | 212,073,919 | C | C | G | C |
| dforc7 | CA10X.chr7__212073961 | T/A | chr07 | 212,073,961 | T | T | A | T |
| dforc7 | CA10X.chr7__212075934 | T/C | chr07 | 212,075,934 | T | T | C | T |
| dforc7 | CA10X.chr7__212076049 | C/T | chr07 | 212,076,049 | T | T | C | T |
| dforc7 | CA10X.chr7__212081497 | C/T | chr07 | 212,081,497 | T | T | C | T |
| dforc7 | CA10X.chr7__212083737 | C/T | chr07 | 212,083,737 | C | C | T | C |
| dforc7 | CA10X.chr7__212083750 | T/A | chr07 | 212,083,750 | T | T | A | T |
| dforc7 | CA10X.chr7__212084654 | C/T | chr07 | 212,084,654 | C | C | T | C |
| dforc7 | CA10X.chr7__212084727 | T/C | chr07 | 212,084,727 | T | T | C | T |
| dforc7 | CA10X.chr7__212084740 | T/C | chr07 | 212,084,740 | T | T | C | T |
| dforc7 | CA10X.chr7__212124705 | G/T | chr07 | 212,124,705 | G | G | T | G |
| dforc7 | CA10X.chr7__212124813 | A/G | chr07 | 212,124,813 | G | G | A | G |
| dforc7 | CA10X.chr7__212124939 | T/C | chr07 | 212,124,939 | T | T | C | T |
| dforc7 | CA10X.chr7__212126831 | C/A | chr07 | 212,126,831 | A | A | C | A |
| dforc7 | CA10X.chr7__212146483 | A/G | chr07 | 212,146,483 | G | G | A | G |
| dforc7 | CA10X.chr7__212146618 | A/G | chr07 | 212,146,618 | A | A | G | A |
| dforc7 | CA10X.chr7__213005458 | G/A | chr07 | 213,005,458 | G | G | A | G |
| dforc7 | CA10X.chr7__213092600 | G/A | chr07 | 213,092,600 | A | A | G | A |
| dforc7 | CA10X.chr7__213145533 | C/T | chr07 | 213,145,533 | C | C | T | C |
| dforc7 | CA10X.chr7__213145563 | T/C | chr07 | 213,145,563 | C | C | T | C |
| dforc7 | CA10X.chr7__213145625 | A/G | chr07 | 213,145,625 | G | G | A | G |
| dforc7 | CA10X.chr7__213145642 | G/T | chr07 | 213,145,642 | T | T | G | T |
| dforc7 | CA10X.chr7__213172727 | T/C | chr07 | 213,172,727 | C | C | T | C |
| dforc7 | CA10X.chr7__213172743 | T/C | chr07 | 213,172,743 | T | T | C | T |
| dforc7 | CA10X.chr7__213174685 | T/C | chr07 | 213,174,685 | T | T | C | T |
| dforc7 | CA10X.chr7__213187216 | G/C | chr07 | 213,187,216 | G | G | C | G |
| dforc7 | CA10X.chr7__213188385 | C/G | chr07 | 213,188,385 | N | C | G | C |
| dforc7 | CA10X.chr7__213192206 | C/A | chr07 | 213,192,206 | N | C | A | C |
| dforc7 | CA10X.chr7__213193099 | C/T | chr07 | 213,193,099 | C | C | T | C |
| dforc7 | CA10X.chr7__213193128 | T/C | chr07 | 213,193,128 | T | T | C | T |
| dforc7 | CA10X.chr7__213193185 | A/C | chr07 | 213,193,185 | A | A | C | A |
| dforc7 | CA10X.chr7__213193379 | A/T | chr07 | 213,193,379 | T | T | A | T |
| dforc7 | CA10X.chr7__213194140 | A/T | chr07 | 213,194,140 | A | A | T | A |
| dforc7 | CA10X.chr7__213211643 | A/T | chr07 | 213,211,643 | T | T | A | T |
| dforc7 | CA10X.chr7__213211649 | T/C | chr07 | 213,211,649 | C | C | T | C |
| dforc7 | CA10X.chr7__213211689 | C/T | chr07 | 213,211,689 | T | T | C | T |
| dforc7 | CA10X.chr7__213212778 | C/T | chr07 | 213,212,778 | T | T | C | T |
| dforc7 | CA10X.chr7__213213929 | A/G | chr07 | 213,213,929 | G | G | A | G |
| dforc7 | CA10X.chr7__213214795 | T/C | chr07 | 213,214,795 | C | C | T | C |
| dforc7 | CA10X.chr7__213214860 | T/A | chr07 | 213,214,860 | T | T | A | T |
| dforc7 | CA10X.chr7__213215049 | A/G | chr07 | 213,215,049 | G | G | A | G |
| dforc7 | CA10X.chr7__213215096 | A/G | chr07 | 213,215,096 | G | G | A | G |
| dforc7 | CA10X.chr7__213218644 | C/T | chr07 | 213,218,644 | C | C | T | C |
| dforc7 | CA10X.chr7__213218714 | G/A | chr07 | 213,218,714 | A | A | G | A |
| dforc7 | CA10X.chr7__213218864 | G/A | chr07 | 213,218,864 | N | A | G | A |
| dforc7 | CA10X.chr7__213219006 | A/G | chr07 | 213,219,006 | N | A | G | A |
| dforc7 | CA10X.chr7__213219029 | G/A | chr07 | 213,219,029 | N | A | G | A |
| dforc7 | CA10X.chr7__213220958 | A/G | chr07 | 213,220,958 | A | A | G | A |
| dforc7 | CA10X.chr7__213224773 | A/G | chr07 | 213,224,773 | N | A | G | A |
| dforc7 | CA10X.chr7__213224783 | T/C | chr07 | 213,224,783 | N | C | T | C |
| dforc7 | CA10X.chr7__213230073 | C/T | chr07 | 213,230,073 | T | T | C | T |
| dforc7 | CA10X.chr7__213297211 | C/T | chr07 | 213,297,211 | C | C | T | C |
| dforc7 | CA10X.chr7__213303258 | A/C | chr07 | 213,303,258 | A | A | C | A |
| dforc7 | CA10X.chr7__213317520 | A/G | chr07 | 213,317,520 | N | A | G | A |
| dforc7 | CA10X.chr7__213317762 | G/A | chr07 | 213,317,762 | A | A | G | A |

TABLE 4-continued

| QTL | Marker | alleles | chrom | pos | Garnet | Maor | UCD14 | favorable allele |
|---|---|---|---|---|---|---|---|---|
| dforc7 | CA10X.chr7__213317778 | T/C | chr07 | 213,317,778 | C | C | T | C |
| dforc7 | CA10X.chr7__213397781 | T/C | chr07 | 213,397,781 | C | C | T | C |
| dforc7 | CA10X.chr7__213397782 | G/A | chr07 | 213,397,782 | G | G | A | G |
| dforc7 | CA10X.chr7__213398405 | C/A | chr07 | 213,398,405 | A | A | C | A |
| dforc7 | CA10X.chr7__213398448 | T/G | chr07 | 213,398,448 | T | T | G | T |
| dforc7 | CA10X.chr7__213398552 | G/T | chr07 | 213,398,552 | T | T | G | T |
| dforc7 | CA10X.chr7__213423086 | T/G | chr07 | 213,423,086 | T | T | G | T |
| dforc7 | CA10X.chr7__213441067 | A/G | chr07 | 213,441,067 | A | A | G | A |
| dforc7 | CA10X.chr7__213441284 | T/C | chr07 | 213,441,284 | C | C | T | C |
| dforc7 | CA10X.chr7__213441388 | T/C | chr07 | 213,441,388 | T | T | C | T |
| dforc7 | CA10X.chr7__213441401 | G/A | chr07 | 213,441,401 | G | G | A | G |
| dforc7 | CA10X.chr7__213441821 | T/G | chr07 | 213,441,821 | G | G | T | G |
| dforc7 | CA10X.chr7__213490421 | C/T | chr07 | 213,490,421 | C | C | T | C |
| dforc7 | CA10X.chr7__213490433 | A/G | chr07 | 213,490,433 | A | A | G | A |
| dforc7 | CA10X.chr7__213490486 | C/A | chr07 | 213,490,486 | C | C | A | C |
| dforc7 | CA10X.chr7__213490630 | T/C | chr07 | 213,490,630 | C | C | T | C |
| dforc7 | CA10X.chr7__213494581 | G/T | chr07 | 213,494,581 | G | G | T | G |
| dforc7 | CA10X.chr7__213617178 | G/T | chr07 | 213,617,178 | T | G | T | G |
| dforc7 | CA10X.chr7__213617183 | G/A | chr07 | 213,617,183 | A | G | A | G |
| dforc7 | CA10X.chr7__213617194 | C/T | chr07 | 213,617,194 | T | C | T | C |
| dforc7 | CA10X.chr7__213619943 | G/A | chr07 | 213,619,943 | A | G | A | G |
| dforc7 | CA10X.chr7__213619987 | A/G | chr07 | 213,619,987 | A | G | A | G |
| dforc7 | CA10X.chr7__213620572 | C/T | chr07 | 213,620,572 | C | T | C | T |
| dforc7 | CA10X.chr7__213620595 | A/G | chr07 | 213,620,595 | A | G | A | G |
| dforc7 | CA10X.chr7__213622028 | T/C | chr07 | 213,622,028 | C | T | C | T |
| dforc7 | CA10X.chr7__213622437 | G/A | chr07 | 213,622,437 | G | A | G | A |
| dforc7 | CA10X.chr7__213622600 | G/T | chr07 | 213,622,600 | G | T | G | T |
| dforc7 | CA10X.chr7__213623832 | G/A | chr07 | 213,623,832 | A | G | A | G |
| dforc7 | CA10X.chr7__213658461 | A/G | chr07 | 213,658,461 | G | A | G | A |
| dforc7 | CA10X.chr7__213658473 | G/A | chr07 | 213,658,473 | A | G | A | G |
| dforc7 | CA10X.chr7__213658582 | T/C | chr07 | 213,658,582 | C | T | C | T |
| dforc7 | CA10X.chr7__213687431 | C/T | chr07 | 213,687,431 | T | C | T | C |
| dforc7 | CA10X.chr7__213687552 | T/C | chr07 | 213,687,552 | T | C | T | C |
| dforc7 | CA10X.chr7__213687595 | T/C | chr07 | 213,687,595 | C | T | C | T |
| dforc7 | CA10X.chr7__213688214 | A/C | chr07 | 213,688,214 | A | C | A | C |
| dforc7 | CA10X.chr7__213688218 | A/C | chr07 | 213,688,218 | A | C | A | C |
| dforc7 | CA10X.chr7__213688221 | A/C | chr07 | 213,688,221 | A | C | A | C |
| dforc7 | CA10X.chr7__213688224 | A/G | chr07 | 213,688,224 | A | G | A | G |
| dforc7 | CA10X.chr7__213688229 | T/G | chr07 | 213,688,229 | T | G | T | G |
| dforc7 | CA10X.chr7__213688230 | G/C | chr07 | 213,688,230 | C | G | C | G |
| dforc7 | CA10X.chr7__213688232 | T/A | chr07 | 213,688,232 | T | A | T | A |
| dforc7 | CA10X.chr7__213695621 | C/T | chr07 | 213,695,621 | T | C | T | C |
| dforc7 | CA10X.chr7__213695705 | C/T | chr07 | 213,695,705 | T | C | T | C |
| dforc7 | CA10X.chr7__213702183 | A/G | chr07 | 213,702,183 | N | A | G | A |
| dforc7 | CA10X.chr7__213702286 | T/C | chr07 | 213,702,286 | N | C | T | C |
| dforc7 | CA10X.chr7__213702308 | A/G | chr07 | 213,702,308 | N | G | A | G |
| dforc7 | CA10X.chr7__213734311 | A/G | chr07 | 213,734,311 | A | G | A | G |
| dforc7 | CA10X.chr7__213820872 | C/T | chr07 | 213,820,872 | C | T | C | T |
| dforc7 | CA10X.chr7__213836837 | G/C | chr07 | 213,836,837 | C | G | C | G |
| dforc7 | CA10X.chr7__213836849 | T/C | chr07 | 213,836,849 | T | C | T | C |
| dforc7 | CA10X.chr7__213836962 | T/C | chr07 | 213,836,962 | C | T | C | T |
| dforc7 | CA10X.chr7__213836969 | A/G | chr07 | 213,836,969 | A | G | A | G |
| dforc7 | CA10X.chr7__214386513 | G/A | chr07 | 214,386,513 | A | G | A | G |
| dforc7 | CA10X.chr7__214524922 | T/C | chr07 | 214,524,922 | T | C | T | C |
| dforc7 | CA10X.chr7__214525039 | A/C | chr07 | 214,525,039 | C | A | C | A |
| dforc7 | CA10X.chr7__214525151 | G/A | chr07 | 214,525,151 | G | A | G | A |
| dforc7 | CA10X.chr7__214525171 | G/A | chr07 | 214,525,171 | A | G | A | G |
| dforc7 | CA10X.chr7__214667650 | C/A | chr07 | 214,667,650 | N | A | C | A |
| dforc7 | CA10X.chr7__214667724 | T/G | chr07 | 214,667,724 | N | G | T | G |
| dforc7 | CA10X.chr7__214667732 | G/A | chr07 | 214,667,732 | N | G | A | G |
| dforc7 | CA10X.chr7__214667733 | A/G | chr07 | 214,667,733 | N | A | G | A |
| dforc7 | CA10X.chr7__214667761 | T/C | chr07 | 214,667,761 | C | T | C | T |
| dforc7 | CA10X.chr7__214667798 | G/A | chr07 | 214,667,798 | N | A | G | A |
| dforc7 | CA10X.chr7__214667845 | T/A | chr07 | 214,667,845 | N | T | A | T |
| dforc7 | CA10X.chr7__214681838 | C/G | chr07 | 214,681,838 | G | C | G | C |
| dforc7 | CA10X.chr7__214681848 | A/G | chr07 | 214,681,848 | G | A | G | A |
| dforc7 | CA10X.chr7__214681863 | G/T | chr07 | 214,681,863 | T | G | T | G |
| dforc7 | CA10X.chr7__214681878 | G/A | chr07 | 214,681,878 | A | G | A | G |
| dforc7 | CA10X.chr7__214703508 | C/T | chr07 | 214,703,508 | T | C | T | C |
| dforc7 | CA10X.chr7__214703513 | C/T | chr07 | 214,703,513 | C | C | T | C |
| dforc7 | CA10X.chr7__214703517 | G/A | chr07 | 214,703,517 | G | G | A | G |
| dforc7 | CA10X.chr7__214708140 | C/A | chr07 | 214,708,140 | C | A | C | A |
| dforc7 | CA10X.chr7__214779876 | C/G | chr07 | 214,779,876 | C | G | C | G |
| dforc7 | CA10X.chr7__214779916 | A/G | chr07 | 214,779,916 | G | A | G | A |
| dforc7 | CA10X.chr7__214779946 | G/A | chr07 | 214,779,946 | A | G | A | G |
| dforc7 | CA10X.chr7__214779954 | A/G | chr07 | 214,779,954 | G | A | G | A |
| dforc7 | CA10X.chr7__214793109 | G/T | chr07 | 214,793,109 | G | T | G | T |

TABLE 4-continued

| QTL | Marker | alleles | chrom | pos | Garnet | Maor | UCD14 | favorable allele |
|---|---|---|---|---|---|---|---|---|
| dforc7 | CA10X.chr7__214803484 | A/C | chr07 | 214,803,484 | A | C | A | C |
| dforc7 | CA10X.chr7__214803528 | C/A | chr07 | 214,803,528 | A | C | A | C |
| dforc7 | CA10X.chr7__214803556 | T/G | chr07 | 214,803,556 | G | T | G | T |
| dforc7 | CA10X.chr7__215043990 | C/T | chr07 | 215,043,990 | C | T | C | T |
| dforc7 | CA10X.chr7__215044166 | G/A | chr07 | 215,044,166 | G | A | G | A |
| dforc7 | CA10X.chr7__215047079 | T/G | chr07 | 215,047,079 | T | G | T | G |
| dforc7 | CA10X.chr7__215047114 | T/C | chr07 | 215,047,114 | T | C | T | C |
| dforc7 | CA10X.chr7__215047171 | G/T | chr07 | 215,047,171 | G | T | G | T |
| dforc7 | CA10X.chr7__215047176 | A/T | chr07 | 215,047,176 | A | T | A | T |
| dforc7 | CA10X.chr7__215047201 | C/T | chr07 | 215,047,201 | C | T | C | T |
| dforc7 | CA10X.chr7__215050691 | A/T | chr07 | 215,050,691 | N | T | A | T |
| dforc7 | CA10X.chr7__215050863 | A/G | chr07 | 215,050,863 | N | A | G | A |
| dforc7 | CA10X.chr7__215104170 | G/C | chr07 | 215,104,170 | G | C | G | C |
| dforc7 | CA10X.chr7__215104208 | A/C | chr07 | 215,104,208 | C | A | C | A |
| dforc7 | CA10X.chr7__215114753 | T/C | chr07 | 215,114,753 | T | C | T | C |
| dforc7 | CA10X.chr7__215123208 | A/C | chr07 | 215,123,208 | A | C | A | C |
| dforc7 | CA10X.chr7__215132771 | C/T | chr07 | 215,132,771 | T | C | T | C |
| dforc7 | CA10X.chr7__215132823 | C/T | chr07 | 215,132,823 | C | T | C | T |
| dforc7 | CA10X.chr7__215132841 | T/C | chr07 | 215,132,841 | C | T | C | T |
| dforc7 | CA10X.chr7__215175037 | T/C | chr07 | 215,175,037 | C | T | C | T |
| dforc7 | CA10X.chr7__215723464 | A/G | chr07 | 215,723,464 | A | A | G | A |
| dforc7 | CA10X.chr7__215761218 | C/T | chr07 | 215,761,218 | C | T | C | T |
| dforc7 | CA10X.chr7__216426421 | A/T | chr07 | 216,426,421 | A | T | A | T |
| dforc7 | CA10X.chr7__216504965 | A/C | chr07 | 216,504,965 | A | A | C | A |
| dforc7 | CA10X.chr7__216529047 | G/A | chr07 | 216,529,047 | G | A | G | A |
| dforc7 | CA10X.chr7__216529230 | A/G | chr07 | 216,529,230 | G | A | G | A |
| dforc7 | CA10X.chr7__216529744 | G/T | chr07 | 216,529,744 | N | G | T | G |
| dforc7 | CA10X.chr7__216529749 | T/G | chr07 | 216,529,749 | N | G | T | G |
| dforc7 | CA10X.chr7__216529825 | A/C | chr07 | 216,529,825 | N | A | C | A |
| dforc7 | CA10X.chr7__216530965 | T/A | chr07 | 216,530,965 | A | T | A | T |
| dforc7 | CA10X.chr7__216531027 | A/T | chr07 | 216,531,027 | T | A | T | A |
| dforc7 | CA10X.chr7__216531042 | A/G | chr07 | 216,531,042 | A | G | A | G |
| dforc7 | CA10X.chr7__216531060 | T/C | chr07 | 216,531,060 | C | T | C | T |
| dforc7 | CA10X.chr7__216531254 | G/A | chr07 | 216,531,254 | A | G | A | G |
| dforc7 | CA10X.chr7__216532218 | T/C | chr07 | 216,532,218 | N | T | C | T |
| dforc7 | CA10X.chr7__216532279 | C/T | chr07 | 216,532,279 | N | T | C | T |
| dforc7 | CA10X.chr7__216542815 | A/G | chr07 | 216,542,815 | A | G | A | G |
| dforc7 | CA10X.chr7__216545510 | G/T | chr07 | 216,545,510 | G | T | G | T |
| dforc7 | CA10X.chr7__216545515 | T/C | chr07 | 216,545,515 | C | T | C | T |
| dforc7 | CA10X.chr7__216577055 | G/C | chr07 | 216,577,055 | N | G | C | G |
| dforc7 | CA10X.chr7__216762432 | G/T | chr07 | 216,762,432 | T | T | G | T |
| dforc7 | CA10X.chr7__216776914 | A/C | chr07 | 216,776,914 | C | C | A | C |
| dforc7 | CA10X.chr7__216777064 | G/A | chr07 | 216,777,064 | A | A | G | A |
| dforc7 | CA10X.chr7__216785454 | T/C | chr07 | 216,785,454 | C | C | T | C |
| dforc7 | CA10X.chr7__216803713 | T/G | chr07 | 216,803,713 | N | T | G | T |
| dforc7 | CA10X.chr7__216803776 | T/C | chr07 | 216,803,776 | N | C | T | C |
| dforc7 | CA10X.chr7__216803808 | A/C | chr07 | 216,803,808 | N | A | C | A |
| dforc7 | CA10X.chr7__216909260 | A/G | chr07 | 216,909,260 | G | A | G | A |
| dforc7 | CA10X.chr7__216909272 | C/T | chr07 | 216,909,272 | C | T | C | T |
| dforc7 | CA10X.chr7__216909276 | T/A | chr07 | 216,909,276 | A | T | A | T |
| dforc7 | CA10X.chr7__216909369 | G/A | chr07 | 216,909,369 | G | A | G | A |
| dforc7 | CA10X.chr7__216909397 | C/T | chr07 | 216,909,397 | C | T | C | T |
| dforc7 | CA10X.chr7__216942827 | G/A | chr07 | 216,942,827 | A | G | A | G |
| dforc7 | CA10X.chr7__216944388 | G/A | chr07 | 216,944,388 | A | G | A | G |
| dforc7 | CA10X.chr7__216959961 | C/T | chr07 | 216,959,961 | C | T | C | T |
| dforc7 | CA10X.chr7__216990198 | T/A | chr07 | 216,990,198 | T | A | T | A |
| dfreq4 | CA10X.chr4__11753151 | C/T | chr04 | 11,753,151 | T | T | C | C |
| dfreq4 | CA10X.chr4__12039384 | G/A | chr04 | 12,039,384 | G | G | A | A |
| dfreq4 | CA10X.chr4__12354871 | G/T | chr04 | 12,354,871 | T | T | G | G |
| dfreq4 | CA10X.chr4__12355123 | T/G | chr04 | 12,355,123 | T | T | G | G |
| dfreq4 | CA10X.chr4__12359518 | A/C | chr04 | 12,359,518 | C | C | A | A |
| dfreq4 | CA10X.chr4__12367059 | G/A | chr04 | 12,367,059 | A | A | G | G |
| dfreq4 | CA10X.chr4__12382987 | G/A | chr04 | 12,382,987 | G | G | A | A |
| dfreq4 | CA10X.chr4__12494447 | G/T | chr04 | 12,494,447 | T | T | G | G |
| dfreq4 | CA10X.chr4__12528284 | T/G | chr04 | 12,528,284 | T | T | G | G |
| dfreq4 | CA10X.chr4__12537119 | T/C | chr04 | 12,537,119 | C | C | T | T |
| dfreq4 | CA10X.chr4__12537378 | A/G | chr04 | 12,537,378 | G | G | A | A |
| dfreq4 | CA10X.chr4__12537423 | A/G | chr04 | 12,537,423 | G | G | A | A |
| dfreq4 | CA10X.chr4__12538244 | A/G | chr04 | 12,538,244 | A | A | G | G |
| dfreq4 | CA10X.chr4__12538262 | G/A | chr04 | 12,538,262 | G | G | A | A |
| dfreq4 | CA10X.chr4__12538435 | C/T | chr04 | 12,538,435 | C | C | T | T |
| dfreq4 | CA10X.chr4__12541037 | G/A | chr04 | 12,541,037 | A | A | G | G |
| dfreq4 | CA10X.chr4__12541241 | A/C | chr04 | 12,541,241 | C | C | A | A |
| dfreq4 | CA10X.chr4__12541251 | A/G | chr04 | 12,541,251 | A | A | G | G |
| dfreq4 | CA10X.chr4__12542739 | A/G | chr04 | 12,542,739 | A | A | G | G |
| dfreq4 | CA10X.chr4__12542745 | A/G | chr04 | 12,542,745 | G | G | A | A |
| dfreq4 | CA10X.chr4__12542755 | T/C | chr04 | 12,542,755 | T | T | C | C |

TABLE 4-continued

| QTL | Marker | alleles | chrom | pos | Garnet | Maor | UCD14 | favorable allele |
|---|---|---|---|---|---|---|---|---|
| dfreq4 | CA10X.chr4__12544493 | G/T | chr04 | 12,544,493 | T | T | G | G |
| dfreq4 | CA10X.chr4__12544578 | G/A | chr04 | 12,544,578 | G | G | A | A |
| dfreq4 | CA10X.chr4__12624912 | G/T | chr04 | 12,624,912 | G | G | T | T |
| dfreq4 | CA10X.chr4__12624938 | C/A | chr04 | 12,624,938 | A | A | C | C |
| dfreq4 | CA10X.chr4__13037239 | T/A | chr04 | 13,037,239 | T | T | A | A |
| dfreq4 | CA10X.chr4__13037267 | C/A | chr04 | 13,037,267 | C | C | A | A |
| dfreq4 | CA10X.chr4__13264064 | G/A | chr04 | 13,264,064 | G | G | A | A |
| dfreq4 | CA10X.chr4__13264078 | A/G | chr04 | 13,264,078 | A | A | G | G |
| dfreq4 | CA10X.chr4__13264123 | G/C | chr04 | 13,264,123 | G | G | C | C |
| dfreq4 | CA10X.chr4__13264144 | T/C | chr04 | 13,264,144 | T | T | C | C |
| dfreq4 | CA10X.chr4__13399872 | A/G | chr04 | 13,399,872 | A | A | G | G |
| dfreq4 | CA10X.chr4__13399882 | G/A | chr04 | 13,399,882 | A | A | G | G |
| dfreq4 | CA10X.chr4__13399919 | A/G | chr04 | 13,399,919 | A | A | G | G |
| dfreq4 | CA10X.chr4__13403024 | G/A | chr04 | 13,403,024 | G | G | A | A |
| dfreq10 | CA10X.chr10__156062352 | A/C | chr10 | 156,062,352 | A | A | C | C |
| dfreq10 | CA10X.chr10__156067302 | G/A | chr10 | 156,067,302 | G | G | A | A |
| dfreq10 | CA10X.chr10__156067408 | T/C | chr10 | 156,067,408 | C | C | T | T |
| dfreq10 | CA10X.chr10__156068372 | T/C | chr10 | 156,068,372 | C | C | T | T |
| dfreq10 | CA10X.chr10__156105534 | G/A | chr10 | 156,105,534 | A | A | G | G |
| dfreq10 | CA10X.chr10__156119248 | A/G | chr10 | 156,119,248 | A | A | G | G |
| dfreq10 | CA10X.chr10__156137730 | T/C | chr10 | 156,137,730 | C | C | T | T |
| dfreq10 | CA10X.chr10__156141244 | A/G | chr10 | 156,141,244 | A | A | G | G |
| dfreq10 | CA10X.chr10__156141338 | G/A | chr10 | 156,141,338 | G | G | A | A |
| dfreq10 | CA10X.chr10__156141435 | G/A | chr10 | 156,141,435 | G | G | A | A |
| dfreq10 | CA10X.chr10__156141459 | G/A | chr10 | 156,141,459 | A | A | G | G |
| dfreq10 | CA10X.chr10__156141517 | T/C | chr10 | 156,141,517 | T | T | C | C |
| dfreq10 | CA10X.chr10__156141536 | A/G | chr10 | 156,141,536 | A | A | G | G |
| dfreq10 | CA10X.chr10__156141660 | A/G | chr10 | 156,141,660 | G | G | A | A |
| dfreq10 | CA10X.chr10__156145742 | A/G | chr10 | 156,145,742 | G | G | A | A |
| dfreq10 | CA10X.chr10__156153036 | A/G | chr10 | 156,153,036 | G | G | A | A |
| dfreq10 | CA10X.chr10__156171583 | C/G | chr10 | 156,171,583 | C | C | G | G |
| dfreq10 | CA10X.chr10__156195807 | C/A | chr10 | 156,195,807 | C | C | A | A |
| dfreq10 | CA10X.chr10__156210420 | A/G | chr10 | 156,210,420 | A | A | G | G |
| dfreq10 | CA10X.chr10__156217703 | C/T | chr10 | 156,217,703 | C | C | T | T |
| dfreq10 | CA10X.chr10__156224769 | G/A | chr10 | 156,224,769 | A | A | G | G |
| dfreq10 | CA10X.chr10__156228616 | A/G | chr10 | 156,228,616 | G | G | A | A |
| dfreq10 | CA10X.chr10__156235039 | T/C | chr10 | 156,235,039 | C | C | T | T |
| dfreq10 | CA10X.chr10__156253401 | A/G | chr10 | 156,253,401 | A | A | G | G |
| dfreq10 | CA10X.chr10__156253464 | C/T | chr10 | 156,253,464 | T | T | C | C |
| dfreq10 | CA10X.chr10__156253536 | A/G | chr10 | 156,253,536 | A | A | G | G |
| dfreq10 | CA10X.chr10__156257424 | A/C | chr10 | 156,257,424 | A | A | C | C |
| dfreq10 | CA10X.chr10__156257672 | G/A | chr10 | 156,257,672 | G | G | A | A |
| dfreq10 | CA10X.chr10__156257708 | T/C | chr10 | 156,257,708 | C | C | T | T |
| dfreq10 | CA10X.chr10__156257734 | C/T | chr10 | 156,257,734 | T | T | C | C |
| dfreq10 | CA10X.chr10__156257812 | A/G | chr10 | 156,257,812 | A | A | G | G |
| dfreq10 | CA10X.chr10__156257854 | A/G | chr10 | 156,257,854 | G | G | A | A |
| dfreq10 | CA10X.chr10__156264340 | C/T | chr10 | 156,264,340 | C | C | T | T |
| dfreq10 | CA10X.chr10__156264560 | G/A | chr10 | 156,264,560 | G | G | A | A |
| dfreq10 | CA10X.chr10__156264618 | T/C | chr10 | 156,264,618 | T | T | C | C |
| dfreq10 | CA10X.chr10__156264620 | T/G | chr10 | 156,264,620 | G | G | T | T |
| dfreq10 | CA10X.chr10__156277975 | G/T | chr10 | 156,277,975 | G | G | T | T |
| dfreq10 | CA10X.chr10__156277994 | G/A | chr10 | 156,277,994 | G | G | A | A |
| dfreq10 | CA10X.chr10__156280487 | G/A | chr10 | 156,280,487 | G | G | A | A |
| dfreq10 | CA10X.chr10__156280502 | T/C | chr10 | 156,280,502 | T | T | C | C |
| dfreq10 | CA10X.chr10__156282448 | C/T | chr10 | 156,282,448 | C | C | T | T |
| dfreq10 | CA10X.chr10__156282528 | T/C | chr10 | 156,282,528 | T | T | C | C |
| dfreq10 | CA10X.chr10__156285407 | G/A | chr10 | 156,285,407 | A | A | G | G |
| dfreq10 | CA10X.chr10__156285485 | T/G | chr10 | 156,285,485 | T | T | G | G |
| dfreq10 | CA10X.chr10__156290790 | C/T | chr10 | 156,290,790 | C | C | T | T |
| dfreq10 | CA10X.chr10__156290828 | C/T | chr10 | 156,290,828 | C | C | T | T |
| dfreq10 | CA10X.chr10__156308038 | A/G | chr10 | 156,308,038 | A | A | G | G |
| dfreq10 | CA10X.chr10__156308133 | T/C | chr10 | 156,308,133 | T | T | C | C |
| dfreq10 | CA10X.chr10__156308171 | C/T | chr10 | 156,308,171 | T | T | C | C |
| dfreq10 | CA10X.chr10__156308239 | C/T | chr10 | 156,308,239 | C | C | T | T |
| dfreq10 | CA10X.chr10__156402103 | C/A | chr10 | 156,402,103 | C | C | A | A |
| dfreq10 | CA10X.chr10__156426013 | T/G | chr10 | 156,426,013 | T | T | G | G |
| dfreq10 | CA10X.chr10__156586673 | A/G | chr10 | 156,586,673 | G | G | A | A |
| dfreq10 | CA10X.chr10__156949128 | T/C | chr10 | 156,949,128 | C | C | T | T |
| dfreq10 | CA10X.chr10__157999874 | C/A | chr10 | 157,999,874 | C | C | A | A |
| dfreq10 | CA10X.chr10__159934779 | C/A | chr10 | 159,934,779 | C | C | A | A |
| dfreq10 | CA10X.chr10__160043878 | T/G | chr10 | 160,043,878 | G | G | T | T |
| dfreq10 | CA10X.chr10__160202582 | G/T | chr10 | 160,202,582 | G | G | T | T |
| dfreq10 | CA10X.chr10__161306031 | T/C | chr10 | 161,306,031 | C | C | T | T |
| dfreq10 | CA10X.chr10__161526273 | C/A | chr10 | 161,526,273 | C | C | A | A |
| dfreq10 | CA10X.chr10__162335900 | C/T | chr10 | 162,335,900 | T | T | C | C |
| dfreq10 | CA10X.chr10__162336111 | A/G | chr10 | 162,336,111 | G | G | A | A |
| dfreq10 | CA10X.chr10__162336124 | G/A | chr10 | 162,336,124 | A | A | G | G |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10__162339027 | T/C | chr10 | 162,339,027 | T | T | C | C |
| dfreq10 | CA10X.chr10__162341547 | G/A | chr10 | 162,341,547 | G | G | A | A |
| dfreq10 | CA10X.chr10__162341612 | C/T | chr10 | 162,341,612 | C | C | T | T |
| dfreq10 | CA10X.chr10__162384037 | C/T | chr10 | 162,384,037 | C | C | T | T |
| dfreq10 | CA10X.chr10__162384093 | A/G | chr10 | 162,384,093 | A | A | G | G |
| dfreq10 | CA10X.chr10__162384393 | T/A | chr10 | 162,384,393 | T | T | A | A |
| dfreq10 | CA10X.chr10__162384418 | C/T | chr10 | 162,384,418 | T | T | C | C |
| dfreq10 | CA10X.chr10__162444498 | A/G | chr10 | 162,444,498 | A | A | G | G |
| dfreq10 | CA10X.chr10__162447148 | T/C | chr10 | 162,447,148 | C | C | T | T |
| dfreq10 | CA10X.chr10__162447179 | G/A | chr10 | 162,447,179 | G | G | A | A |
| dfreq10 | CA10X.chr10__162447180 | G/T | chr10 | 162,447,180 | T | T | G | G |
| dfreq10 | CA10X.chr10__162482888 | C/T | chr10 | 162,482,888 | C | C | T | T |
| dfreq10 | CA10X.chr10__162503535 | C/T | chr10 | 162,503,535 | T | T | C | C |
| dfreq10 | CA10X.chr10__162507008 | G/A | chr10 | 162,507,008 | A | A | G | G |
| dfreq10 | CA10X.chr10__162507066 | T/C | chr10 | 162,507,066 | C | C | T | T |
| dfreq10 | CA10X.chr10__162557111 | C/T | chr10 | 162,557,111 | C | C | T | T |
| dfreq10 | CA10X.chr10__162557159 | A/G | chr10 | 162,557,159 | G | G | A | A |
| dfreq10 | CA10X.chr10__162564940 | A/G | chr10 | 162,564,940 | G | G | A | A |
| dfreq10 | CA10X.chr10__162564943 | T/C | chr10 | 162,564,943 | C | C | T | T |
| dfreq10 | CA10X.chr10__162593708 | T/C | chr10 | 162,593,708 | C | C | T | T |
| dfreq10 | CA10X.chr10__162595712 | G/C | chr10 | 162,595,712 | G | G | C | C |
| dfreq10 | CA10X.chr10__162610407 | C/T | chr10 | 162,610,407 | C | C | T | T |
| dfreq10 | CA10X.chr10__162610550 | T/C | chr10 | 162,610,550 | C | C | T | T |
| dfreq10 | CA10X.chr10__162642844 | C/T | chr10 | 162,642,844 | C | C | T | T |
| dfreq10 | CA10X.chr10__162670064 | C/T | chr10 | 162,670,064 | C | C | T | T |
| dfreq10 | CA10X.chr10__162720736 | G/A | chr10 | 162,720,736 | G | G | A | A |
| dfreq10 | CA10X.chr10__162730549 | T/G | chr10 | 162,730,549 | T | T | G | G |
| dfreq10 | CA10X.chr10__162730551 | T/A | chr10 | 162,730,551 | T | T | A | A |
| dfreq10 | CA10X.chr10__162730601 | G/C | chr10 | 162,730,601 | C | C | G | G |
| dfreq10 | CA10X.chr10__162739494 | A/C | chr10 | 162,739,494 | C | C | A | A |
| dfreq10 | CA10X.chr10__162739547 | T/C | chr10 | 162,739,547 | T | T | C | C |
| dfreq10 | CA10X.chr10__162755757 | A/G | chr10 | 162,755,757 | G | G | A | A |
| dfreq10 | CA10X.chr10__162755877 | C/T | chr10 | 162,755,877 | C | C | T | T |
| dfreq10 | CA10X.chr10__162761278 | T/C | chr10 | 162,761,278 | C | C | T | T |
| dfreq10 | CA10X.chr10__162794927 | C/T | chr10 | 162,794,927 | C | C | T | T |
| dfreq10 | CA10X.chr10__162794961 | C/G | chr10 | 162,794,961 | G | G | C | C |
| dfreq10 | CA10X.chr10__162794975 | G/A | chr10 | 162,794,975 | A | A | G | G |
| dfreq10 | CA10X.chr10__162801344 | T/C | chr10 | 162,801,344 | T | T | C | C |
| dfreq10 | CA10X.chr10__162802265 | A/T | chr10 | 162,802,265 | A | A | T | T |
| dfreq10 | CA10X.chr10__162824865 | T/G | chr10 | 162,824,865 | T | T | G | G |
| dfreq10 | CA10X.chr10__162824964 | C/T | chr10 | 162,824,964 | C | C | T | T |
| dfreq10 | CA10X.chr10__162826357 | T/A | chr10 | 162,826,357 | T | T | A | A |
| dfreq10 | CA10X.chr10__162829605 | C/T | chr10 | 162,829,605 | C | C | T | T |
| dfreq10 | CA10X.chr10__162829608 | A/G | chr10 | 162,829,608 | A | A | G | G |
| dfreq10 | CA10X.chr10__162829646 | G/A | chr10 | 162,829,646 | G | G | A | A |
| dfreq10 | CA10X.chr10__162832370 | A/G | chr10 | 162,832,370 | G | G | A | A |
| dfreq10 | CA10X.chr10__162832633 | T/C | chr10 | 162,832,633 | C | C | T | T |
| dfreq10 | CA10X.chr10__162845431 | T/C | chr10 | 162,845,431 | T | T | C | C |
| dfreq10 | CA10X.chr10__162845442 | T/C | chr10 | 162,845,442 | C | C | T | T |
| dfreq10 | CA10X.chr10__162848705 | G/A | chr10 | 162,848,705 | A | A | G | G |
| dfreq10 | CA10X.chr10__162853210 | C/A | chr10 | 162,853,210 | C | C | A | A |
| dfreq10 | CA10X.chr10__162853228 | T/C | chr10 | 162,853,228 | C | C | T | T |
| dfreq10 | CA10X.chr10__162854551 | A/G | chr10 | 162,854,551 | A | A | G | G |
| dfreq10 | CA10X.chr10__162854578 | C/T | chr10 | 162,854,578 | T | T | C | C |
| dfreq10 | CA10X.chr10__162854583 | T/C | chr10 | 162,854,583 | C | C | T | T |
| dfreq10 | CA10X.chr10__162854727 | A/G | chr10 | 162,854,727 | G | G | A | A |
| dfreq10 | CA10X.chr10__162854738 | A/G | chr10 | 162,854,738 | G | G | A | A |
| dfreq10 | CA10X.chr10__162861230 | A/G | chr10 | 162,861,230 | G | G | A | A |
| dfreq10 | CA10X.chr10__162861281 | A/G | chr10 | 162,861,281 | G | G | A | A |
| dfreq10 | CA10X.chr10__162892825 | T/A | chr10 | 162,892,825 | A | A | T | T |
| dfreq10 | CA10X.chr10__162892924 | A/T | chr10 | 162,892,924 | A | A | T | T |
| dfreq10 | CA10X.chr10__162908244 | T/C | chr10 | 162,908,244 | T | T | C | C |
| dfreq10 | CA10X.chr10__162908265 | G/A | chr10 | 162,908,265 | G | G | A | A |
| dfreq10 | CA10X.chr10__162908308 | G/A | chr10 | 162,908,308 | A | A | G | G |
| dfreq10 | CA10X.chr10__162918661 | G/A | chr10 | 162,918,661 | G | G | A | A |
| dfreq10 | CA10X.chr10__162918674 | T/A | chr10 | 162,918,674 | A | A | T | T |
| dfreq10 | CA10X.chr10__162918719 | C/A | chr10 | 162,918,719 | C | C | A | A |
| dfreq10 | CA10X.chr10__162922347 | T/A | chr10 | 162,922,347 | A | A | T | T |
| dfreq10 | CA10X.chr10__162926065 | A/G | chr10 | 162,926,065 | A | A | G | G |
| dfreq10 | CA10X.chr10__162928224 | C/T | chr10 | 162,928,224 | C | C | T | T |
| dfreq10 | CA10X.chr10__162931845 | C/T | chr10 | 162,931,845 | C | C | T | T |
| dfreq10 | CA10X.chr10__162933578 | A/G | chr10 | 162,933,578 | G | G | A | A |
| dfreq10 | CA10X.chr10__162933630 | T/C | chr10 | 162,933,630 | T | T | C | C |
| dfreq10 | CA10X.chr10__162933697 | G/T | chr10 | 162,933,697 | T | T | G | G |
| dfreq10 | CA10X.chr10__162933718 | A/G | chr10 | 162,933,718 | A | A | G | G |
| dfreq10 | CA10X.chr10__162934655 | G/T | chr10 | 162,934,655 | G | G | T | T |
| dfreq10 | CA10X.chr10__162960292 | C/T | chr10 | 162,960,292 | C | C | T | T |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10_162996136 | G/A | chr10 | 162,996,136 | A | A | G | G |
| dfreq10 | CA10X.chr10_162996141 | T/C | chr10 | 162,996,141 | T | T | C | C |
| dfreq10 | CA10X.chr10_162996158 | A/C | chr10 | 162,996,158 | C | C | A | A |
| dfreq10 | CA10X.chr10_162996162 | G/T | chr10 | 162,996,162 | T | T | G | G |
| dfreq10 | CA10X.chr10_162996323 | A/G | chr10 | 162,996,323 | A | A | G | G |
| dfreq10 | CA10X.chr10_162996372 | G/A | chr10 | 162,996,372 | G | G | A | A |
| dfreq10 | CA10X.chr10_162996427 | C/T | chr10 | 162,996,427 | T | T | C | C |
| dfreq10 | CA10X.chr10_163004348 | A/G | chr10 | 163,004,348 | G | G | A | A |
| dfreq10 | CA10X.chr10_163004364 | T/C | chr10 | 163,004,364 | T | T | C | C |
| dfreq10 | CA10X.chr10_163004370 | T/G | chr10 | 163,004,370 | G | G | T | T |
| dfreq10 | CA10X.chr10_163004460 | T/A | chr10 | 163,004,460 | A | A | T | T |
| dfreq10 | CA10X.chr10_163019471 | G/A | chr10 | 163,019,471 | A | A | G | G |
| dfreq10 | CA10X.chr10_163019533 | G/C | chr10 | 163,019,533 | G | G | C | C |
| dfreq10 | CA10X.chr10_163019616 | A/C | chr10 | 163,019,616 | A | A | C | C |
| dfreq10 | CA10X.chr10_163019763 | A/C | chr10 | 163,019,763 | A | A | C | C |
| dfreq10 | CA10X.chr10_163021708 | C/A | chr10 | 163,021,708 | A | A | C | C |
| dfreq10 | CA10X.chr10_163182596 | C/T | chr10 | 163,182,596 | C | C | T | T |
| dfreq10 | CA10X.chr10_164002217 | A/G | chr10 | 164,002,217 | G | G | A | A |
| dfreq10 | CA10X.chr10_164002243 | C/T | chr10 | 164,002,243 | C | C | T | T |
| dfreq10 | CA10X.chr10_164002262 | G/T | chr10 | 164,002,262 | T | T | G | G |
| dfreq10 | CA10X.chr10_164006069 | C/T | chr10 | 164,006,069 | C | C | T | T |
| dfreq10 | CA10X.chr10_164006718 | A/C | chr10 | 164,006,718 | C | C | A | A |
| dfreq10 | CA10X.chr10_164009407 | A/C | chr10 | 164,009,407 | C | C | A | A |
| dfreq10 | CA10X.chr10_164010014 | T/G | chr10 | 164,010,014 | T | T | G | G |
| dfreq10 | CA10X.chr10_164010028 | T/C | chr10 | 164,010,028 | C | C | T | T |
| dfreq10 | CA10X.chr10_169743726 | A/G | chr10 | 169,743,726 | G | G | A | A |
| dfreq10 | CA10X.chr10_169743747 | A/G | chr10 | 169,743,747 | G | G | A | A |
| dfreq10 | CA10X.chr10_169743761 | C/T | chr10 | 169,743,761 | T | T | C | C |
| dfreq10 | CA10X.chr10_169743768 | T/C | chr10 | 169,743,768 | T | T | C | C |
| dfreq10 | CA10X.chr10_169743771 | A/G | chr10 | 169,743,771 | G | G | A | A |
| dfreq10 | CA10X.chr10_169744755 | G/C | chr10 | 169,744,755 | C | C | G | G |
| dfreq10 | CA10X.chr10_169744775 | C/A | chr10 | 169,744,775 | C | C | A | A |
| dfreq10 | CA10X.chr10_169744829 | T/C | chr10 | 169,744,829 | T | T | C | C |
| dfreq10 | CA10X.chr10_169744879 | T/G | chr10 | 169,744,879 | T | T | G | G |
| dfreq10 | CA10X.chr10_169744908 | C/T | chr10 | 169,744,908 | C | C | T | T |
| dfreq10 | CA10X.chr10_169744912 | C/A | chr10 | 169,744,912 | C | C | A | A |
| dfreq10 | CA10X.chr10_169758616 | T/C | chr10 | 169,758,616 | T | T | C | C |
| dfreq10 | CA10X.chr10_169761405 | A/G | chr10 | 169,761,405 | G | G | A | A |
| dfreq10 | CA10X.chr10_169778176 | C/A | chr10 | 169,778,176 | C | C | A | A |
| dfreq10 | CA10X.chr10_169778236 | C/T | chr10 | 169,778,236 | T | T | C | C |
| dfreq10 | CA10X.chr10_169784358 | G/A | chr10 | 169,784,358 | G | G | A | A |
| dfreq10 | CA10X.chr10_169785060 | A/G | chr10 | 169,785,060 | A | A | G | G |
| dfreq10 | CA10X.chr10_170432724 | A/G | chr10 | 170,432,724 | A | A | G | G |
| dfreq10 | CA10X.chr10_170432772 | C/T | chr10 | 170,432,772 | C | C | T | T |
| dfreq10 | CA10X.chr10_170462828 | C/T | chr10 | 170,462,828 | C | C | T | T |
| dfreq10 | CA10X.chr10_170462829 | T/C | chr10 | 170,462,829 | C | C | T | T |
| dfreq10 | CA10X.chr10_170480936 | G/A | chr10 | 170,480,936 | A | A | G | G |
| dfreq10 | CA10X.chr10_170482404 | C/T | chr10 | 170,482,404 | C | C | T | T |
| dfreq10 | CA10X.chr10_170487078 | G/A | chr10 | 170,487,078 | A | A | G | G |
| dfreq10 | CA10X.chr10_170487106 | T/C | chr10 | 170,487,106 | T | T | C | C |
| dfreq10 | CA10X.chr10_170488990 | T/C | chr10 | 170,488,990 | T | T | C | C |
| dfreq10 | CA10X.chr10_170489090 | C/T | chr10 | 170,489,090 | T | T | C | C |
| dfreq10 | CA10X.chr10_170490757 | C/G | chr10 | 170,490,757 | C | C | G | G |
| dfreq10 | CA10X.chr10_170490758 | C/T | chr10 | 170,490,758 | T | T | C | C |
| dfreq10 | CA10X.chr10_170490776 | G/A | chr10 | 170,490,776 | A | A | G | G |
| dfreq10 | CA10X.chr10_170490833 | A/C | chr10 | 170,490,833 | C | C | A | A |
| dfreq10 | CA10X.chr10_170491066 | T/C | chr10 | 170,491,066 | C | C | T | T |
| dfreq10 | CA10X.chr10_170491616 | G/C | chr10 | 170,491,616 | G | G | C | C |
| dfreq10 | CA10X.chr10_170493894 | C/T | chr10 | 170,493,894 | T | T | C | C |
| dfreq10 | CA10X.chr10_170496521 | A/G | chr10 | 170,496,521 | G | G | A | A |
| dfreq10 | CA10X.chr10_170496576 | T/C | chr10 | 170,496,576 | C | C | T | T |
| dfreq10 | CA10X.chr10_170507404 | T/C | chr10 | 170,507,404 | T | T | C | C |
| dfreq10 | CA10X.chr10_170507651 | C/T | chr10 | 170,507,651 | C | C | T | T |
| dfreq10 | CA10X.chr10_170507661 | C/T | chr10 | 170,507,661 | C | C | T | T |
| dfreq10 | CA10X.chr10_170543688 | C/T | chr10 | 170,543,688 | C | C | T | T |
| dfreq10 | CA10X.chr10_170543724 | T/A | chr10 | 170,543,724 | T | T | A | A |
| dfreq10 | CA10X.chr10_170543727 | C/T | chr10 | 170,543,727 | T | T | C | C |
| dfreq10 | CA10X.chr10_170543816 | C/T | chr10 | 170,543,816 | C | C | T | T |
| dfreq10 | CA10X.chr10_170559250 | C/T | chr10 | 170,559,250 | C | C | T | T |
| dfreq10 | CA10X.chr10_170559964 | A/C | chr10 | 170,559,964 | A | A | C | C |
| dfreq10 | CA10X.chr10_170561799 | T/G | chr10 | 170,561,799 | T | T | G | G |
| dfreq10 | CA10X.chr10_170580492 | T/G | chr10 | 170,580,492 | G | G | T | T |
| dfreq10 | CA10X.chr10_170580575 | G/A | chr10 | 170,580,575 | G | G | A | A |
| dfreq10 | CA10X.chr10_170580587 | C/T | chr10 | 170,580,587 | C | C | T | T |
| dfreq10 | CA10X.chr10_170580734 | A/G | chr10 | 170,580,734 | G | G | A | A |
| dfreq10 | CA10X.chr10_170609353 | A/C | chr10 | 170,609,353 | A | A | C | C |
| dfreq10 | CA10X.chr10_170609362 | T/C | chr10 | 170,609,362 | T | T | C | C |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10__170609474 | C/T | chr10 | 170,609,474 | C | C | T | T |
| dfreq10 | CA10X.chr10__170609497 | G/T | chr10 | 170,609,497 | T | T | G | G |
| dfreq10 | CA10X.chr10__170609522 | A/G | chr10 | 170,609,522 | G | G | A | A |
| dfreq10 | CA10X.chr10__170609558 | T/C | chr10 | 170,609,558 | T | T | C | C |
| dfreq10 | CA10X.chr10__170609794 | A/C | chr10 | 170,609,794 | C | C | A | A |
| dfreq10 | CA10X.chr10__170619221 | C/G | chr10 | 170,619,221 | C | C | G | G |
| dfreq10 | CA10X.chr10__170619269 | T/C | chr10 | 170,619,269 | T | T | C | C |
| dfreq10 | CA10X.chr10__170619279 | C/T | chr10 | 170,619,279 | C | C | T | T |
| dfreq10 | CA10X.chr10__170619344 | G/A | chr10 | 170,619,344 | A | A | G | G |
| dfreq10 | CA10X.chr10__170619355 | T/G | chr10 | 170,619,355 | G | G | T | T |
| dfreq10 | CA10X.chr10__170619421 | C/G | chr10 | 170,619,421 | C | C | G | G |
| dfreq10 | CA10X.chr10__170619451 | G/A | chr10 | 170,619,451 | G | G | A | A |
| dfreq10 | CA10X.chr10__170619459 | T/C | chr10 | 170,619,459 | T | T | C | C |
| dfreq10 | CA10X.chr10__170621906 | A/G | chr10 | 170,621,906 | G | G | A | A |
| dfreq10 | CA10X.chr10__170621934 | T/A | chr10 | 170,621,934 | T | T | A | A |
| dfreq10 | CA10X.chr10__170621947 | A/C | chr10 | 170,621,947 | C | C | A | A |
| dfreq10 | CA10X.chr10__170622212 | C/T | chr10 | 170,622,212 | T | T | C | C |
| dfreq10 | CA10X.chr10__170622218 | G/A | chr10 | 170,622,218 | G | G | A | A |
| dfreq10 | CA10X.chr10__170623507 | C/T | chr10 | 170,623,507 | T | T | C | C |
| dfreq10 | CA10X.chr10__170632605 | A/G | chr10 | 170,632,605 | G | G | A | A |
| dfreq10 | CA10X.chr10__170632608 | G/A | chr10 | 170,632,608 | A | A | G | G |
| dfreq10 | CA10X.chr10__170632708 | G/A | chr10 | 170,632,708 | G | G | A | A |
| dfreq10 | CA10X.chr10__170632825 | T/C | chr10 | 170,632,825 | T | T | C | C |
| dfreq10 | CA10X.chr10__170632864 | C/T | chr10 | 170,632,864 | T | T | C | C |
| dfreq10 | CA10X.chr10__170634609 | G/T | chr10 | 170,634,609 | G | G | T | T |
| dfreq10 | CA10X.chr10__170634826 | G/A | chr10 | 170,634,826 | G | G | A | A |
| dfreq10 | CA10X.chr10__170634876 | T/C | chr10 | 170,634,876 | C | C | T | T |
| dfreq10 | CA10X.chr10__170635818 | A/G | chr10 | 170,635,818 | G | G | A | A |
| dfreq10 | CA10X.chr10__170635853 | A/C | chr10 | 170,635,853 | C | C | A | A |
| dfreq10 | CA10X.chr10__170635920 | G/A | chr10 | 170,635,920 | A | A | G | G |
| dfreq10 | CA10X.chr10__170636166 | C/T | chr10 | 170,636,166 | C | C | T | T |
| dfreq10 | CA10X.chr10__170636304 | T/A | chr10 | 170,636,304 | T | T | A | A |
| dfreq10 | CA10X.chr10__170638591 | T/C | chr10 | 170,638,591 | T | T | C | C |
| dfreq10 | CA10X.chr10__170638637 | G/A | chr10 | 170,638,637 | G | G | A | A |
| dfreq10 | CA10X.chr10__170638646 | A/G | chr10 | 170,638,646 | G | G | A | A |
| dfreq10 | CA10X.chr10__170646955 | C/A | chr10 | 170,646,955 | C | C | A | A |
| dfreq10 | CA10X.chr10__170646983 | A/G | chr10 | 170,646,983 | G | G | A | A |
| dfreq10 | CA10X.chr10__170647193 | C/T | chr10 | 170,647,193 | T | T | C | C |
| dfreq10 | CA10X.chr10__170652302 | T/C | chr10 | 170,652,302 | T | T | C | C |
| dfreq10 | CA10X.chr10__170653272 | T/C | chr10 | 170,653,272 | C | C | T | T |
| dfreq10 | CA10X.chr10__170653286 | A/G | chr10 | 170,653,286 | A | A | G | G |
| dfreq10 | CA10X.chr10__170653335 | G/A | chr10 | 170,653,335 | A | A | G | G |
| dfreq10 | CA10X.chr10__170653338 | A/G | chr10 | 170,653,338 | G | G | A | A |
| dfreq10 | CA10X.chr10__170665684 | C/T | chr10 | 170,665,684 | C | C | T | T |
| dfreq10 | CA10X.chr10__170683836 | A/T | chr10 | 170,683,836 | T | T | A | A |
| dfreq10 | CA10X.chr10__170690325 | A/G | chr10 | 170,690,325 | G | G | A | A |
| dfreq10 | CA10X.chr10__170690329 | A/G | chr10 | 170,690,329 | G | G | A | A |
| dfreq10 | CA10X.chr10__170690493 | A/G | chr10 | 170,690,493 | A | A | G | G |
| dfreq10 | CA10X.chr10__170690525 | C/T | chr10 | 170,690,525 | T | T | C | C |
| dfreq10 | CA10X.chr10__170695316 | G/C | chr10 | 170,695,316 | C | C | G | G |
| dfreq10 | CA10X.chr10__170695396 | T/C | chr10 | 170,695,396 | C | C | T | T |
| dfreq10 | CA10X.chr10__170695472 | T/A | chr10 | 170,695,472 | T | T | A | A |
| dfreq10 | CA10X.chr10__170706611 | T/G | chr10 | 170,706,611 | T | T | G | G |
| dfreq10 | CA10X.chr10__170715723 | C/T | chr10 | 170,715,723 | T | T | C | C |
| dfreq10 | CA10X.chr10__170715765 | T/C | chr10 | 170,715,765 | C | C | T | T |
| dfreq10 | CA10X.chr10__170716349 | C/T | chr10 | 170,716,349 | C | C | T | T |
| dfreq10 | CA10X.chr10__170717809 | T/C | chr10 | 170,717,809 | T | T | C | C |
| dfreq10 | CA10X.chr10__170717852 | A/T | chr10 | 170,717,852 | T | T | A | A |
| dfreq10 | CA10X.chr10__170726584 | C/T | chr10 | 170,726,584 | T | T | C | C |
| dfreq10 | CA10X.chr10__170726619 | T/C | chr10 | 170,726,619 | C | C | T | T |
| dfreq10 | CA10X.chr10__170726629 | C/T | chr10 | 170,726,629 | T | T | C | C |
| dfreq10 | CA10X.chr10__170727031 | G/T | chr10 | 170,727,031 | G | G | T | T |
| dfreq10 | CA10X.chr10__170727036 | T/C | chr10 | 170,727,036 | T | T | C | C |
| dfreq10 | CA10X.chr10__170727048 | A/G | chr10 | 170,727,048 | A | A | G | G |
| dfreq10 | CA10X.chr10__170727156 | G/T | chr10 | 170,727,156 | G | G | T | T |
| dfreq10 | CA10X.chr10__170728170 | C/A | chr10 | 170,728,170 | C | C | A | A |
| dfreq10 | CA10X.chr10__170728252 | A/T | chr10 | 170,728,252 | T | T | A | A |
| dfreq10 | CA10X.chr10__170742905 | T/C | chr10 | 170,742,905 | C | C | T | T |
| dfreq10 | CA10X.chr10__170742910 | C/T | chr10 | 170,742,910 | C | C | T | T |
| dfreq10 | CA10X.chr10__170743106 | C/A | chr10 | 170,743,106 | C | C | A | A |
| dfreq10 | CA10X.chr10__170743133 | G/A | chr10 | 170,743,133 | A | A | G | G |
| dfreq10 | CA10X.chr10__170743134 | A/C | chr10 | 170,743,134 | A | A | C | C |
| dfreq10 | CA10X.chr10__170750100 | G/T | chr10 | 170,750,100 | G | G | T | T |
| dfreq10 | CA10X.chr10__170750110 | T/C | chr10 | 170,750,110 | C | C | T | T |
| dfreq10 | CA10X.chr10__170752386 | G/A | chr10 | 170,752,386 | G | G | A | A |
| dfreq10 | CA10X.chr10__170752449 | C/A | chr10 | 170,752,449 | C | C | A | A |
| dfreq10 | CA10X.chr10__170754228 | A/C | chr10 | 170,754,228 | C | C | A | A |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10__170754309 | A/C | chr10 | 170,754,309 | A | A | C | C |
| dfreq10 | CA10X.chr10__170754315 | C/T | chr10 | 170,754,315 | C | C | T | T |
| dfreq10 | CA10X.chr10__170756871 | A/T | chr10 | 170,756,871 | A | A | T | T |
| dfreq10 | CA10X.chr10__170756918 | G/C | chr10 | 170,756,918 | G | G | C | C |
| dfreq10 | CA10X.chr10__170756935 | A/T | chr10 | 170,756,935 | A | A | T | T |
| dfreq10 | CA10X.chr10__170757000 | T/A | chr10 | 170,757,000 | A | A | T | T |
| dfreq10 | CA10X.chr10__170757062 | T/C | chr10 | 170,757,062 | T | T | C | C |
| dfreq10 | CA10X.chr10__170758404 | C/T | chr10 | 170,758,404 | C | C | T | T |
| dfreq10 | CA10X.chr10__170774599 | G/A | chr10 | 170,774,599 | G | G | A | A |
| dfreq10 | CA10X.chr10__170777234 | T/G | chr10 | 170,777,234 | G | G | T | T |
| dfreq10 | CA10X.chr10__170777406 | A/G | chr10 | 170,777,406 | G | G | A | A |
| dfreq10 | CA10X.chr10__170779821 | A/G | chr10 | 170,779,821 | A | A | G | G |
| dfreq10 | CA10X.chr10__170806877 | C/G | chr10 | 170,806,877 | G | G | C | C |
| dfreq10 | CA10X.chr10__170817787 | A/C | chr10 | 170,817,787 | C | C | A | A |
| dfreq10 | CA10X.chr10__170818362 | C/T | chr10 | 170,818,362 | C | C | T | T |
| dfreq10 | CA10X.chr10__170819709 | G/C | chr10 | 170,819,709 | G | G | C | C |
| dfreq10 | CA10X.chr10__170819751 | A/T | chr10 | 170,819,751 | A | A | T | T |
| dfreq10 | CA10X.chr10__170822928 | A/G | chr10 | 170,822,928 | A | A | G | G |
| dfreq10 | CA10X.chr10__170824914 | T/C | chr10 | 170,824,914 | C | C | T | T |
| dfreq10 | CA10X.chr10__170825015 | T/G | chr10 | 170,825,015 | G | G | T | T |
| dfreq10 | CA10X.chr10__170825016 | A/T | chr10 | 170,825,016 | T | T | A | A |
| dfreq10 | CA10X.chr10__170828583 | A/C | chr10 | 170,828,583 | A | A | C | C |
| dfreq10 | CA10X.chr10__170836679 | T/G | chr10 | 170,836,679 | G | G | T | T |
| dfreq10 | CA10X.chr10__170836754 | T/C | chr10 | 170,836,754 | C | C | T | T |
| dfreq10 | CA10X.chr10__170836777 | T/C | chr10 | 170,836,777 | T | T | C | C |
| dfreq10 | CA10X.chr10__170840981 | A/G | chr10 | 170,840,981 | G | G | A | A |
| dfreq10 | CA10X.chr10__170861582 | G/A | chr10 | 170,861,582 | G | G | A | A |
| dfreq10 | CA10X.chr10__170861639 | A/G | chr10 | 170,861,639 | G | G | A | A |
| dfreq10 | CA10X.chr10__170862459 | G/A | chr10 | 170,862,459 | G | G | A | A |
| dfreq10 | CA10X.chr10__170862568 | A/G | chr10 | 170,862,568 | G | G | A | A |
| dfreq10 | CA10X.chr10__170862632 | A/G | chr10 | 170,862,632 | A | A | G | G |
| dfreq10 | CA10X.chr10__170862664 | G/A | chr10 | 170,862,664 | A | A | G | G |
| dfreq10 | CA10X.chr10__170862739 | A/C | chr10 | 170,862,739 | C | C | A | A |
| dfreq10 | CA10X.chr10__170862780 | G/A | chr10 | 170,862,780 | A | A | G | G |
| dfreq10 | CA10X.chr10__170868292 | C/A | chr10 | 170,868,292 | A | A | C | C |
| dfreq10 | CA10X.chr10__170869575 | A/G | chr10 | 170,869,575 | A | A | G | G |
| dfreq10 | CA10X.chr10__170869601 | A/G | chr10 | 170,869,601 | G | G | A | A |
| dfreq10 | CA10X.chr10__170901615 | T/C | chr10 | 170,901,615 | T | T | C | C |
| dfreq10 | CA10X.chr10__170914987 | A/T | chr10 | 170,914,987 | A | A | T | T |
| dfreq10 | CA10X.chr10__170915083 | C/T | chr10 | 170,915,083 | C | C | T | T |
| dfreq10 | CA10X.chr10__170915436 | G/A | chr10 | 170,915,436 | A | A | G | G |
| dfreq10 | CA10X.chr10__170915595 | C/A | chr10 | 170,915,595 | C | C | A | A |
| dfreq10 | CA10X.chr10__170917693 | C/T | chr10 | 170,917,693 | C | C | T | T |
| dfreq10 | CA10X.chr10__170917894 | C/T | chr10 | 170,917,894 | T | T | C | C |
| dfreq10 | CA10X.chr10__170919957 | T/C | chr10 | 170,919,957 | C | C | T | T |
| dfreq10 | CA10X.chr10__170933151 | A/C | chr10 | 170,933,151 | C | C | A | A |
| dfreq10 | CA10X.chr10__170934468 | T/C | chr10 | 170,934,468 | C | C | T | T |
| dfreq10 | CA10X.chr10__170934564 | T/G | chr10 | 170,934,564 | T | T | G | G |
| dfreq10 | CA10X.chr10__170938893 | T/C | chr10 | 170,938,893 | T | T | C | C |
| dfreq10 | CA10X.chr10__170954503 | G/A | chr10 | 170,954,503 | A | A | G | G |
| dfreq10 | CA10X.chr10__170954535 | A/G | chr10 | 170,954,535 | G | G | A | A |
| dfreq10 | CA10X.chr10__170960003 | G/A | chr10 | 170,960,003 | A | A | G | G |
| dfreq10 | CA10X.chr10__170963927 | C/T | chr10 | 170,963,927 | C | C | T | T |
| dfreq10 | CA10X.chr10__170964125 | T/C | chr10 | 170,964,125 | C | C | T | T |
| dfreq10 | CA10X.chr10__170966217 | C/A | chr10 | 170,966,217 | C | C | A | A |
| dfreq10 | CA10X.chr10__170966286 | C/A | chr10 | 170,966,286 | C | C | A | A |
| dfreq10 | CA10X.chr10__170966334 | T/C | chr10 | 170,966,334 | T | T | C | C |
| dfreq10 | CA10X.chr10__170966458 | A/C | chr10 | 170,966,458 | A | A | C | C |
| dfreq10 | CA10X.chr10__170966639 | T/C | chr10 | 170,966,639 | T | T | C | C |
| dfreq10 | CA10X.chr10__170966677 | T/A | chr10 | 170,966,677 | A | A | T | T |
| dfreq10 | CA10X.chr10__170970668 | A/G | chr10 | 170,970,668 | A | A | G | G |
| dfreq10 | CA10X.chr10__170976855 | A/G | chr10 | 170,976,855 | A | A | G | G |
| dfreq10 | CA10X.chr10__170976904 | G/A | chr10 | 170,976,904 | G | G | A | A |
| dfreq10 | CA10X.chr10__170988468 | C/T | chr10 | 170,988,468 | T | T | C | C |
| dfreq10 | CA10X.chr10__170988656 | T/C | chr10 | 170,988,656 | T | T | C | C |
| dfreq10 | CA10X.chr10__170993875 | T/C | chr10 | 170,993,875 | C | C | T | T |
| dfreq10 | CA10X.chr10__171003091 | A/G | chr10 | 171,003,091 | A | A | G | G |
| dfreq10 | CA10X.chr10__171003186 | G/A | chr10 | 171,003,186 | G | G | A | A |
| dfreq10 | CA10X.chr10__171011391 | A/G | chr10 | 171,011,391 | G | G | A | A |
| dfreq10 | CA10X.chr10__171011483 | G/A | chr10 | 171,011,483 | A | A | G | G |
| dfreq10 | CA10X.chr10__171012636 | A/G | chr10 | 171,012,636 | A | A | G | G |
| dfreq10 | CA10X.chr10__171012657 | C/G | chr10 | 171,012,657 | G | G | C | C |
| dfreq10 | CA10X.chr10__171017014 | T/A | chr10 | 171,017,014 | A | A | T | T |
| dfreq10 | CA10X.chr10__171017268 | A/G | chr10 | 171,017,268 | G | G | A | A |
| dfreq10 | CA10X.chr10__171020133 | A/G | chr10 | 171,020,133 | G | G | A | A |
| dfreq10 | CA10X.chr10__171027749 | T/A | chr10 | 171,027,749 | A | A | T | T |
| dfreq10 | CA10X.chr10__171036489 | C/T | chr10 | 171,036,489 | C | C | T | T |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10__171177832 | T/C | chr10 | 171,177,832 | C | C | T | T |
| dfreq10 | CA10X.chr10__171177919 | T/C | chr10 | 171,177,919 | C | C | T | T |
| dfreq10 | CA10X.chr10__171290398 | G/A | chr10 | 171,290,398 | A | A | G | G |
| dfreq10 | CA10X.chr10__171367003 | T/G | chr10 | 171,367,003 | G | G | T | T |
| dfreq10 | CA10X.chr10__171607949 | G/A | chr10 | 171,607,949 | G | G | A | A |
| dfreq10 | CA10X.chr10__171719975 | T/C | chr10 | 171,719,975 | T | T | C | C |
| dfreq10 | CA10X.chr10__172099127 | C/T | chr10 | 172,099,127 | T | T | C | C |
| dfreq10 | CA10X.chr10__172867573 | T/G | chr10 | 172,867,573 | G | G | T | T |
| dfreq10 | CA10X.chr10__172884853 | T/C | chr10 | 172,884,853 | C | C | T | T |
| dfreq10 | CA10X.chr10__172931574 | C/G | chr10 | 172,931,574 | C | C | G | G |
| dfreq10 | CA10X.chr10__172942844 | A/C | chr10 | 172,942,844 | C | C | A | A |
| dfreq10 | CA10X.chr10__172944895 | T/G | chr10 | 172,944,895 | G | G | T | T |
| dfreq10 | CA10X.chr10__172956805 | A/T | chr10 | 172,956,805 | A | A | T | T |
| dfreq10 | CA10X.chr10__172965002 | C/T | chr10 | 172,965,002 | C | C | T | T |
| dfreq10 | CA10X.chr10__172965007 | C/T | chr10 | 172,965,007 | T | T | C | C |
| dfreq10 | CA10X.chr10__172965029 | T/G | chr10 | 172,965,029 | T | T | G | G |
| dfreq10 | CA10X.chr10__172967064 | G/A | chr10 | 172,967,064 | G | G | A | A |
| dfreq10 | CA10X.chr10__172967120 | G/A | chr10 | 172,967,120 | G | G | A | A |
| dfreq10 | CA10X.chr10__172967251 | G/A | chr10 | 172,967,251 | A | A | G | G |
| dfreq10 | CA10X.chr10__172975906 | C/T | chr10 | 172,975,906 | C | C | T | T |
| dfreq10 | CA10X.chr10__172975912 | G/A | chr10 | 172,975,912 | G | G | A | A |
| dfreq10 | CA10X.chr10__172975927 | A/G | chr10 | 172,975,927 | A | A | G | G |
| dfreq10 | CA10X.chr10__172975930 | G/A | chr10 | 172,975,930 | G | G | A | A |
| dfreq10 | CA10X.chr10__172975958 | A/G | chr10 | 172,975,958 | G | G | A | A |
| dfreq10 | CA10X.chr10__172976108 | A/G | chr10 | 172,976,108 | G | G | A | A |
| dfreq10 | CA10X.chr10__172976154 | G/A | chr10 | 172,976,154 | A | A | G | G |
| dfreq10 | CA10X.chr10__172976171 | G/A | chr10 | 172,976,171 | G | G | A | A |
| dfreq10 | CA10X.chr10__172979383 | T/C | chr10 | 172,979,383 | C | C | T | T |
| dfreq10 | CA10X.chr10__172979619 | A/G | chr10 | 172,979,619 | G | G | A | A |
| dfreq10 | CA10X.chr10__172979646 | A/G | chr10 | 172,979,646 | A | A | G | G |
| dfreq10 | CA10X.chr10__172991745 | G/A | chr10 | 172,991,745 | G | G | A | A |
| dfreq10 | CA10X.chr10__172991813 | C/A | chr10 | 172,991,813 | C | C | A | A |
| dfreq10 | CA10X.chr10__172991847 | C/A | chr10 | 172,991,847 | C | C | A | A |
| dfreq10 | CA10X.chr10__173000463 | A/G | chr10 | 173,000,463 | G | G | A | A |
| dfreq10 | CA10X.chr10__173000553 | T/A | chr10 | 173,000,553 | A | A | T | T |
| dfreq10 | CA10X.chr10__173003638 | G/A | chr10 | 173,003,638 | G | G | A | A |
| dfreq10 | CA10X.chr10__173003664 | A/T | chr10 | 173,003,664 | A | A | T | T |
| dfreq10 | CA10X.chr10__173003719 | G/T | chr10 | 173,003,719 | G | G | T | T |
| dfreq10 | CA10X.chr10__173003725 | G/A | chr10 | 173,003,725 | A | A | G | G |
| dfreq10 | CA10X.chr10__173003795 | T/C | chr10 | 173,003,795 | C | C | T | T |
| dfreq10 | CA10X.chr10__173003807 | A/G | chr10 | 173,003,807 | A | A | G | G |
| dfreq10 | CA10X.chr10__173003862 | C/A | chr10 | 173,003,862 | A | A | C | C |
| dfreq10 | CA10X.chr10__173005340 | A/G | chr10 | 173,005,340 | G | G | A | A |
| dfreq10 | CA10X.chr10__173008378 | A/G | chr10 | 173,008,378 | A | A | G | G |
| dfreq10 | CA10X.chr10__173008432 | C/T | chr10 | 173,008,432 | T | T | C | C |
| dfreq10 | CA10X.chr10__173008444 | G/A | chr10 | 173,008,444 | G | G | A | A |
| dfreq10 | CA10X.chr10__173008457 | C/A | chr10 | 173,008,457 | A | A | C | C |
| dfreq10 | CA10X.chr10__173008572 | T/G | chr10 | 173,008,572 | G | G | T | T |
| dfreq10 | CA10X.chr10__173008622 | G/A | chr10 | 173,008,622 | G | G | A | A |
| dfreq10 | CA10X.chr10__173013620 | G/A | chr10 | 173,013,620 | G | G | A | A |
| dfreq10 | CA10X.chr10__173013697 | G/C | chr10 | 173,013,697 | G | G | C | C |
| dfreq10 | CA10X.chr10__173013851 | A/G | chr10 | 173,013,851 | G | G | A | A |
| dfreq10 | CA10X.chr10__173013869 | T/G | chr10 | 173,013,869 | G | G | T | T |
| dfreq10 | CA10X.chr10__173015083 | G/A | chr10 | 173,015,083 | G | G | A | A |
| dfreq10 | CA10X.chr10__173015181 | T/C | chr10 | 173,015,181 | T | T | C | C |
| dfreq10 | CA10X.chr10__173015194 | T/C | chr10 | 173,015,194 | T | T | C | C |
| dfreq10 | CA10X.chr10__173015339 | C/T | chr10 | 173,015,339 | T | T | C | C |
| dfreq10 | CA10X.chr10__173015485 | A/G | chr10 | 173,015,485 | G | G | A | A |
| dfreq10 | CA10X.chr10__173021015 | C/T | chr10 | 173,021,015 | T | T | C | C |
| dfreq10 | CA10X.chr10__173021099 | C/A | chr10 | 173,021,099 | C | C | A | A |
| dfreq10 | CA10X.chr10__173028127 | G/A | chr10 | 173,028,127 | G | G | A | A |
| dfreq10 | CA10X.chr10__173028129 | T/C | chr10 | 173,028,129 | T | T | C | C |
| dfreq10 | CA10X.chr10__173028142 | C/T | chr10 | 173,028,142 | C | C | T | T |
| dfreq10 | CA10X.chr10__173028229 | A/G | chr10 | 173,028,229 | A | A | G | G |
| dfreq10 | CA10X.chr10__173073154 | A/G | chr10 | 173,073,154 | G | G | A | A |
| dfreq10 | CA10X.chr10__173083178 | T/C | chr10 | 173,083,178 | T | T | C | C |
| dfreq10 | CA10X.chr10__173083302 | C/T | chr10 | 173,083,302 | T | T | C | C |
| dfreq10 | CA10X.chr10__173085850 | C/T | chr10 | 173,085,850 | C | C | T | T |
| dfreq10 | CA10X.chr10__173085899 | C/A | chr10 | 173,085,899 | A | A | C | C |
| dfreq10 | CA10X.chr10__173087018 | G/A | chr10 | 173,087,018 | A | A | G | G |
| dfreq10 | CA10X.chr10__173091006 | C/G | chr10 | 173,091,006 | C | C | G | G |
| dfreq10 | CA10X.chr10__173097556 | T/C | chr10 | 173,097,556 | T | T | C | C |
| dfreq10 | CA10X.chr10__173097635 | G/A | chr10 | 173,097,635 | A | A | G | G |
| dfreq10 | CA10X.chr10__173108417 | A/T | chr10 | 173,108,417 | A | A | T | T |
| dfreq10 | CA10X.chr10__173114746 | T/C | chr10 | 173,114,746 | T | T | C | C |
| dfreq10 | CA10X.chr10__173114982 | T/C | chr10 | 173,114,982 | T | T | C | C |
| dfreq10 | CA10X.chr10__173115796 | G/A | chr10 | 173,115,796 | A | A | G | G |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10__173115863 | C/T | chr10 | 173,115,863 | C | C | T | T |
| dfreq10 | CA10X.chr10__173115867 | G/T | chr10 | 173,115,867 | T | T | G | G |
| dfreq10 | CA10X.chr10__173115913 | C/T | chr10 | 173,115,913 | C | C | T | T |
| dfreq10 | CA10X.chr10__173116080 | C/T | chr10 | 173,116,080 | C | C | T | T |
| dfreq10 | CA10X.chr10__173116121 | A/T | chr10 | 173,116,121 | A | A | T | T |
| dfreq10 | CA10X.chr10__173116406 | A/C | chr10 | 173,116,406 | C | C | A | A |
| dfreq10 | CA10X.chr10__173117265 | C/G | chr10 | 173,117,265 | C | C | G | G |
| dfreq10 | CA10X.chr10__173117610 | C/T | chr10 | 173,117,610 | C | C | T | T |
| dfreq10 | CA10X.chr10__173120093 | T/C | chr10 | 173,120,093 | C | C | T | T |
| dfreq10 | CA10X.chr10__173120095 | T/C | chr10 | 173,120,095 | C | C | T | T |
| dfreq10 | CA10X.chr10__173120120 | G/A | chr10 | 173,120,120 | A | A | G | G |
| dfreq10 | CA10X.chr10__173120164 | A/G | chr10 | 173,120,164 | G | G | A | A |
| dfreq10 | CA10X.chr10__173120173 | A/T | chr10 | 173,120,173 | A | A | T | T |
| dfreq10 | CA10X.chr10__173120200 | G/C | chr10 | 173,120,200 | C | C | G | G |
| dfreq10 | CA10X.chr10__173120452 | G/A | chr10 | 173,120,452 | A | A | G | G |
| dfreq10 | CA10X.chr10__173121961 | A/G | chr10 | 173,121,961 | G | G | A | A |
| dfreq10 | CA10X.chr10__173122045 | C/T | chr10 | 173,122,045 | C | C | T | T |
| dfreq10 | CA10X.chr10__173122270 | C/G | chr10 | 173,122,270 | G | G | C | C |
| dfreq10 | CA10X.chr10__173130878 | G/T | chr10 | 173,130,878 | T | T | G | G |
| dfreq10 | CA10X.chr10__173130953 | C/G | chr10 | 173,130,953 | C | C | G | G |
| dfreq10 | CA10X.chr10__173130980 | G/A | chr10 | 173,130,980 | G | G | A | A |
| dfreq10 | CA10X.chr10__173131004 | T/C | chr10 | 173,131,004 | T | T | C | C |
| dfreq10 | CA10X.chr10__173131072 | G/T | chr10 | 173,131,072 | T | T | G | G |
| dfreq10 | CA10X.chr10__173131103 | T/C | chr10 | 173,131,103 | C | C | T | T |
| dfreq10 | CA10X.chr10__173134314 | T/G | chr10 | 173,134,314 | G | G | T | T |
| dfreq10 | CA10X.chr10__173139655 | A/G | chr10 | 173,139,655 | G | G | A | A |
| dfreq10 | CA10X.chr10__173139721 | T/C | chr10 | 173,139,721 | C | C | T | T |
| dfreq10 | CA10X.chr10__173143556 | G/A | chr10 | 173,143,556 | G | G | A | A |
| dfreq10 | CA10X.chr10__173143635 | G/A | chr10 | 173,143,635 | A | A | G | G |
| dfreq10 | CA10X.chr10__173143660 | A/T | chr10 | 173,143,660 | T | T | A | A |
| dfreq10 | CA10X.chr10__173153930 | G/A | chr10 | 173,153,930 | A | A | G | G |
| dfreq10 | CA10X.chr10__173154344 | G/A | chr10 | 173,154,344 | G | G | A | A |
| dfreq10 | CA10X.chr10__173156120 | C/G | chr10 | 173,156,120 | C | C | G | G |
| dfreq10 | CA10X.chr10__173161278 | T/C | chr10 | 173,161,278 | T | T | C | C |
| dfreq10 | CA10X.chr10__173161297 | C/G | chr10 | 173,161,297 | G | G | C | C |
| dfreq10 | CA10X.chr10__173161352 | G/A | chr10 | 173,161,352 | G | G | A | A |
| dfreq10 | CA10X.chr10__173161414 | A/G | chr10 | 173,161,414 | G | G | A | A |
| dfreq10 | CA10X.chr10__173161433 | C/T | chr10 | 173,161,433 | C | C | T | T |
| dfreq10 | CA10X.chr10__173161568 | G/T | chr10 | 173,161,568 | G | G | T | T |
| dfreq10 | CA10X.chr10__173161773 | T/C | chr10 | 173,161,773 | C | C | T | T |
| dfreq10 | CA10X.chr10__173161774 | G/A | chr10 | 173,161,774 | G | G | A | A |
| dfreq10 | CA10X.chr10__173162221 | G/A | chr10 | 173,162,221 | G | G | A | A |
| dfreq10 | CA10X.chr10__173162325 | T/C | chr10 | 173,162,325 | C | C | T | T |
| dfreq10 | CA10X.chr10__173166770 | A/G | chr10 | 173,166,770 | G | G | A | A |
| dfreq10 | CA10X.chr10__173178444 | G/T | chr10 | 173,178,444 | G | G | T | T |
| dfreq10 | CA10X.chr10__173188462 | A/C | chr10 | 173,188,462 | A | A | C | C |
| dfreq10 | CA10X.chr10__173190191 | C/T | chr10 | 173,190,191 | T | T | C | C |
| dfreq10 | CA10X.chr10__173190223 | C/A | chr10 | 173,190,223 | A | A | C | C |
| dfreq10 | CA10X.chr10__173203292 | C/A | chr10 | 173,203,292 | A | A | C | C |
| dfreq10 | CA10X.chr10__173203335 | T/C | chr10 | 173,203,335 | C | C | T | T |
| dfreq10 | CA10X.chr10__173222912 | T/A | chr10 | 173,222,912 | A | A | T | T |
| dfreq10 | CA10X.chr10__173224072 | T/C | chr10 | 173,224,072 | T | T | C | C |
| dfreq10 | CA10X.chr10__173224190 | A/G | chr10 | 173,224,190 | G | G | A | A |
| dfreq10 | CA10X.chr10__173229140 | T/A | chr10 | 173,229,140 | A | A | T | T |
| dfreq10 | CA10X.chr10__173229318 | C/T | chr10 | 173,229,318 | C | C | T | T |
| dfreq10 | CA10X.chr10__173232730 | T/G | chr10 | 173,232,730 | G | G | T | T |
| dfreq10 | CA10X.chr10__173237440 | T/C | chr10 | 173,237,440 | T | T | C | C |
| dfreq10 | CA10X.chr10__173304496 | C/T | chr10 | 173,304,496 | T | T | C | C |
| dfreq10 | CA10X.chr10__173306568 | G/A | chr10 | 173,306,568 | A | A | G | G |
| dfreq10 | CA10X.chr10__173311747 | T/C | chr10 | 173,311,747 | T | T | C | C |
| dfreq10 | CA10X.chr10__173317914 | T/C | chr10 | 173,317,914 | T | T | C | C |
| dfreq10 | CA10X.chr10__173328304 | C/T | chr10 | 173,328,304 | T | T | C | C |
| dfreq10 | CA10X.chr10__173328327 | A/G | chr10 | 173,328,327 | A | A | G | G |
| dfreq10 | CA10X.chr10__173329072 | C/T | chr10 | 173,329,072 | T | T | C | C |
| dfreq10 | CA10X.chr10__173329086 | G/T | chr10 | 173,329,086 | T | T | G | G |
| dfreq10 | CA10X.chr10__173329097 | C/T | chr10 | 173,329,097 | T | T | C | C |
| dfreq10 | CA10X.chr10__173329178 | T/C | chr10 | 173,329,178 | T | T | C | C |
| dfreq10 | CA10X.chr10__173333721 | A/G | chr10 | 173,333,721 | A | A | G | G |
| dfreq10 | CA10X.chr10__173333803 | C/T | chr10 | 173,333,803 | T | T | C | C |
| dfreq10 | CA10X.chr10__173333809 | A/G | chr10 | 173,333,809 | A | A | G | G |
| dfreq10 | CA10X.chr10__173341338 | G/A | chr10 | 173,341,338 | G | G | A | A |
| dfreq10 | CA10X.chr10__173352292 | G/A | chr10 | 173,352,292 | G | G | A | A |
| dfreq10 | CA10X.chr10__173352380 | A/G | chr10 | 173,352,380 | A | A | G | G |
| dfreq10 | CA10X.chr10__173352502 | A/G | chr10 | 173,352,502 | A | A | G | G |
| dfreq10 | CA10X.chr10__173353035 | A/G | chr10 | 173,353,035 | G | G | A | A |
| dfreq10 | CA10X.chr10__173353091 | A/T | chr10 | 173,353,091 | T | T | A | A |
| dfreq10 | CA10X.chr10__173353092 | A/C | chr10 | 173,353,092 | C | C | A | A |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10__173353102 | C/T | chr10 | 173,353,102 | T | T | C | C |
| dfreq10 | CA10X.chr10__173353279 | T/G | chr10 | 173,353,279 | T | T | G | G |
| dfreq10 | CA10X.chr10__173353287 | G/A | chr10 | 173,353,287 | A | A | G | G |
| dfreq10 | CA10X.chr10__173360627 | G/A | chr10 | 173,360,627 | G | G | A | A |
| dfreq10 | CA10X.chr10__173364369 | G/C | chr10 | 173,364,369 | C | C | G | G |
| dfreq10 | CA10X.chr10__173386488 | T/C | chr10 | 173,386,488 | C | C | T | T |
| dfreq10 | CA10X.chr10__173386800 | C/A | chr10 | 173,386,800 | A | A | C | C |
| dfreq10 | CA10X.chr10__173386833 | G/A | chr10 | 173,386,833 | G | G | A | A |
| dfreq10 | CA10X.chr10__173402897 | G/A | chr10 | 173,402,897 | A | A | G | G |
| dfreq10 | CA10X.chr10__173402931 | A/G | chr10 | 173,402,931 | A | A | G | G |
| dfreq10 | CA10X.chr10__173433154 | A/C | chr10 | 173,433,154 | C | C | A | A |
| dfreq10 | CA10X.chr10__173433339 | T/C | chr10 | 173,433,339 | C | C | T | T |
| dfreq10 | CA10X.chr10__173437083 | A/T | chr10 | 173,437,083 | T | T | A | A |
| dfreq10 | CA10X.chr10__173444865 | C/T | chr10 | 173,444,865 | T | T | C | C |
| dfreq10 | CA10X.chr10__173444930 | T/C | chr10 | 173,444,930 | C | C | T | T |
| dfreq10 | CA10X.chr10__173445099 | C/T | chr10 | 173,445,099 | C | C | T | T |
| dfreq10 | CA10X.chr10__173445134 | T/C | chr10 | 173,445,134 | C | C | T | T |
| dfreq10 | CA10X.chr10__173498607 | A/G | chr10 | 173,498,607 | G | G | A | A |
| dfreq10 | CA10X.chr10__173498617 | C/T | chr10 | 173,498,617 | C | C | T | T |
| dfreq10 | CA10X.chr10__173498636 | A/G | chr10 | 173,498,636 | A | A | G | G |
| dfreq10 | CA10X.chr10__173516688 | T/C | chr10 | 173,516,688 | C | C | T | T |
| dfreq10 | CA10X.chr10__173516706 | C/T | chr10 | 173,516,706 | C | C | T | T |
| dfreq10 | CA10X.chr10__173516836 | T/G | chr10 | 173,516,836 | T | T | G | G |
| dfreq10 | CA10X.chr10__173525461 | A/G | chr10 | 173,525,461 | G | G | A | A |
| dfreq10 | CA10X.chr10__173531820 | G/C | chr10 | 173,531,820 | G | G | C | C |
| dfreq10 | CA10X.chr10__173531923 | C/G | chr10 | 173,531,923 | G | G | C | C |
| dfreq10 | CA10X.chr10__173531932 | C/T | chr10 | 173,531,932 | C | C | T | T |
| dfreq10 | CA10X.chr10__173540817 | T/C | chr10 | 173,540,817 | C | C | T | T |
| dfreq10 | CA10X.chr10__173540917 | T/A | chr10 | 173,540,917 | A | A | T | T |
| dfreq10 | CA10X.chr10__173541054 | G/A | chr10 | 173,541,054 | A | A | G | G |
| dfreq10 | CA10X.chr10__173541108 | T/C | chr10 | 173,541,108 | C | C | T | T |
| dfreq10 | CA10X.chr10__173541132 | G/T | chr10 | 173,541,132 | T | T | G | G |
| dfreq10 | CA10X.chr10__173541179 | G/A | chr10 | 173,541,179 | G | G | A | A |
| dfreq10 | CA10X.chr10__173563178 | C/T | chr10 | 173,563,178 | C | C | T | T |
| dfreq10 | CA10X.chr10__173563280 | A/G | chr10 | 173,563,280 | A | A | G | G |
| dfreq10 | CA10X.chr10__173563344 | A/G | chr10 | 173,563,344 | G | G | A | A |
| dfreq10 | CA10X.chr10__173624757 | A/G | chr10 | 173,624,757 | A | A | G | G |
| dfreq10 | CA10X.chr10__173624770 | A/G | chr10 | 173,624,770 | A | A | G | G |
| dfreq10 | CA10X.chr10__173631145 | T/C | chr10 | 173,631,145 | C | C | T | T |
| dfreq10 | CA10X.chr10__173631160 | G/T | chr10 | 173,631,160 | T | T | G | G |
| dfreq10 | CA10X.chr10__173634952 | C/T | chr10 | 173,634,952 | T | T | C | C |
| dfreq10 | CA10X.chr10__173634987 | T/C | chr10 | 173,634,987 | C | C | T | T |
| dfreq10 | CA10X.chr10__173645493 | C/T | chr10 | 173,645,493 | C | C | T | T |
| dfreq10 | CA10X.chr10__173645529 | C/T | chr10 | 173,645,529 | C | C | T | T |
| dfreq10 | CA10X.chr10__173645704 | G/A | chr10 | 173,645,704 | G | G | A | A |
| dfreq10 | CA10X.chr10__173651310 | A/G | chr10 | 173,651,310 | G | G | A | A |
| dfreq10 | CA10X.chr10__173653215 | T/C | chr10 | 173,653,215 | C | C | T | T |
| dfreq10 | CA10X.chr10__173653216 | G/A | chr10 | 173,653,216 | G | G | A | A |
| dfreq10 | CA10X.chr10__173653338 | A/G | chr10 | 173,653,338 | A | A | G | G |
| dfreq10 | CA10X.chr10__173653495 | C/T | chr10 | 173,653,495 | C | C | T | T |
| dfreq10 | CA10X.chr10__173653535 | A/G | chr10 | 173,653,535 | G | G | A | A |
| dfreq10 | CA10X.chr10__173654591 | A/T | chr10 | 173,654,591 | T | T | A | A |
| dfreq10 | CA10X.chr10__173654915 | G/T | chr10 | 173,654,915 | G | G | T | T |
| dfreq10 | CA10X.chr10__173656247 | G/C | chr10 | 173,656,247 | C | C | G | G |
| dfreq10 | CA10X.chr10__173656324 | T/G | chr10 | 173,656,324 | G | G | T | T |
| dfreq10 | CA10X.chr10__173656410 | A/G | chr10 | 173,656,410 | A | A | G | G |
| dfreq10 | CA10X.chr10__173674574 | A/G | chr10 | 173,674,574 | A | A | G | G |
| dfreq10 | CA10X.chr10__173695892 | C/G | chr10 | 173,695,892 | C | C | G | G |
| dfreq10 | CA10X.chr10__173710615 | T/C | chr10 | 173,710,615 | C | C | T | T |
| dfreq10 | CA10X.chr10__173750662 | C/T | chr10 | 173,750,662 | C | C | T | T |
| dfreq10 | CA10X.chr10__173750705 | T/C | chr10 | 173,750,705 | C | C | T | T |
| dfreq10 | CA10X.chr10__173750792 | T/C | chr10 | 173,750,792 | T | T | C | C |
| dfreq10 | CA10X.chr10__173750893 | C/T | chr10 | 173,750,893 | T | T | C | C |
| dfreq10 | CA10X.chr10__173750917 | G/A | chr10 | 173,750,917 | A | A | G | G |
| dfreq10 | CA10X.chr10__173760566 | A/G | chr10 | 173,760,566 | A | A | G | G |
| dfreq10 | CA10X.chr10__173760665 | T/G | chr10 | 173,760,665 | T | T | G | G |
| dfreq10 | CA10X.chr10__173760688 | A/C | chr10 | 173,760,688 | A | A | C | C |
| dfreq10 | CA10X.chr10__173760692 | C/T | chr10 | 173,760,692 | T | T | C | C |
| dfreq10 | CA10X.chr10__173807360 | T/C | chr10 | 173,807,360 | T | T | C | C |
| dfreq10 | CA10X.chr10__173808234 | G/A | chr10 | 173,808,234 | G | G | A | A |
| dfreq10 | CA10X.chr10__173808287 | A/G | chr10 | 173,808,287 | A | A | G | G |
| dfreq10 | CA10X.chr10__173808473 | T/C | chr10 | 173,808,473 | T | T | C | C |
| dfreq10 | CA10X.chr10__173810341 | A/G | chr10 | 173,810,341 | G | G | A | A |
| dfreq10 | CA10X.chr10__173810344 | C/T | chr10 | 173,810,344 | C | C | T | T |
| dfreq10 | CA10X.chr10__173843277 | G/C | chr10 | 173,843,277 | G | G | C | C |
| dfreq10 | CA10X.chr10__173843292 | T/A | chr10 | 173,843,292 | A | A | T | T |
| dfreq10 | CA10X.chr10__173847933 | A/T | chr10 | 173,847,933 | A | A | T | T |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10_173861356 | C/T | chr10 | 173,861,356 | T | T | C | C |
| dfreq10 | CA10X.chr10_173861358 | G/A | chr10 | 173,861,358 | A | A | G | G |
| dfreq10 | CA10X.chr10_173861367 | G/A | chr10 | 173,861,367 | A | A | G | G |
| dfreq10 | CA10X.chr10_173861415 | C/T | chr10 | 173,861,415 | T | T | C | C |
| dfreq10 | CA10X.chr10_173861444 | C/T | chr10 | 173,861,444 | C | C | T | T |
| dfreq10 | CA10X.chr10_173862194 | G/T | chr10 | 173,862,194 | G | G | T | T |
| dfreq10 | CA10X.chr10_173862216 | T/C | chr10 | 173,862,216 | T | T | C | C |
| dfreq10 | CA10X.chr10_173862325 | A/C | chr10 | 173,862,325 | C | C | A | A |
| dfreq10 | CA10X.chr10_173863294 | G/A | chr10 | 173,863,294 | G | G | A | A |
| dfreq10 | CA10X.chr10_173863397 | C/T | chr10 | 173,863,397 | C | C | T | T |
| dfreq10 | CA10X.chr10_173874442 | T/G | chr10 | 173,874,442 | G | G | T | T |
| dfreq10 | CA10X.chr10_173883008 | C/T | chr10 | 173,883,008 | C | C | T | T |
| dfreq10 | CA10X.chr10_173883029 | A/G | chr10 | 173,883,029 | A | A | G | G |
| dfreq10 | CA10X.chr10_173883160 | A/G | chr10 | 173,883,160 | G | G | A | A |
| dfreq10 | CA10X.chr10_173883316 | T/G | chr10 | 173,883,316 | T | T | G | G |
| dfreq10 | CA10X.chr10_173883330 | T/C | chr10 | 173,883,330 | T | T | C | C |
| dfreq10 | CA10X.chr10_173883344 | T/A | chr10 | 173,883,344 | T | T | A | A |
| dfreq10 | CA10X.chr10_173884617 | A/G | chr10 | 173,884,617 | A | A | G | G |
| dfreq10 | CA10X.chr10_173884618 | G/A | chr10 | 173,884,618 | A | A | G | G |
| dfreq10 | CA10X.chr10_173892556 | T/C | chr10 | 173,892,556 | C | C | T | T |
| dfreq10 | CA10X.chr10_173892668 | G/A | chr10 | 173,892,668 | A | A | G | G |
| dfreq10 | CA10X.chr10_173897633 | C/T | chr10 | 173,897,633 | C | C | T | T |
| dfreq10 | CA10X.chr10_173897634 | A/G | chr10 | 173,897,634 | A | A | G | G |
| dfreq10 | CA10X.chr10_173897798 | C/T | chr10 | 173,897,798 | C | C | T | T |
| dfreq10 | CA10X.chr10_173897927 | C/A | chr10 | 173,897,927 | A | A | C | C |
| dfreq10 | CA10X.chr10_173898267 | T/C | chr10 | 173,898,267 | T | T | C | C |
| dfreq10 | CA10X.chr10_173901012 | G/A | chr10 | 173,901,012 | G | G | A | A |
| dfreq10 | CA10X.chr10_173901145 | A/G | chr10 | 173,901,145 | A | A | G | G |
| dfreq10 | CA10X.chr10_173906389 | C/T | chr10 | 173,906,389 | C | C | T | T |
| dfreq10 | CA10X.chr10_173908354 | T/C | chr10 | 173,908,354 | T | T | C | C |
| dfreq10 | CA10X.chr10_173908412 | C/T | chr10 | 173,908,412 | C | C | T | T |
| dfreq10 | CA10X.chr10_173912958 | C/T | chr10 | 173,912,958 | C | C | T | T |
| dfreq10 | CA10X.chr10_173929444 | A/G | chr10 | 173,929,444 | G | G | A | A |
| dfreq10 | CA10X.chr10_173937601 | G/C | chr10 | 173,937,601 | G | G | C | C |
| dfreq10 | CA10X.chr10_173952471 | A/G | chr10 | 173,952,471 | G | G | A | A |
| dfreq10 | CA10X.chr10_173952558 | T/C | chr10 | 173,952,558 | T | T | C | C |
| dfreq10 | CA10X.chr10_173954778 | A/G | chr10 | 173,954,778 | G | G | A | A |
| dfreq10 | CA10X.chr10_173954791 | G/A | chr10 | 173,954,791 | G | G | A | A |
| dfreq10 | CA10X.chr10_173954891 | T/G | chr10 | 173,954,891 | T | T | G | G |
| dfreq10 | CA10X.chr10_173956862 | A/G | chr10 | 173,956,862 | G | G | A | A |
| dfreq10 | CA10X.chr10_173956887 | G/A | chr10 | 173,956,887 | G | G | A | A |
| dfreq10 | CA10X.chr10_173967763 | A/G | chr10 | 173,967,763 | A | A | G | G |
| dfreq10 | CA10X.chr10_173971807 | G/A | chr10 | 173,971,807 | A | A | G | G |
| dfreq10 | CA10X.chr10_173971821 | A/T | chr10 | 173,971,821 | T | T | A | A |
| dfreq10 | CA10X.chr10_173973473 | C/T | chr10 | 173,973,473 | T | T | C | C |
| dfreq10 | CA10X.chr10_173994067 | G/A | chr10 | 173,994,067 | A | A | G | G |
| dfreq10 | CA10X.chr10_173994344 | A/G | chr10 | 173,994,344 | A | A | G | G |
| dfreq10 | CA10X.chr10_173994405 | C/T | chr10 | 173,994,405 | C | C | T | T |
| dfreq10 | CA10X.chr10_174002559 | G/A | chr10 | 174,002,559 | A | A | G | G |
| dfreq10 | CA10X.chr10_174002561 | G/T | chr10 | 174,002,561 | T | T | G | G |
| dfreq10 | CA10X.chr10_174002660 | G/C | chr10 | 174,002,660 | G | G | C | C |
| dfreq10 | CA10X.chr10_174002678 | G/T | chr10 | 174,002,678 | T | T | G | G |
| dfreq10 | CA10X.chr10_174002713 | A/G | chr10 | 174,002,713 | A | A | G | G |
| dfreq10 | CA10X.chr10_174022356 | A/T | chr10 | 174,022,356 | A | A | T | T |
| dfreq10 | CA10X.chr10_174051460 | G/A | chr10 | 174,051,460 | G | G | A | A |
| dfreq10 | CA10X.chr10_174071242 | T/C | chr10 | 174,071,242 | T | T | C | C |
| dfreq10 | CA10X.chr10_174071365 | A/G | chr10 | 174,071,365 | A | A | G | G |
| dfreq10 | CA10X.chr10_174071392 | C/T | chr10 | 174,071,392 | C | C | T | T |
| dfreq10 | CA10X.chr10_174071443 | C/T | chr10 | 174,071,443 | T | T | C | C |
| dfreq10 | CA10X.chr10_174071476 | C/T | chr10 | 174,071,476 | C | C | T | T |
| dfreq10 | CA10X.chr10_174074412 | C/T | chr10 | 174,074,412 | T | T | C | C |
| dfreq10 | CA10X.chr10_174074416 | A/G | chr10 | 174,074,416 | A | A | G | G |
| dfreq10 | CA10X.chr10_174074457 | C/T | chr10 | 174,074,457 | C | C | T | T |
| dfreq10 | CA10X.chr10_174074486 | C/A | chr10 | 174,074,486 | C | C | A | A |
| dfreq10 | CA10X.chr10_174074534 | T/C | chr10 | 174,074,534 | T | T | C | C |
| dfreq10 | CA10X.chr10_174074553 | T/G | chr10 | 174,074,553 | T | T | G | G |
| dfreq10 | CA10X.chr10_174107455 | G/T | chr10 | 174,107,455 | T | T | G | G |
| dfreq10 | CA10X.chr10_174107502 | G/A | chr10 | 174,107,502 | A | A | G | G |
| dfreq10 | CA10X.chr10_174107529 | G/A | chr10 | 174,107,529 | G | G | A | A |
| dfreq10 | CA10X.chr10_174107530 | C/T | chr10 | 174,107,530 | T | T | C | C |
| dfreq10 | CA10X.chr10_174107556 | T/C | chr10 | 174,107,556 | T | T | C | C |
| dfreq10 | CA10X.chr10_174107571 | A/G | chr10 | 174,107,571 | A | A | G | G |
| dfreq10 | CA10X.chr10_174111055 | A/G | chr10 | 174,111,055 | A | A | G | G |
| dfreq10 | CA10X.chr10_174111451 | C/T | chr10 | 174,111,451 | T | T | C | C |
| dfreq10 | CA10X.chr10_174111511 | A/C | chr10 | 174,111,511 | C | C | A | A |
| dfreq10 | CA10X.chr10_174111550 | G/A | chr10 | 174,111,550 | G | G | A | A |
| dfreq10 | CA10X.chr10_174111568 | G/A | chr10 | 174,111,568 | G | G | A | A |

TABLE 4-continued

| QTL | Marker | alleles | chrom | pos | Garnet | Maor | UCD14 | favorable allele |
|---|---|---|---|---|---|---|---|---|
| dfreq10 | CA10X.chr10_174123278 | A/C | chr10 | 174,123,278 | A | A | C | C |
| dfreq10 | CA10X.chr10_174123319 | T/C | chr10 | 174,123,319 | T | T | C | C |
| dfreq10 | CA10X.chr10_174873248 | A/G | chr10 | 174,873,248 | G | G | A | A |
| dfreq10 | CA10X.chr10_174986954 | C/T | chr10 | 174,986,954 | T | T | C | C |
| dfreq10 | CA10X.chr10_174987185 | A/G | chr10 | 174,987,185 | A | A | G | G |
| dfreq10 | CA10X.chr10_174987202 | T/G | chr10 | 174,987,202 | G | G | T | T |
| dfreq10 | CA10X.chr10_176405366 | T/C | chr10 | 176,405,366 | T | T | C | C |
| dfreq10 | CA10X.chr10_176407620 | C/T | chr10 | 176,407,620 | T | T | C | C |
| dfreq10 | CA10X.chr10_176436785 | A/G | chr10 | 176,436,785 | A | A | G | G |
| dfreq10 | CA10X.chr10_176436812 | C/T | chr10 | 176,436,812 | T | T | C | C |
| dfreq10 | CA10X.chr10_176436844 | A/C | chr10 | 176,436,844 | A | A | C | C |
| dfreq10 | CA10X.chr10_176437011 | G/T | chr10 | 176,437,011 | G | G | T | T |
| dfreq10 | CA10X.chr10_176437023 | T/G | chr10 | 176,437,023 | G | G | T | T |
| dfreq10 | CA10X.chr10_176437108 | C/T | chr10 | 176,437,108 | C | C | T | T |
| dfreq10 | CA10X.chr10_176437176 | G/A | chr10 | 176,437,176 | G | G | A | A |
| dfreq10 | CA10X.chr10_176437177 | T/C | chr10 | 176,437,177 | T | T | C | C |
| dfreq10 | CA10X.chr10_176437178 | G/A | chr10 | 176,437,178 | G | G | A | A |
| dfreq10 | CA10X.chr10_176437276 | C/T | chr10 | 176,437,276 | T | T | C | C |
| dfreq10 | CA10X.chr10_176437419 | T/C | chr10 | 176,437,419 | T | T | C | C |
| dfreq10 | CA10X.chr10_176815719 | C/T | chr10 | 176,815,719 | T | T | C | C |

Table 5 and FIG. 6 provide genotype tables with force and frequency values for some lines selected for more in depth evaluation. Table 5 shows a summary of the allele calls of certain progeny whose genotype is shown in FIG. 6, + indicates the favorable allele and − indicates alternate allele, +/− is heterozygous. The cell with + (+/−) indicates a possible recombination event between markers under the QTL. FIG. 6, bottom portion includes top selections among these lines. R and Y indicate heterozygosity.

TABLE 5

| | Frequency | Force (N) | Force chr2 | Force chr3 | Frequency chr4 | Force chr7 | Frequency chr10 |
|---|---|---|---|---|---|---|---|
| UCD-14 | 69% | 19.1 | + | + | + | − | + |
| Maor | 0% | na | − | − | − | + | − |
| MUC14-200 | 50% | 22.9 | − | + | | + | + |
| MUC14-297 | 54% | 23.0 | + | − | | − | + |
| MUC14-228 | 58% | 26.9 | + | +/− | | +/− | + |
| MUC14-37 | 71% | 28.0 | − | + | + | + | + |
| MUC14-17 | 82% | 30.0 | − | + | + | + | + |
| MUC14-30 | 87% | 32.9 | − | + | + | + | + |
| MUC14-330 | 79% | 35.5 | − | +/− | | + | − |

As can be seen from Table 5, peppers with desirable low destemming force include those as follows: Having at least one or more favorable allele(s) at the regions defined in 1, 2, 3, or all 4 of the regions defined in Table 3A for chromosomes 2, 3, 7, and 10. For example, in some embodiments, the pepper has an allele of UCD-14 from chromosome 2; or 2 and 10; or 2 and 10; or 3 and 10; or 2 and 3 and 10. In some embodiments, the pepper further has an allele of UCD-14 from chromosome 4. In some embodiments, any of the previous combinations are combined with a Maor allele from the region defined in chromosome 7. All of the regions are defined relative to the pepper genome in Table 3. SNPs for measuring the presence or absence of alleles in this region can be found in Table 1 and 4. Exemplary sequences surrounding the SNPs of Table 1 are shown in Table 2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, GenBank Accessions, and patent applications cited herein are hereby incorporated by reference in their entirety for all purposes.

REFERENCES

1. Bingley G, Leonard R, Buchele W, Stout B, Ries S. 1962. Mechanized cucumber harvesting. Agricultural Engineering 43:22-5
2. Chen P, Sun Z. 1984. Critical strain failure criterion: Pros and cons. Transactions of the ASAE 27:278-81
3. Emerson P. Economic impact of water pollution control regulations on the tomato processing industry
4. Funk P, Walker S. 2010. Evaluation of five green chile cultivars utilizing different harvest mechanisms. Applied Engineering in Agriculture 26:955-64
5. IBISWORLD. 2012. Hot Sauce Production in the US: Market Research Report.
6. Kender W, Hartmond U. 1999. Variability in detachment force and other properties of fruit within orange tree canopies. Fruit Varieties Journal 53:105-9
7. Marshall D, Boese B. 1998. Breeding *Capsicum* for mechanical harvest Part 2-Equipment. In Proceedings of the 10th Eucarpia Meeting on Genetics and Breeding of *Capsicum* and Eggplant, pp. 61-4. Avignon, France
8. Marshall D E, Levin J H, Cargill B F, Wittenberger R T. 1972. Quality of bulk handled 'Concord' grapes. In nnu. Mtg. Amer. Soc. Enol. Univ. of California, Davis, Calif.
9. Miles J, Hinz W, Pike W. 1978. Development of a mechanism for picking chile peppers. Transactions of the ASAE 21:419-21

10. Takele E, Daugovish O, Vue M. 2013. Costs and profitability analysis for bell pepper production in the Oxnard Plain, Ventura County, 2012-13: Fresh bell pepper production for processing.
11. Takele E, Daugovish O, Vue M. 2013. Costs and profitability analysis for bell pepper production in the Oxnard Plain, Ventura County, 2012-13: Fresh bell pepper production.
12. USDA. 2014. National Agricultural Statistics Service. World wide web at: nass.usda.gov/.
13. Walker S J, Funk P A. 2014. Mechanizing Chile Peppers: Challenges and Advances in Transitioning Harvest of New Mexico's Signature Crop. HortTechnology 24:281-4

What is claimed is:

1. A cultivated pepper plant having
   (i) a destemming force of less than 30 Newtons as measured for a straight pull with a force gauge or less than 35 Newtons using a torque watch gauge for separation of the pedicel and the stem; and
   (ii) a pericarp thickness between 2.5 and 4.0 mm, wherein the pepper is heterozygous or homozygous for one or more UCD-14 allele on chromosome 10 selected from the group consisting of:

| QTL | Marker | alleles | chrom | pos | Garnet | Maor | UCD14 | favorable allele |
|---|---|---|---|---|---|---|---|---|
| dfreq10 | CA10X.chr10_ 156062352 | A/C | chr10 | 156,062,352 | A | A | C | C |
| dfreq10 | CA10X.chr10_ 156067302 | G/A | chr10 | 156,067,302 | G | G | A | A |
| dfreq10 | CA10X.chr10_ 156067408 | T/C | chr10 | 156,067,408 | C | C | T | T |
| dfreq10 | CA10X.chr10_ 156068372 | T/C | chr10 | 156,068,372 | C | C | T | T |
| dfreq10 | CA10X.chr10_ 156105534 | G/A | chr10 | 156,105,534 | A | A | G | G |
| dfreq10 | CA10X.chr10_ 156119248 | A/G | chr10 | 156,119,248 | A | A | G | G |
| dfreq10 | CA10X.chr10_ 156137730 | T/C | chr10 | 156,137,730 | C | C | T | T |
| dfreq10 | CA10X.chr10_ 156141244 | A/G | chr10 | 156,141,244 | A | A | G | G |
| dfreq10 | CA10X.chr10_ 156141338 | G/A | chr10 | 156,141,338 | G | G | A | A |
| dfreq10 | CA10X.chr10_ 156141435 | G/A | chr10 | 156,141,435 | G | G | A | A |
| dfreq10 | CA10X.chr10_ 156141459 | G/A | chr10 | 156,141,459 | A | A | G | G |
| dfreq10 | CA10X.chr10_ 156141517 | T/C | chr10 | 156,141,517 | T | T | C | C |
| dfreq10 | CA10X.chr10_ 156141536 | A/G | chr10 | 156,141,536 | A | A | G | G |
| dfreq10 | CA10X.chr10_ 156141660 | A/G | chr10 | 156,141,660 | G | G | A | A |
| dfreq10 | CA10X.chr10_ 156145742 | A/G | chr10 | 156,145,742 | G | G | A | A |
| dfreq10 | CA10X.chr10_ 156153036 | A/G | chr10 | 156,153,036 | G | G | A | A |
| dfreq10 | CA10X.chr10_ 156171583 | C/G | chr10 | 156,171,583 | C | C | G | G |
| dfreq10 | CA10X.chr10_ 156195807 | C/A | chr10 | 156,195,807 | C | C | A | A |
| dfreq10 | CA10X.chr10_ 156210420 | A/G | chr10 | 156,210,420 | A | A | G | G |
| dfreq10 | CA10X.chr10_ 156217703 | C/T | chr10 | 156,217,703 | C | C | T | T |
| dfreq10 | CA10X.chr10_ 156224769 | G/A | chr10 | 156,224,769 | A | A | G | G |
| dfreq10 | CA10X.chr10_ 156228616 | A/G | chr10 | 156,228,616 | G | G | A | A |
| dfreq10 | CA10X.chr10_ 156235039 | T/C | chr10 | 156,235,039 | C | C | T | T |
| dfreq10 | CA10X.chr10_ 156253401 | A/G | chr10 | 156,253,401 | A | A | G | G |
| dfreq10 | CA10X.chr10_ 156253464 | C/T | chr10 | 156,253,464 | T | T | C | C |
| dfreq10 | CA10X.chr10_ 156253536 | A/G | chr10 | 156,253,536 | A | A | G | G |
| dfreq10 | CA10X.chr10_ 156257424 | A/C | chr10 | 156,257,424 | A | A | C | C |
| dfreq10 | CA10X.chr10_ 156257672 | G/A | chr10 | 156,257,672 | G | G | A | A |
| dfreq10 | CA10X.chr10_ 156257708 | T/C | chr10 | 156,257,708 | C | C | T | T |
| dfreq10 | CA10X.chr10_ 156257734 | C/T | chr10 | 156,257,734 | T | T | C | C |
| dfreq10 | CA10X.chr10_ 156257812 | A/G | chr10 | 156,257,812 | A | A | G | G |
| dfreq10 | CA10X.chr10_ 156257854 | A/G | chr10 | 156,257,854 | G | G | A | A |
| dfreq10 | CA10X.chr10_ 156264340 | C/T | chr10 | 156,264,340 | C | C | T | T |
| dfreq10 | CA10X.chr10_ 156264560 | G/A | chr10 | 156,264,560 | G | G | A | A |
| dfreq10 | CA10X.chr10_ 156264618 | T/C | chr10 | 156,264,618 | T | T | C | C |
| dfreq10 | CA10X.chr10_ 156264620 | T/G | chr10 | 156,264,620 | G | G | T | T |
| dfreq10 | CA10X.chr10_ 156277975 | G/T | chr10 | 156,277,975 | G | G | T | T |
| dfreq10 | CA10X.chr10_ 156277994 | G/A | chr10 | 156,277,994 | G | G | A | A |
| dfreq10 | CA10X.chr10_ 156280487 | G/A | chr10 | 156,280,487 | G | G | A | A |
| dfreq10 | CA10X.chr10_ 156280502 | T/C | chr10 | 156,280,502 | T | T | C | C |
| dfreq10 | CA10X.chr10_ 156282448 | C/T | chr10 | 156,282,448 | C | C | T | T |
| dfreq10 | CA10X.chr10_ 156282528 | T/C | chr10 | 156,282,528 | T | T | C | C |
| dfreq10 | CA10X.chr10_ 156285407 | G/A | chr10 | 156,285,407 | A | A | G | G |
| dfreq10 | CA10X.chr10_ 156285485 | T/G | chr10 | 156,285,485 | T | T | G | G |
| dfreq10 | CA10X.chr10_ 156290790 | C/T | chr10 | 156,290,790 | C | C | T | T |
| dfreq10 | CA10X.chr10_ 156290828 | C/T | chr10 | 156,290,828 | C | C | T | T |
| dfreq10 | CA10X.chr10_ 156308038 | A/G | chr10 | 156,308,038 | A | A | G | G |
| dfreq10 | CA10X.chr10_ 156308133 | T/C | chr10 | 156,308,133 | T | T | C | C |
| dfreq10 | CA10X.chr10_ 156308171 | C/T | chr10 | 156,308,171 | T | T | C | C |
| dfreq10 | CA10X.chr10_ 156308239 | C/T | chr10 | 156,308,239 | C | C | T | T |
| dfreq10 | CA10X.chr10_ 156402103 | C/A | chr10 | 156,402,103 | C | C | A | A |

-continued

| QTL | Marker | alleles | chrom | pos | Garnet | Maor | UCD14 | favorable allele |
|---|---|---|---|---|---|---|---|---|
| dfreq10 | CA10X.chr10_ | 156426013 T/G | chr10 | 156,426,013 | T | T | G | G |
| dfreq10 | CA10X.chr10_ | 156586673 A/G | chr10 | 156,586,673 | G | G | A | A |
| dfreq10 | CA10X.chr10_ | 156949128 T/C | chr10 | 156,949,128 | C | C | T | T |
| dfreq10 | CA10X.chr10_ | 157999874 C/A | chr10 | 157,999,874 | C | C | A | A |
| dfreq10 | CA10X.chr10_ | 159934779 C/A | chr10 | 159,934,779 | C | C | A | A |
| dfreq10 | CA10X.chr10_ | 160043878 T/G | chr10 | 160,043,878 | G | G | T | T |
| dfreq10 | CA10X.chr10_ | 160202582 G/T | chr10 | 160,202,582 | G | G | T | T |
| dfreq10 | CA10X.chr10_ | 161306031 T/C | chr10 | 161,306,031 | C | C | T | T |
| dfreq10 | CA10X.chr10_ | 161526273 C/A | chr10 | 161,526,273 | C | C | A | A |
| dfreq10 | CA10X.chr10_ | 162335900 C/T | chr10 | 162,335,900 | T | T | C | C |
| dfreq10 | CA10X.chr10_ | 162336111 A/G | chr10 | 162,336,111 | G | G | A | A |
| dfreq10 | CA10X.chr10_ | 162336124 G/A | chr10 | 162,336,124 | A | A | G | G |
| dfreq10 | CA10X.chr10_ | 162339027 T/C | chr10 | 162,339,027 | T | T | C | C |
| dfreq10 | CA10X.chr10_ | 162341547 G/A | chr10 | 162,341,547 | G | G | A | A |
| dfreq10 | CA10X.chr10_ | 162341612 C/T | chr10 | 162,341,612 | C | C | T | T |
| dfreq10 | CA10X.chr10_ | 162384037 C/T | chr10 | 162,384,037 | C | C | T | T |
| dfreq10 | CA10X.chr10_ | 162384093 A/G | chr10 | 162,384,093 | A | A | G | G |
| dfreq10 | CA10X.chr10_ | 162384393 T/A | chr10 | 162,384,393 | T | T | A | A |
| dfreq10 | CA10X.chr10_ | 162384418 C/T | chr10 | 162,384,418 | T | T | C | C |
| dfreq10 | CA10X.chr10_ | 162444498 A/G | chr10 | 162,444,498 | A | A | G | G |
| dfreq10 | CA10X.chr10_ | 162447148 T/C | chr10 | 162,447,148 | C | C | T | T |
| dfreq10 | CA10X.chr10_ | 162447179 G/A | chr10 | 162,447,179 | G | G | A | A |
| dfreq10 | CA10X.chr10_ | 162447180 G/T | chr10 | 162,447,180 | T | T | G | G |
| dfreq10 | CA10X.chr10_ | 162482888 C/T | chr10 | 162,482,888 | C | C | T | T |
| dfreq10 | CA10X.chr10_ | 162503535 C/T | chr10 | 162,503,535 | T | T | C | C |
| dfreq10 | CA10X.chr10_ | 162507008 G/A | chr10 | 162,507,008 | A | A | G | G |
| dfreq10 | CA10X.chr10_ | 162507066 T/C | chr10 | 162,507,066 | C | C | T | T |
| dfreq10 | CA10X.chr10_ | 162557111 C/T | chr10 | 162,557,111 | C | C | T | T |
| dfreq10 | CA10X.chr10_ | 162557159 A/G | chr10 | 162,557,159 | G | G | A | A |
| dfreq10 | CA10X.chr10_ | 162564940 A/G | chr10 | 162,564,940 | G | G | A | A |
| dfreq10 | CA10X.chr10_ | 162564943 T/C | chr10 | 162,564,943 | C | C | T | T |
| dfreq10 | CA10X.chr10_ | 162593708 T/C | chr10 | 162,593,708 | C | C | T | T |
| dfreq10 | CA10X.chr10_ | 162595712 G/C | chr10 | 162,595,712 | G | G | C | C |
| dfreq10 | CA10X.chr10_ | 162610407 C/T | chr10 | 162,610,407 | C | C | T | T |
| dfreq10 | CA10X.chr10_ | 162610550 T/C | chr10 | 162,610,550 | C | C | T | T |
| dfreq10 | CA10X.chr10_ | 162642844 C/T | chr10 | 162,642,844 | C | C | T | T |
| dfreq10 | CA10X.chr10_ | 162670064 C/T | chr10 | 162,670,064 | C | C | T | T |
| dfreq10 | CA10X.chr10_ | 162720736 G/A | chr10 | 162,720,736 | G | G | A | A |
| dfreq10 | CA10X.chr10_ | 162730549 T/G | chr10 | 162,730,549 | T | T | G | G |
| dfreq10 | CA10X.chr10_ | 162730551 T/A | chr10 | 162,730,551 | T | T | A | A |
| dfreq10 | CA10X.chr10_ | 162730601 G/C | chr10 | 162,730,601 | C | C | G | G |
| dfreq10 | CA10X.chr10_ | 162739494 A/C | chr10 | 162,739,494 | C | C | A | A |
| dfreq10 | CA10X.chr10_ | 162739547 T/C | chr10 | 162,739,547 | T | T | C | C |
| dfreq10 | CA10X.chr10_ | 162755757 A/G | chr10 | 162,755,757 | G | G | A | A |
| dfreq10 | CA10X.chr10_ | 162755877 C/T | chr10 | 162,755,877 | C | C | T | T |
| dfreq10 | CA10X.chr10_ | 162761278 T/C | chr10 | 162,761,278 | C | C | T | T |
| dfreq10 | CA10X.chr10_ | 162794927 C/T | chr10 | 162,794,927 | C | C | T | T |
| dfreq10 | CA10X.chr10_ | 162794961 C/G | chr10 | 162,794,961 | G | G | C | C |
| dfreq10 | CA10X.chr10_ | 162794975 G/A | chr10 | 162,794,975 | A | A | G | G |
| dfreq10 | CA10X.chr10_ | 162801344 T/C | chr10 | 162,801,344 | T | T | C | C |
| dfreq10 | CA10X.chr10_ | 162802265 A/T | chr10 | 162,802,265 | A | A | T | T |
| dfreq10 | CA10X.chr10_ | 162824865 T/G | chr10 | 162,824,865 | T | T | G | G |
| dfreq10 | CA10X.chr10_ | 162824964 C/T | chr10 | 162,824,964 | C | C | T | T |
| dfreq10 | CA10X.chr10_ | 162826357 T/A | chr10 | 162,826,357 | T | T | A | A |
| dfreq10 | CA10X.chr10_ | 162829605 C/T | chr10 | 162,829,605 | C | C | T | T |
| dfreq10 | CA10X.chr10_ | 162829608 A/G | chr10 | 162,829,608 | A | A | G | G |
| dfreq10 | CA10X.chr10_ | 162829646 G/A | chr10 | 162,829,646 | G | G | A | A |
| dfreq10 | CA10X.chr10_ | 162832370 A/G | chr10 | 162,832,370 | G | G | A | A |
| dfreq10 | CA10X.chr10_ | 162832633 T/C | chr10 | 162,832,633 | C | C | T | T |
| dfreq10 | CA10X.chr10_ | 162845431 T/C | chr10 | 162,845,431 | T | T | C | C |
| dfreq10 | CA10X.chr10_ | 162845442 T/C | chr10 | 162,845,442 | C | C | T | T |
| dfreq10 | CA10X.chr10_ | 162848705 G/A | chr10 | 162,848,705 | A | A | G | G |
| dfreq10 | CA10X.chr10_ | 162853210 C/A | chr10 | 162,853,210 | C | C | A | A |
| dfreq10 | CA10X.chr10_ | 162853228 T/C | chr10 | 162,853,228 | C | C | T | T |
| dfreq10 | CA10X.chr10_ | 162854551 A/G | chr10 | 162,854,551 | A | A | G | G |
| dfreq10 | CA10X.chr10_ | 162854578 C/T | chr10 | 162,854,578 | T | T | C | C |
| dfreq10 | CA10X.chr10_ | 162854583 T/C | chr10 | 162,854,583 | C | C | T | T |
| dfreq10 | CA10X.chr10_ | 162854727 A/G | chr10 | 162,854,727 | G | G | A | A |
| dfreq10 | CA10X.chr10_ | 162854738 A/G | chr10 | 162,854,738 | G | G | A | A |
| dfreq10 | CA10X.chr10_ | 162861230 A/G | chr10 | 162,861,230 | G | G | A | A |
| dfreq10 | CA10X.chr10_ | 162861281 A/G | chr10 | 162,861,281 | G | G | A | A |
| dfreq10 | CA10X.chr10_ | 162892825 T/A | chr10 | 162,892,825 | A | A | T | T |
| dfreq10 | CA10X.chr10_ | 162892924 A/T | chr10 | 162,892,924 | A | A | T | T |
| dfreq10 | CA10X.chr10_ | 162908244 T/C | chr10 | 162,908,244 | T | T | C | C |
| dfreq10 | CA10X.chr10_ | 162908265 G/A | chr10 | 162,908,265 | G | G | A | A |
| dfreq10 | CA10X.chr10_ | 162908308 G/A | chr10 | 162,908,308 | A | A | G | G |

-continued

| QTL | Marker | alleles | chrom | pos | Garnet | Maor | UCD14 | favorable allele |
|---|---|---|---|---|---|---|---|---|
| dfreq10 | CA10X.chr10_ 162918661 | G/A | chr10 | 162,918,661 | G | G | A | A |
| dfreq10 | CA10X.chr10_ 162918674 | T/A | chr10 | 162,918,674 | A | A | T | T |
| dfreq10 | CA10X.chr10_ 162918719 | C/A | chr10 | 162,918,719 | C | C | A | A |
| dfreq10 | CA10X.chr10_ 162922347 | T/A | chr10 | 162,922,347 | A | A | T | T |
| dfreq10 | CA10X.chr10_ 162926065 | A/G | chr10 | 162,926,065 | A | A | G | G |
| dfreq10 | CA10X.chr10_ 162928224 | C/T | chr10 | 162,928,224 | C | C | T | T |
| dfreq10 | CA10X.chr10_ 162931845 | C/T | chr10 | 162,931,845 | C | C | T | T |
| dfreq10 | CA10X.chr10_ 162933578 | A/G | chr10 | 162,933,578 | G | G | A | A |
| dfreq10 | CA10X.chr10_ 162933630 | T/C | chr10 | 162,933,630 | T | T | C | C |
| dfreq10 | CA10X.chr10_ 162933697 | G/T | chr10 | 162,933,697 | T | T | G | G |
| dfreq10 | CA10X.chr10_ 162933718 | A/G | chr10 | 162,933,718 | A | A | G | G |
| dfreq10 | CA10X.chr10_ 162934655 | G/T | chr10 | 162,934,655 | G | G | T | T |
| dfreq10 | CA10X.chr10_ 162960292 | C/T | chr10 | 162,960,292 | C | C | T | T |
| dfreq10 | CA10X.chr10_ 162996136 | G/A | chr10 | 162,996,136 | A | A | G | G |
| dfreq10 | CA10X.chr10_ 162996141 | T/C | chr10 | 162,996,141 | T | T | C | C |
| dfreq10 | CA10X.chr10_ 162996158 | A/C | chr10 | 162,996,158 | C | C | A | A |
| dfreq10 | CA10X.chr10_ 162996162 | G/T | chr10 | 162,996,162 | T | T | G | G |
| dfreq10 | CA10X.chr10_ 162996323 | A/G | chr10 | 162,996,323 | A | A | G | G |
| dfreq10 | CA10X.chr10_ 162996372 | G/A | chr10 | 162,996,372 | G | G | A | A |
| dfreq10 | CA10X.chr10_ 162996427 | C/T | chr10 | 162,996,427 | T | T | C | C |
| dfreq10 | CA10X.chr10_ 163004348 | A/G | chr10 | 163,004,348 | G | G | A | A |
| dfreq10 | CA10X.chr10_ 163004364 | T/C | chr10 | 163,004,364 | T | T | C | C |
| dfreq10 | CA10X.chr10_ 163004370 | T/G | chr10 | 163,004,370 | G | G | T | T |
| dfreq10 | CA10X.chr10_ 163004460 | T/A | chr10 | 163,004,460 | A | A | T | T |
| dfreq10 | CA10X.chr10_ 163019471 | G/A | chr10 | 163,019,471 | A | A | G | G |
| dfreq10 | CA10X.chr10_ 163019533 | G/C | chr10 | 163,019,533 | G | G | C | C |
| dfreq10 | CA10X.chr10_ 163019616 | A/C | chr10 | 163,019,616 | A | A | C | C |
| dfreq10 | CA10X.chr10_ 163019763 | A/C | chr10 | 163,019,763 | A | A | C | C |
| dfreq10 | CA10X.chr10_ 163021708 | C/A | chr10 | 163,021,708 | A | A | C | C |
| dfreq10 | CA10X.chr10_ 163182596 | C/T | chr10 | 163,182,596 | C | C | T | T |
| dfreq10 | CA10X.chr10_ 164002217 | A/G | chr10 | 164,002,217 | G | G | A | A |
| dfreq10 | CA10X.chr10_ 164002243 | C/T | chr10 | 164,002,243 | C | C | T | T |
| dfreq10 | CA10X.chr10_ 164002262 | G/T | chr10 | 164,002,262 | T | T | G | G |
| dfreq10 | CA10X.chr10_ 164006069 | C/T | chr10 | 164,006,069 | C | C | T | T |
| dfreq10 | CA10X.chr10_ 164006718 | A/C | chr10 | 164,006,718 | C | C | A | A |
| dfreq10 | CA10X.chr10_ 164009407 | A/C | chr10 | 164,009,407 | C | C | A | A |
| dfreq10 | CA10X.chr10_ 164010014 | T/G | chr10 | 164,010,014 | T | T | G | G |
| dfreq10 | CA10X.chr10_ 164010028 | T/C | chr10 | 164,010,028 | C | C | T | T |
| dfreq10 | CA10X.chr10_ 169743726 | A/G | chr10 | 169,743,726 | G | G | A | A |
| dfreq10 | CA10X.chr10_ 169743747 | A/G | chr10 | 169,743,747 | G | G | A | A |
| dfreq10 | CA10X.chr10_ 169743761 | C/T | chr10 | 169,743,761 | T | T | C | C |
| dfreq10 | CA10X.chr10_ 169743768 | T/C | chr10 | 169,743,768 | T | T | C | C |
| dfreq10 | CA10X.chr10_ 169743771 | A/G | chr10 | 169,743,771 | G | G | A | A |
| dfreq10 | CA10X.chr10_ 169744755 | G/C | chr10 | 169,744,755 | C | C | G | G |
| dfreq10 | CA10X.chr10_ 169744775 | C/A | chr10 | 169,744,775 | C | C | A | A |
| dfreq10 | CA10X.chr10_ 169744829 | T/C | chr10 | 169,744,829 | T | T | C | C |
| dfreq10 | CA10X.chr10_ 169744879 | T/G | chr10 | 169,744,879 | T | T | G | G |
| dfreq10 | CA10X.chr10_ 169744908 | C/T | chr10 | 169,744,908 | C | C | T | T |
| dfreq10 | CA10X.chr10_ 169744912 | C/A | chr10 | 169,744,912 | C | C | A | A |
| dfreq10 | CA10X.chr10_ 169758616 | T/C | chr10 | 169,758,616 | T | T | C | C |
| dfreq10 | CA10X.chr10_ 169761405 | A/G | chr10 | 169,761,405 | G | G | A | A |
| dfreq10 | CA10X.chr10_ 169778176 | C/A | chr10 | 169,778,176 | C | C | A | A |
| dfreq10 | CA10X.chr10_ 169778236 | C/T | chr10 | 169,778,236 | T | T | C | C |
| dfreq10 | CA10X.chr10_ 169784358 | G/A | chr10 | 169,784,358 | G | G | A | A |
| dfreq10 | CA10X.chr10_ 169785060 | A/G | chr10 | 169,785,060 | A | A | G | G |
| dfreq10 | CA10X.chr10_ 170432724 | A/G | chr10 | 170,432,724 | A | A | G | G |
| dfreq10 | CA10X.chr10_ 170432772 | C/T | chr10 | 170,432,772 | C | C | T | T |
| dfreq10 | CA10X.chr10_ 170462828 | C/T | chr10 | 170,462,828 | C | C | T | T |
| dfreq10 | CA10X.chr10_ 170462829 | T/C | chr10 | 170,462,829 | C | C | T | T |
| dfreq10 | CA10X.chr10_ 170480936 | G/A | chr10 | 170,480,936 | A | A | G | G |
| dfreq10 | CA10X.chr10_ 170482404 | C/T | chr10 | 170,482,404 | C | C | T | T |
| dfreq10 | CA10X.chr10_ 170487078 | G/A | chr10 | 170,487,078 | A | A | G | G |
| dfreq10 | CA10X.chr10_ 170487106 | T/C | chr10 | 170,487,106 | T | T | C | C |
| dfreq10 | CA10X.chr10_ 170488990 | T/C | chr10 | 170,488,990 | T | T | C | C |
| dfreq10 | CA10X.chr10_ 170489090 | C/T | chr10 | 170,489,090 | T | T | C | C |
| dfreq10 | CA10X.chr10_ 170490757 | C/G | chr10 | 170,490,757 | C | C | G | G |
| dfreq10 | CA10X.chr10_ 170490758 | C/T | chr10 | 170,490,758 | T | T | C | C |
| dfreq10 | CA10X.chr10_ 170490776 | G/A | chr10 | 170,490,776 | A | A | G | G |
| dfreq10 | CA10X.chr10_ 170490833 | A/C | chr10 | 170,490,833 | C | C | A | A |
| dfreq10 | CA10X.chr10_ 170491066 | T/C | chr10 | 170,491,066 | C | C | T | T |
| dfreq10 | CA10X.chr10_ 170491616 | G/C | chr10 | 170,491,616 | G | G | C | C |
| dfreq10 | CA10X.chr10_ 170493894 | C/T | chr10 | 170,493,894 | T | T | C | C |
| dfreq10 | CA10X.chr10_ 170496521 | A/G | chr10 | 170,496,521 | G | G | A | A |
| dfreq10 | CA10X.chr10_ 170496576 | T/C | chr10 | 170,496,576 | C | C | T | T |
| dfreq10 | CA10X.chr10_ 170507404 | T/C | chr10 | 170,507,404 | T | T | C | C |
| dfreq10 | CA10X.chr10_ 170507651 | C/T | chr10 | 170,507,651 | C | C | T | T |

-continued

| QTL | Marker | alleles | chrom | pos | Garnet | Maor | UCD14 | favorable allele |
|---|---|---|---|---|---|---|---|---|
| dfreq10 | CA10X.chr10_ 170507661 | C/T | chr10 | 170,507,661 | C | C | T | T |
| dfreq10 | CA10X.chr10_ 170543688 | C/T | chr10 | 170,543,688 | C | C | T | T |
| dfreq10 | CA10X.chr10_ 170543724 | T/A | chr10 | 170,543,724 | T | T | A | A |
| dfreq10 | CA10X.chr10_ 170543727 | C/T | chr10 | 170,543,727 | T | T | C | C |
| dfreq10 | CA10X.chr10_ 170543816 | C/T | chr10 | 170,543,816 | C | C | T | T |
| dfreq10 | CA10X.chr10_ 170559250 | C/T | chr10 | 170,559,250 | C | C | T | T |
| dfreq10 | CA10X.chr10_ 170559964 | A/C | chr10 | 170,559,964 | A | A | C | C |
| dfreq10 | CA10X.chr10_ 170561799 | T/G | chr10 | 170,561,799 | T | T | G | G |
| dfreq10 | CA10X.chr10_ 170580492 | T/G | chr10 | 170,580,492 | G | G | T | T |
| dfreq10 | CA10X.chr10_ 170580575 | G/A | chr10 | 170,580,575 | G | G | A | A |
| dfreq10 | CA10X.chr10_ 170580587 | C/T | chr10 | 170,580,587 | C | C | T | T |
| dfreq10 | CA10X.chr10_ 170580734 | A/G | chr10 | 170,580,734 | G | G | A | A |
| dfreq10 | CA10X.chr10_ 170609353 | A/C | chr10 | 170,609,353 | A | A | C | C |
| dfreq10 | CA10X.chr10_ 170609362 | T/C | chr10 | 170,609,362 | T | T | C | C |
| dfreq10 | CA10X.chr10_ 170609474 | C/T | chr10 | 170,609,474 | C | C | T | T |
| dfreq10 | CA10X.chr10_ 170609497 | G/T | chr10 | 170,609,497 | T | T | G | G |
| dfreq10 | CA10X.chr10_ 170609522 | A/G | chr10 | 170,609,522 | G | G | A | A |
| dfreq10 | CA10X.chr10_ 170609558 | T/C | chr10 | 170,609,558 | T | T | C | C |
| dfreq10 | CA10X.chr10_ 170609794 | A/C | chr10 | 170,609,794 | C | C | A | A |
| dfreq10 | CA10X.chr10_ 170619221 | C/G | chr10 | 170,619,221 | C | C | G | G |
| dfreq10 | CA10X.chr10_ 170619269 | T/C | chr10 | 170,619,269 | T | T | C | C |
| dfreq10 | CA10X.chr10_ 170619279 | C/T | chr10 | 170,619,279 | C | C | T | T |
| dfreq10 | CA10X.chr10_ 170619344 | G/A | chr10 | 170,619,344 | A | A | G | G |
| dfreq10 | CA10X.chr10_ 170619355 | T/G | chr10 | 170,619,355 | G | G | T | T |
| dfreq10 | CA10X.chr10_ 170619421 | C/G | chr10 | 170,619,421 | C | C | G | G |
| dfreq10 | CA10X.chr10_ 170619451 | G/A | chr10 | 170,619,451 | G | G | A | A |
| dfreq10 | CA10X.chr10_ 170619459 | T/C | chr10 | 170,619,459 | T | T | C | C |
| dfreq10 | CA10X.chr10_ 170621906 | A/G | chr10 | 170,621,906 | G | G | A | A |
| dfreq10 | CA10X.chr10_ 170621934 | T/A | chr10 | 170,621,934 | T | T | A | A |
| dfreq10 | CA10X.chr10_ 170621947 | A/C | chr10 | 170,621,947 | C | C | A | A |
| dfreq10 | CA10X.chr10_ 170622212 | C/T | chr10 | 170,622,212 | T | T | C | C |
| dfreq10 | CA10X.chr10_ 170622218 | G/A | chr10 | 170,622,218 | G | G | A | A |
| dfreq10 | CA10X.chr10_ 170623507 | C/T | chr10 | 170,623,507 | T | T | C | C |
| dfreq10 | CA10X.chr10_ 170632605 | A/G | chr10 | 170,632,605 | G | G | A | A |
| dfreq10 | CA10X.chr10_ 170632608 | G/A | chr10 | 170,632,608 | A | A | G | G |
| dfreq10 | CA10X.chr10_ 170632708 | G/A | chr10 | 170,632,708 | G | G | A | A |
| dfreq10 | CA10X.chr10_ 170632825 | T/C | chr10 | 170,632,825 | T | T | C | C |
| dfreq10 | CA10X.chr10_ 170632864 | C/T | chr10 | 170,632,864 | T | T | C | C |
| dfreq10 | CA10X.chr10_ 170634609 | G/T | chr10 | 170,634,609 | G | G | T | T |
| dfreq10 | CA10X.chr10_ 170634826 | G/A | chr10 | 170,634,826 | G | G | A | A |
| dfreq10 | CA10X.chr10_ 170634876 | T/C | chr10 | 170,634,876 | C | C | T | T |
| dfreq10 | CA10X.chr10_ 170635818 | A/G | chr10 | 170,635,818 | G | G | A | A |
| dfreq10 | CA10X.chr10_ 170635853 | A/C | chr10 | 170,635,853 | C | C | A | A |
| dfreq10 | CA10X.chr10_ 170635920 | G/A | chr10 | 170,635,920 | A | A | G | G |
| dfreq10 | CA10X.chr10_ 170636166 | C/T | chr10 | 170,636,166 | C | C | T | T |
| dfreq10 | CA10X.chr10_ 170636304 | T/A | chr10 | 170,636,304 | T | T | A | A |
| dfreq10 | CA10X.chr10_ 170638591 | T/C | chr10 | 170,638,591 | T | T | C | C |
| dfreq10 | CA10X.chr10_ 170638637 | G/A | chr10 | 170,638,637 | G | G | A | A |
| dfreq10 | CA10X.chr10_ 170638646 | A/G | chr10 | 170,638,646 | G | G | A | A |
| dfreq10 | CA10X.chr10_ 170646955 | C/A | chr10 | 170,646,955 | C | C | A | A |
| dfreq10 | CA10X.chr10_ 170646983 | A/G | chr10 | 170,646,983 | G | G | A | A |
| dfreq10 | CA10X.chr10_ 170647193 | C/T | chr10 | 170,647,193 | T | T | C | C |
| dfreq10 | CA10X.chr10_ 170652302 | T/C | chr10 | 170,652,302 | T | T | C | C |
| dfreq10 | CA10X.chr10_ 170653272 | T/C | chr10 | 170,653,272 | C | C | T | T |
| dfreq10 | CA10X.chr10_ 170653286 | A/G | chr10 | 170,653,286 | A | A | G | G |
| dfreq10 | CA10X.chr10_ 170653335 | G/A | chr10 | 170,653,335 | A | A | G | G |
| dfreq10 | CA10X.chr10_ 170653338 | A/G | chr10 | 170,653,338 | G | G | A | A |
| dfreq10 | CA10X.chr10_ 170665684 | C/T | chr10 | 170,665,684 | C | C | T | T |
| dfreq10 | CA10X.chr10_ 170683836 | A/T | chr10 | 170,683,836 | T | T | A | A |
| dfreq10 | CA10X.chr10_ 170690325 | A/G | chr10 | 170,690,325 | G | G | A | A |
| dfreq10 | CA10X.chr10_ 170690329 | A/G | chr10 | 170,690,329 | G | G | A | A |
| dfreq10 | CA10X.chr10_ 170690493 | A/G | chr10 | 170,690,493 | A | A | G | G |
| dfreq10 | CA10X.chr10_ 170690525 | C/T | chr10 | 170,690,525 | T | T | C | C |
| dfreq10 | CA10X.chr10_ 170695316 | G/C | chr10 | 170,695,316 | C | C | G | G |
| dfreq10 | CA10X.chr10_ 170695396 | T/C | chr10 | 170,695,396 | C | C | T | T |
| dfreq10 | CA10X.chr10_ 170695472 | T/A | chr10 | 170,695,472 | T | T | A | A |
| dfreq10 | CA10X.chr10_ 170706611 | T/G | chr10 | 170,706,611 | T | T | G | G |
| dfreq10 | CA10X.chr10_ 170715723 | C/T | chr10 | 170,715,723 | T | T | C | C |
| dfreq10 | CA10X.chr10_ 170715765 | T/C | chr10 | 170,715,765 | C | C | T | T |
| dfreq10 | CA10X.chr10_ 170716349 | C/T | chr10 | 170,716,349 | C | C | T | T |
| dfreq10 | CA10X.chr10_ 170717809 | T/C | chr10 | 170,717,809 | T | T | C | C |
| dfreq10 | CA10X.chr10_ 170717852 | A/T | chr10 | 170,717,852 | T | T | A | A |
| dfreq10 | CA10X.chr10_ 170726584 | C/T | chr10 | 170,726,584 | T | T | C | C |
| dfreq10 | CA10X.chr10_ 170726619 | T/C | chr10 | 170,726,619 | C | C | T | T |
| dfreq10 | CA10X.chr10_ 170726629 | C/T | chr10 | 170,726,629 | T | T | C | C |
| dfreq10 | CA10X.chr10_ 170727031 | G/T | chr10 | 170,727,031 | G | G | T | T |

-continued

| QTL | Marker | alleles | chrom | pos | Garnet | Maor | UCD14 | favorable allele |
|---|---|---|---|---|---|---|---|---|
| dfreq10 | CA10X.chr10_ 170727036 T/C | chr10 | 170,727,036 | T | T | C | C |
| dfreq10 | CA10X.chr10_ 170727048 A/G | chr10 | 170,727,048 | A | A | G | G |
| dfreq10 | CA10X.chr10_ 170727156 G/T | chr10 | 170,727,156 | G | G | T | T |
| dfreq10 | CA10X.chr10_ 170728170 C/A | chr10 | 170,728,170 | C | C | A | A |
| dfreq10 | CA10X.chr10_ 170728252 A/T | chr10 | 170,728,252 | T | T | A | A |
| dfreq10 | CA10X.chr10_ 170742905 T/C | chr10 | 170,742,905 | C | C | T | T |
| dfreq10 | CA10X.chr10_ 170742910 C/T | chr10 | 170,742,910 | C | C | T | T |
| dfreq10 | CA10X.chr10_ 170743106 C/A | chr10 | 170,743,106 | C | C | A | A |
| dfreq10 | CA10X.chr10_ 170743133 G/A | chr10 | 170,743,133 | A | A | G | G |
| dfreq10 | CA10X.chr10_ 170743134 A/C | chr10 | 170,743,134 | A | A | C | C |
| dfreq10 | CA10X.chr10_ 170750100 G/T | chr10 | 170,750,100 | G | G | T | T |
| dfreq10 | CA10X.chr10_ 170750110 T/C | chr10 | 170,750,110 | C | C | T | T |
| dfreq10 | CA10X.chr10_ 170752386 G/A | chr10 | 170,752,386 | G | G | A | A |
| dfreq10 | CA10X.chr10_ 170752449 C/A | chr10 | 170,752,449 | C | C | A | A |
| dfreq10 | CA10X.chr10_ 170754228 A/C | chr10 | 170,754,228 | C | C | A | A |
| dfreq10 | CA10X.chr10_ 170754309 A/C | chr10 | 170,754,309 | A | A | C | C |
| dfreq10 | CA10X.chr10_ 170754315 C/T | chr10 | 170,754,315 | C | C | T | T |
| dfreq10 | CA10X.chr10_ 170756871 A/T | chr10 | 170,756,871 | A | A | T | T |
| dfreq10 | CA10X.chr10_ 170756918 G/C | chr10 | 170,756,918 | G | G | C | C |
| dfreq10 | CA10X.chr10_ 170756935 A/T | chr10 | 170,756,935 | A | A | T | T |
| dfreq10 | CA10X.chr10_ 170757000 T/A | chr10 | 170,757,000 | A | A | T | T |
| dfreq10 | CA10X.chr10_ 170757062 T/C | chr10 | 170,757,062 | T | T | C | C |
| dfreq10 | CA10X.chr10_ 170758404 C/T | chr10 | 170,758,404 | C | C | T | T |
| dfreq10 | CA10X.chr10_ 170774599 G/A | chr10 | 170,774,599 | G | G | A | A |
| dfreq10 | CA10X.chr10_ 170777234 T/G | chr10 | 170,777,234 | G | G | T | T |
| dfreq10 | CA10X.chr10_ 170777406 A/G | chr10 | 170,777,406 | G | G | A | A |
| dfreq10 | CA10X.chr10_ 170779821 A/G | chr10 | 170,779,821 | A | A | G | G |
| dfreq10 | CA10X.chr10_ 170806877 C/G | chr10 | 170,806,877 | G | G | C | C |
| dfreq10 | CA10X.chr10_ 170817787 A/C | chr10 | 170,817,787 | C | C | A | A |
| dfreq10 | CA10X.chr10_ 170818362 C/T | chr10 | 170,818,362 | C | C | T | T |
| dfreq10 | CA10X.chr10_ 170819709 G/C | chr10 | 170,819,709 | G | G | C | C |
| dfreq10 | CA10X.chr10_ 170819751 A/T | chr10 | 170,819,751 | A | A | T | T |
| dfreq10 | CA10X.chr10_ 170822928 A/G | chr10 | 170,822,928 | A | A | G | G |
| dfreq10 | CA10X.chr10_ 170824914 T/C | chr10 | 170,824,914 | C | C | T | T |
| dfreq10 | CA10X.chr10_ 170825015 T/G | chr10 | 170,825,015 | G | G | T | T |
| dfreq10 | CA10X.chr10_ 170825016 A/T | chr10 | 170,825,016 | T | T | A | A |
| dfreq10 | CA10X.chr10_ 170828583 A/C | chr10 | 170,828,583 | A | A | C | C |
| dfreq10 | CA10X.chr10_ 170836679 T/G | chr10 | 170,836,679 | G | G | T | T |
| dfreq10 | CA10X.chr10_ 170836754 T/C | chr10 | 170,836,754 | C | C | T | T |
| dfreq10 | CA10X.chr10_ 170836777 T/C | chr10 | 170,836,777 | T | T | C | C |
| dfreq10 | CA10X.chr10_ 170840981 A/G | chr10 | 170,840,981 | G | G | A | A |
| dfreq10 | CA10X.chr10_ 170861582 G/A | chr10 | 170,861,582 | G | G | A | A |
| dfreq10 | CA10X.chr10_ 170861639 A/G | chr10 | 170,861,639 | G | G | A | A |
| dfreq10 | CA10X.chr10_ 170862459 G/A | chr10 | 170,862,459 | G | G | A | A |
| dfreq10 | CA10X.chr10_ 170862568 A/G | chr10 | 170,862,568 | G | G | A | A |
| dfreq10 | CA10X.chr10_ 170862632 A/G | chr10 | 170,862,632 | A | A | G | G |
| dfreq10 | CA10X.chr10_ 170862664 G/A | chr10 | 170,862,664 | A | A | G | G |
| dfreq10 | CA10X.chr10_ 170862739 A/C | chr10 | 170,862,739 | C | C | A | A |
| dfreq10 | CA10X.chr10_ 170862780 G/A | chr10 | 170,862,780 | A | A | G | G |
| dfreq10 | CA10X.chr10_ 170868292 C/A | chr10 | 170,868,292 | A | A | C | C |
| dfreq10 | CA10X.chr10_ 170869575 A/G | chr10 | 170,869,575 | A | A | G | G |
| dfreq10 | CA10X.chr10_ 170869601 A/G | chr10 | 170,869,601 | G | G | A | A |
| dfreq10 | CA10X.chr10_ 170901615 T/C | chr10 | 170,901,615 | T | T | C | C |
| dfreq10 | CA10X.chr10_ 170914987 A/T | chr10 | 170,914,987 | A | A | T | T |
| dfreq10 | CA10X.chr10_ 170915083 C/T | chr10 | 170,915,083 | C | C | T | T |
| dfreq10 | CA10X.chr10_ 170915436 G/A | chr10 | 170,915,436 | A | A | G | G |
| dfreq10 | CA10X.chr10_ 170915595 C/A | chr10 | 170,915,595 | C | C | A | A |
| dfreq10 | CA10X.chr10_ 170917693 C/T | chr10 | 170,917,693 | C | C | T | T |
| dfreq10 | CA10X.chr10_ 170917894 C/T | chr10 | 170,917,894 | T | T | C | C |
| dfreq10 | CA10X.chr10_ 170919957 T/C | chr10 | 170,919,957 | C | C | T | T |
| dfreq10 | CA10X.chr10_ 170933151 A/C | chr10 | 170,933,151 | C | C | A | A |
| dfreq10 | CA10X.chr10_ 170934468 T/C | chr10 | 170,934,468 | C | C | T | T |
| dfreq10 | CA10X.chr10_ 170934564 T/G | chr10 | 170,934,564 | T | T | G | G |
| dfreq10 | CA10X.chr10_ 170938893 T/C | chr10 | 170,938,893 | T | T | C | C |
| dfreq10 | CA10X.chr10_ 170954503 G/A | chr10 | 170,954,503 | A | A | G | G |
| dfreq10 | CA10X.chr10_ 170954535 A/G | chr10 | 170,954,535 | G | G | A | A |
| dfreq10 | CA10X.chr10_ 170960003 G/A | chr10 | 170,960,003 | A | A | G | G |
| dfreq10 | CA10X.chr10_ 170963927 C/T | chr10 | 170,963,927 | C | C | T | T |
| dfreq10 | CA10X.chr10_ 170964125 T/C | chr10 | 170,964,125 | C | C | T | T |
| dfreq10 | CA10X.chr10_ 170966217 C/A | chr10 | 170,966,217 | C | C | A | A |
| dfreq10 | CA10X.chr10_ 170966286 C/A | chr10 | 170,966,286 | C | C | A | A |
| dfreq10 | CA10X.chr10_ 170966334 T/C | chr10 | 170,966,334 | T | T | C | C |
| dfreq10 | CA10X.chr10_ 170966458 A/C | chr10 | 170,966,458 | A | A | C | C |
| dfreq10 | CA10X.chr10_ 170966639 T/C | chr10 | 170,966,639 | T | T | C | C |
| dfreq10 | CA10X.chr10_ 170966677 T/A | chr10 | 170,966,677 | A | A | T | T |
| dfreq10 | CA10X.chr10_ 170970668 A/G | chr10 | 170,970,668 | A | A | G | G |

-continued

| QTL | Marker | alleles | chrom | pos | Garnet | Maor | UCD14 | favorable allele |
|---|---|---|---|---|---|---|---|---|
| dfreq10 | CA10X.chr10_ | 170976855 A/G | chr10 | 170,976,855 | A | A | G | G |
| dfreq10 | CA10X.chr10_ | 170976904 G/A | chr10 | 170,976,904 | G | G | A | A |
| dfreq10 | CA10X.chr10_ | 170988468 C/T | chr10 | 170,988,468 | T | T | C | C |
| dfreq10 | CA10X.chr10_ | 170988656 T/C | chr10 | 170,988,656 | T | T | C | C |
| dfreq10 | CA10X.chr10_ | 170993875 T/C | chr10 | 170,993,875 | C | C | T | T |
| dfreq10 | CA10X.chr10_ | 171003091 A/G | chr10 | 171,003,091 | A | A | G | G |
| dfreq10 | CA10X.chr10_ | 171003186 G/A | chr10 | 171,003,186 | G | G | A | A |
| dfreq10 | CA10X.chr10_ | 171011391 A/G | chr10 | 171,011,391 | G | G | A | A |
| dfreq10 | CA10X.chr10_ | 171011483 G/A | chr10 | 171,011,483 | A | A | G | G |
| dfreq10 | CA10X.chr10_ | 171012636 A/G | chr10 | 171,012,636 | A | A | G | G |
| dfreq10 | CA10X.chr10_ | 171012657 C/G | chr10 | 171,012,657 | G | G | C | C |
| dfreq10 | CA10X.chr10_ | 171017014 T/A | chr10 | 171,017,014 | A | A | T | T |
| dfreq10 | CA10X.chr10_ | 171017268 A/G | chr10 | 171,017,268 | G | G | A | A |
| dfreq10 | CA10X.chr10_ | 171020133 A/G | chr10 | 171,020,133 | G | G | A | A |
| dfreq10 | CA10X.chr10_ | 171027749 T/A | chr10 | 171,027,749 | A | A | T | T |
| dfreq10 | CA10X.chr10_ | 171036489 C/T | chr10 | 171,036,489 | C | C | T | T |
| dfreq10 | CA10X.chr10_ | 171177832 T/C | chr10 | 171,177,832 | C | C | T | T |
| dfreq10 | CA10X.chr10_ | 171177919 T/C | chr10 | 171,177,919 | C | C | T | T |
| dfreq10 | CA10X.chr10_ | 171290398 G/A | chr10 | 171,290,398 | A | A | G | G |
| dfreq10 | CA10X.chr10_ | 171367003 T/G | chr10 | 171,367,003 | G | G | T | T |
| dfreq10 | CA10X.chr10_ | 171607949 G/A | chr10 | 171,607,949 | G | G | A | A |
| dfreq10 | CA10X.chr10_ | 171719975 T/C | chr10 | 171,719,975 | T | T | C | C |
| dfreq10 | CA10X.chr10_ | 172099127 C/T | chr10 | 172,099,127 | T | T | C | C |
| dfreq10 | CA10X.chr10_ | 172867573 T/G | chr10 | 172,867,573 | G | G | T | T |
| dfreq10 | CA10X.chr10_ | 172884853 T/C | chr10 | 172,884,853 | C | C | T | T |
| dfreq10 | CA10X.chr10_ | 172931574 C/G | chr10 | 172,931,574 | C | C | G | G |
| dfreq10 | CA10X.chr10_ | 172942844 A/C | chr10 | 172,942,844 | C | C | A | A |
| dfreq10 | CA10X.chr10_ | 172944895 T/G | chr10 | 172,944,895 | G | G | T | T |
| dfreq10 | CA10X.chr10_ | 172956805 A/T | chr10 | 172,956,805 | A | A | T | T |
| dfreq10 | CA10X.chr10_ | 172965002 C/T | chr10 | 172,965,002 | C | C | T | T |
| dfreq10 | CA10X.chr10_ | 172965007 C/T | chr10 | 172,965,007 | T | T | C | C |
| dfreq10 | CA10X.chr10_ | 172965029 T/G | chr10 | 172,965,029 | T | T | G | G |
| dfreq10 | CA10X.chr10_ | 172967064 G/A | chr10 | 172,967,064 | G | G | A | A |
| dfreq10 | CA10X.chr10_ | 172967120 G/A | chr10 | 172,967,120 | G | G | A | A |
| dfreq10 | CA10X.chr10_ | 172967251 G/A | chr10 | 172,967,251 | A | A | G | G |
| dfreq10 | CA10X.chr10_ | 172975906 C/T | chr10 | 172,975,906 | C | C | T | T |
| dfreq10 | CA10X.chr10_ | 172975912 G/A | chr10 | 172,975,912 | G | G | A | A |
| dfreq10 | CA10X.chr10_ | 172975927 G/A | chr10 | 172,975,927 | A | A | G | G |
| dfreq10 | CA10X.chr10_ | 172975930 G/A | chr10 | 172,975,930 | G | G | A | A |
| dfreq10 | CA10X.chr10_ | 172975958 A/G | chr10 | 172,975,958 | G | G | A | A |
| dfreq10 | CA10X.chr10_ | 172976108 A/G | chr10 | 172,976,108 | G | G | A | A |
| dfreq10 | CA10X.chr10_ | 172976154 G/A | chr10 | 172,976,154 | A | A | G | G |
| dfreq10 | CA10X.chr10_ | 172976171 G/A | chr10 | 172,976,171 | G | G | A | A |
| dfreq10 | CA10X.chr10_ | 172979383 T/C | chr10 | 172,979,383 | C | C | T | T |
| dfreq10 | CA10X.chr10_ | 172979619 A/G | chr10 | 172,979,619 | G | G | A | A |
| dfreq10 | CA10X.chr10_ | 172979646 G/A | chr10 | 172,979,646 | A | A | G | G |
| dfreq10 | CA10X.chr10_ | 172991745 G/A | chr10 | 172,991,745 | G | G | A | A |
| dfreq10 | CA10X.chr10_ | 172991813 C/A | chr10 | 172,991,813 | C | C | A | A |
| dfreq10 | CA10X.chr10_ | 172991847 C/A | chr10 | 172,991,847 | C | C | A | A |
| dfreq10 | CA10X.chr10_ | 173000463 A/G | chr10 | 173,000,463 | G | G | A | A |
| dfreq10 | CA10X.chr10_ | 173000553 T/A | chr10 | 173,000,553 | A | A | T | T |
| dfreq10 | CA10X.chr10_ | 173003638 G/A | chr10 | 173,003,638 | G | G | A | A |
| dfreq10 | CA10X.chr10_ | 173003664 A/T | chr10 | 173,003,664 | A | A | T | T |
| dfreq10 | CA10X.chr10_ | 173003719 G/T | chr10 | 173,003,719 | G | G | T | T |
| dfreq10 | CA10X.chr10_ | 173003725 G/A | chr10 | 173,003,725 | A | A | G | G |
| dfreq10 | CA10X.chr10_ | 173003795 T/C | chr10 | 173,003,795 | C | C | T | T |
| dfreq10 | CA10X.chr10_ | 173003807 A/G | chr10 | 173,003,807 | A | A | G | G |
| dfreq10 | CA10X.chr10_ | 173003862 C/A | chr10 | 173,003,862 | A | A | C | C |
| dfreq10 | CA10X.chr10_ | 173005340 A/G | chr10 | 173,005,340 | G | G | A | A |
| dfreq10 | CA10X.chr10_ | 173008378 A/G | chr10 | 173,008,378 | A | A | G | G |
| dfreq10 | CA10X.chr10_ | 173008432 C/T | chr10 | 173,008,432 | T | T | C | C |
| dfreq10 | CA10X.chr10_ | 173008444 G/A | chr10 | 173,008,444 | G | G | A | A |
| dfreq10 | CA10X.chr10_ | 173008457 C/A | chr10 | 173,008,457 | A | A | C | C |
| dfreq10 | CA10X.chr10_ | 173008572 T/G | chr10 | 173,008,572 | G | G | T | T |
| dfreq10 | CA10X.chr10_ | 173008622 G/A | chr10 | 173,008,622 | G | G | A | A |
| dfreq10 | CA10X.chr10_ | 173013620 G/A | chr10 | 173,013,620 | G | G | A | A |
| dfreq10 | CA10X.chr10_ | 173013697 G/C | chr10 | 173,013,697 | G | G | C | C |
| dfreq10 | CA10X.chr10_ | 173013851 A/G | chr10 | 173,013,851 | G | G | A | A |
| dfreq10 | CA10X.chr10_ | 173013869 T/G | chr10 | 173,013,869 | G | G | T | T |
| dfreq10 | CA10X.chr10_ | 173015083 G/A | chr10 | 173,015,083 | G | G | A | A |
| dfreq10 | CA10X.chr10_ | 173015181 T/C | chr10 | 173,015,181 | T | T | C | C |
| dfreq10 | CA10X.chr10_ | 173015194 T/C | chr10 | 173,015,194 | T | T | C | C |
| dfreq10 | CA10X.chr10_ | 173015339 C/T | chr10 | 173,015,339 | T | T | C | C |
| dfreq10 | CA10X.chr10_ | 173015485 A/G | chr10 | 173,015,485 | G | G | A | A |
| dfreq10 | CA10X.chr10_ | 173021015 C/T | chr10 | 173,021,015 | T | T | C | C |
| dfreq10 | CA10X.chr10_ | 173021099 C/A | chr10 | 173,021,099 | C | C | A | A |

-continued

| QTL | Marker | alleles | chrom | pos | Garnet | Maor | UCD14 | favorable allele |
|---|---|---|---|---|---|---|---|---|
| dfreq10 | CA10X.chr10_ | 173028127 G/A | chr10 | 173,028,127 | G | G | A | A |
| dfreq10 | CA10X.chr10_ | 173028129 T/C | chr10 | 173,028,129 | T | T | C | C |
| dfreq10 | CA10X.chr10_ | 173028142 C/T | chr10 | 173,028,142 | C | C | T | T |
| dfreq10 | CA10X.chr10_ | 173028229 A/G | chr10 | 173,028,229 | A | A | G | G |
| dfreq10 | CA10X.chr10_ | 173073154 A/G | chr10 | 173,073,154 | G | G | A | A |
| dfreq10 | CA10X.chr10_ | 173083178 T/C | chr10 | 173,083,178 | T | T | C | C |
| dfreq10 | CA10X.chr10_ | 173083302 C/T | chr10 | 173,083,302 | T | T | C | C |
| dfreq10 | CA10X.chr10_ | 173085850 C/T | chr10 | 173,085,850 | C | C | T | T |
| dfreq10 | CA10X.chr10_ | 173085899 C/A | chr10 | 173,085,899 | A | A | C | C |
| dfreq10 | CA10X.chr10_ | 173087018 G/A | chr10 | 173,087,018 | A | A | G | G |
| dfreq10 | CA10X.chr10_ | 173091006 C/G | chr10 | 173,091,006 | C | C | G | G |
| dfreq10 | CA10X.chr10_ | 173097556 T/C | chr10 | 173,097,556 | T | T | C | C |
| dfreq10 | CA10X.chr10_ | 173097635 G/A | chr10 | 173,097,635 | A | A | G | G |
| dfreq10 | CA10X.chr10_ | 173108417 A/T | chr10 | 173,108,417 | A | A | T | T |
| dfreq10 | CA10X.chr10_ | 173114746 T/C | chr10 | 173,114,746 | T | T | C | C |
| dfreq10 | CA10X.chr10_ | 173114982 T/C | chr10 | 173,114,982 | T | T | C | C |
| dfreq10 | CA10X.chr10_ | 173115796 G/A | chr10 | 173,115,796 | A | A | G | G |
| dfreq10 | CA10X.chr10_ | 173115863 C/T | chr10 | 173,115,863 | C | C | T | T |
| dfreq10 | CA10X.chr10_ | 173115867 G/T | chr10 | 173,115,867 | T | T | G | G |
| dfreq10 | CA10X.chr10_ | 173115913 C/T | chr10 | 173,115,913 | C | C | T | T |
| dfreq10 | CA10X.chr10_ | 173116080 C/T | chr10 | 173,116,080 | C | C | T | T |
| dfreq10 | CA10X.chr10_ | 173116121 A/T | chr10 | 173,116,121 | A | A | T | T |
| dfreq10 | CA10X.chr10_ | 173116406 A/C | chr10 | 173,116,406 | C | C | A | A |
| dfreq10 | CA10X.chr10_ | 173117265 C/G | chr10 | 173,117,265 | C | C | G | G |
| dfreq10 | CA10X.chr10_ | 173117610 C/T | chr10 | 173,117,610 | C | C | T | T |
| dfreq10 | CA10X.chr10_ | 173120093 T/C | chr10 | 173,120,093 | C | C | T | T |
| dfreq10 | CA10X.chr10_ | 173120095 T/C | chr10 | 173,120,095 | C | C | T | T |
| dfreq10 | CA10X.chr10_ | 173120120 G/A | chr10 | 173,120,120 | A | A | G | G |
| dfreq10 | CA10X.chr10_ | 173120164 A/G | chr10 | 173,120,164 | G | G | A | A |
| dfreq10 | CA10X.chr10_ | 173120173 A/T | chr10 | 173,120,173 | A | A | T | T |
| dfreq10 | CA10X.chr10_ | 173120200 G/C | chr10 | 173,120,200 | C | C | G | G |
| dfreq10 | CA10X.chr10_ | 173120452 G/A | chr10 | 173,120,452 | A | A | G | G |
| dfreq10 | CA10X.chr10_ | 173121961 A/G | chr10 | 173,121,961 | G | G | A | A |
| dfreq10 | CA10X.chr10_ | 173122045 C/T | chr10 | 173,122,045 | C | C | T | T |
| dfreq10 | CA10X.chr10_ | 173122270 C/G | chr10 | 173,122,270 | G | G | C | C |
| dfreq10 | CA10X.chr10_ | 173130878 G/T | chr10 | 173,130,878 | T | T | G | G |
| dfreq10 | CA10X.chr10_ | 173130953 C/G | chr10 | 173,130,953 | C | C | G | G |
| dfreq10 | CA10X.chr10_ | 173130980 G/A | chr10 | 173,130,980 | G | G | A | A |
| dfreq10 | CA10X.chr10_ | 173131004 T/C | chr10 | 173,131,004 | T | T | C | C |
| dfreq10 | CA10X.chr10_ | 173131072 G/T | chr10 | 173,131,072 | T | T | G | G |
| dfreq10 | CA10X.chr10_ | 173131103 T/C | chr10 | 173,131,103 | C | C | T | T |
| dfreq10 | CA10X.chr10_ | 173134314 T/G | chr10 | 173,134,314 | G | G | T | T |
| dfreq10 | CA10X.chr10_ | 173139655 A/G | chr10 | 173,139,655 | G | G | A | A |
| dfreq10 | CA10X.chr10_ | 173139721 T/C | chr10 | 173,139,721 | C | C | T | T |
| dfreq10 | CA10X.chr10_ | 173143556 G/A | chr10 | 173,143,556 | G | G | A | A |
| dfreq10 | CA10X.chr10_ | 173143635 G/A | chr10 | 173,143,635 | A | A | G | G |
| dfreq10 | CA10X.chr10_ | 173143660 A/T | chr10 | 173,143,660 | T | T | A | A |
| dfreq10 | CA10X.chr10_ | 173153930 G/A | chr10 | 173,153,930 | A | A | G | G |
| dfreq10 | CA10X.chr10_ | 173154344 G/A | chr10 | 173,154,344 | G | G | A | A |
| dfreq10 | CA10X.chr10_ | 173156120 C/G | chr10 | 173,156,120 | C | C | G | G |
| dfreq10 | CA10X.chr10_ | 173161278 T/C | chr10 | 173,161,278 | T | T | C | C |
| dfreq10 | CA10X.chr10_ | 173161297 C/G | chr10 | 173,161,297 | G | G | C | C |
| dfreq10 | CA10X.chr10_ | 173161352 G/A | chr10 | 173,161,352 | G | G | A | A |
| dfreq10 | CA10X.chr10_ | 173161414 A/G | chr10 | 173,161,414 | G | G | A | A |
| dfreq10 | CA10X.chr10_ | 173161433 C/T | chr10 | 173,161,433 | C | C | T | T |
| dfreq10 | CA10X.chr10_ | 173161568 G/T | chr10 | 173,161,568 | G | G | T | T |
| dfreq10 | CA10X.chr10_ | 173161773 T/C | chr10 | 173,161,773 | C | C | T | T |
| dfreq10 | CA10X.chr10_ | 173161774 G/A | chr10 | 173,161,774 | G | G | A | A |
| dfreq10 | CA10X.chr10_ | 173162221 G/A | chr10 | 173,162,221 | G | G | A | A |
| dfreq10 | CA10X.chr10_ | 173162325 T/C | chr10 | 173,162,325 | C | C | T | T |
| dfreq10 | CA10X.chr10_ | 173166770 A/G | chr10 | 173,166,770 | G | G | A | A |
| dfreq10 | CA10X.chr10_ | 173178444 G/T | chr10 | 173,178,444 | G | G | T | T |
| dfreq10 | CA10X.chr10_ | 173188462 A/C | chr10 | 173,188,462 | A | A | C | C |
| dfreq10 | CA10X.chr10_ | 173190191 C/T | chr10 | 173,190,191 | T | T | C | C |
| dfreq10 | CA10X.chr10_ | 173190223 C/A | chr10 | 173,190,223 | A | A | C | C |
| dfreq10 | CA10X.chr10_ | 173203292 C/A | chr10 | 173,203,292 | A | A | C | C |
| dfreq10 | CA10X.chr10_ | 173203335 T/C | chr10 | 173,203,335 | C | C | T | T |
| dfreq10 | CA10X.chr10_ | 173222912 T/A | chr10 | 173,222,912 | A | A | T | T |
| dfreq10 | CA10X.chr10_ | 173224072 T/C | chr10 | 173,224,072 | T | T | C | C |
| dfreq10 | CA10X.chr10_ | 173224190 A/G | chr10 | 173,224,190 | G | G | A | A |
| dfreq10 | CA10X.chr10_ | 173229140 T/A | chr10 | 173,229,140 | A | A | T | T |
| dfreq10 | CA10X.chr10_ | 173229318 C/T | chr10 | 173,229,318 | C | C | T | T |
| dfreq10 | CA10X.chr10_ | 173232730 T/G | chr10 | 173,232,730 | G | G | T | T |
| dfreq10 | CA10X.chr10_ | 173237440 T/C | chr10 | 173,237,440 | T | T | C | C |
| dfreq10 | CA10X.chr10_ | 173304496 C/T | chr10 | 173,304,496 | T | T | C | C |
| dfreq10 | CA10X.chr10_ | 173306568 G/A | chr10 | 173,306,568 | A | A | G | G |

-continued

| QTL | Marker | alleles | chrom | pos | Garnet | Maor | UCD14 | favorable allele |
|---|---|---|---|---|---|---|---|---|
| dfreq10 | CA10X.chr10_ | 173311747 T/C | chr10 | 173,311,747 | T | T | C | C |
| dfreq10 | CA10X.chr10_ | 173317914 T/C | chr10 | 173,317,914 | T | T | C | C |
| dfreq10 | CA10X.chr10_ | 173328304 C/T | chr10 | 173,328,304 | T | T | C | C |
| dfreq10 | CA10X.chr10_ | 173328327 A/G | chr10 | 173,328,327 | A | A | G | G |
| dfreq10 | CA10X.chr10_ | 173329072 C/T | chr10 | 173,329,072 | T | T | C | C |
| dfreq10 | CA10X.chr10_ | 173329086 G/T | chr10 | 173,329,086 | T | T | G | G |
| dfreq10 | CA10X.chr10_ | 173329097 C/T | chr10 | 173,329,097 | T | T | C | C |
| dfreq10 | CA10X.chr10_ | 173329178 T/C | chr10 | 173,329,178 | T | T | C | C |
| dfreq10 | CA10X.chr10_ | 173333721 A/G | chr10 | 173,333,721 | A | A | G | G |
| dfreq10 | CA10X.chr10_ | 173333803 C/T | chr10 | 173,333,803 | T | T | C | C |
| dfreq10 | CA10X.chr10_ | 173333809 A/G | chr10 | 173,333,809 | A | A | G | G |
| dfreq10 | CA10X.chr10_ | 173341338 G/A | chr10 | 173,341,338 | G | G | A | A |
| dfreq10 | CA10X.chr10_ | 173352292 G/A | chr10 | 173,352,292 | G | G | A | A |
| dfreq10 | CA10X.chr10_ | 173352380 A/G | chr10 | 173,352,380 | A | A | G | G |
| dfreq10 | CA10X.chr10_ | 173352502 A/G | chr10 | 173,352,502 | A | A | G | G |
| dfreq10 | CA10X.chr10_ | 173353035 A/G | chr10 | 173,353,035 | G | G | A | A |
| dfreq10 | CA10X.chr10_ | 173353091 A/T | chr10 | 173,353,091 | T | T | A | A |
| dfreq10 | CA10X.chr10_ | 173353092 A/C | chr10 | 173,353,092 | C | C | A | A |
| dfreq10 | CA10X.chr10_ | 173353102 C/T | chr10 | 173,353,102 | T | T | C | C |
| dfreq10 | CA10X.chr10_ | 173353279 T/G | chr10 | 173,353,279 | T | T | G | G |
| dfreq10 | CA10X.chr10_ | 173353287 G/A | chr10 | 173,353,287 | A | A | G | G |
| dfreq10 | CA10X.chr10_ | 173360627 G/A | chr10 | 173,360,627 | G | G | A | A |
| dfreq10 | CA10X.chr10_ | 173364369 G/C | chr10 | 173,364,369 | C | C | G | G |
| dfreq10 | CA10X.chr10_ | 173386488 T/C | chr10 | 173,386,488 | C | C | T | T |
| dfreq10 | CA10X.chr10_ | 173386800 C/A | chr10 | 173,386,800 | A | A | C | C |
| dfreq10 | CA10X.chr10_ | 173386833 G/A | chr10 | 173,386,833 | G | G | A | A |
| dfreq10 | CA10X.chr10_ | 173402897 G/A | chr10 | 173,402,897 | A | A | G | G |
| dfreq10 | CA10X.chr10_ | 173402931 A/G | chr10 | 173,402,931 | A | A | G | G |
| dfreq10 | CA10X.chr10_ | 173433154 A/C | chr10 | 173,433,154 | C | C | A | A |
| dfreq10 | CA10X.chr10_ | 173433339 T/C | chr10 | 173,433,339 | C | C | T | T |
| dfreq10 | CA10X.chr10_ | 173437083 A/T | chr10 | 173,437,083 | T | T | A | A |
| dfreq10 | CA10X.chr10_ | 173444865 C/T | chr10 | 173,444,865 | T | T | C | C |
| dfreq10 | CA10X.chr10_ | 173444930 T/C | chr10 | 173,444,930 | C | C | T | T |
| dfreq10 | CA10X.chr10_ | 173445099 C/T | chr10 | 173,445,099 | C | C | T | T |
| dfreq10 | CA10X.chr10_ | 173445134 T/C | chr10 | 173,445,134 | C | C | T | T |
| dfreq10 | CA10X.chr10_ | 173498607 A/G | chr10 | 173,498,607 | G | G | A | A |
| dfreq10 | CA10X.chr10_ | 173498617 C/T | chr10 | 173,498,617 | C | C | T | T |
| dfreq10 | CA10X.chr10_ | 173498636 A/G | chr10 | 173,498,636 | A | A | G | G |
| dfreq10 | CA10X.chr10_ | 173516688 T/C | chr10 | 173,516,688 | C | C | T | T |
| dfreq10 | CA10X.chr10_ | 173516706 C/T | chr10 | 173,516,706 | C | C | T | T |
| dfreq10 | CA10X.chr10_ | 173516836 T/G | chr10 | 173,516,836 | T | T | G | G |
| dfreq10 | CA10X.chr10_ | 173525461 A/G | chr10 | 173,525,461 | G | G | A | A |
| dfreq10 | CA10X.chr10_ | 173531820 G/C | chr10 | 173,531,820 | G | G | C | C |
| dfreq10 | CA10X.chr10_ | 173531923 C/G | chr10 | 173,531,923 | G | G | C | C |
| dfreq10 | CA10X.chr10_ | 173531932 C/T | chr10 | 173,531,932 | C | C | T | T |
| dfreq10 | CA10X.chr10_ | 173540817 T/C | chr10 | 173,540,817 | C | C | T | T |
| dfreq10 | CA10X.chr10_ | 173540917 T/A | chr10 | 173,540,917 | A | A | T | T |
| dfreq10 | CA10X.chr10_ | 173541054 G/A | chr10 | 173,541,054 | A | A | G | G |
| dfreq10 | CA10X.chr10_ | 173541108 T/C | chr10 | 173,541,108 | C | C | T | T |
| dfreq10 | CA10X.chr10_ | 173541132 G/T | chr10 | 173,541,132 | T | T | G | G |
| dfreq10 | CA10X.chr10_ | 173541179 G/A | chr10 | 173,541,179 | G | G | A | A |
| dfreq10 | CA10X.chr10_ | 173563178 C/T | chr10 | 173,563,178 | C | C | T | T |
| dfreq10 | CA10X.chr10_ | 173563280 A/G | chr10 | 173,563,280 | A | A | G | G |
| dfreq10 | CA10X.chr10_ | 173563344 A/G | chr10 | 173,563,344 | G | G | A | A |
| dfreq10 | CA10X.chr10_ | 173624757 A/G | chr10 | 173,624,757 | A | A | G | G |
| dfreq10 | CA10X.chr10_ | 173624770 A/G | chr10 | 173,624,770 | A | A | G | G |
| dfreq10 | CA10X.chr10_ | 173631145 T/C | chr10 | 173,631,145 | C | C | T | T |
| dfreq10 | CA10X.chr10_ | 173631160 G/T | chr10 | 173,631,160 | T | T | G | G |
| dfreq10 | CA10X.chr10_ | 173634952 C/T | chr10 | 173,634,952 | T | T | C | C |
| dfreq10 | CA10X.chr10_ | 173634987 T/C | chr10 | 173,634,987 | C | C | T | T |
| dfreq10 | CA10X.chr10_ | 173645493 C/T | chr10 | 173,645,493 | C | C | T | T |
| dfreq10 | CA10X.chr10_ | 173645529 C/T | chr10 | 173,645,529 | C | C | T | T |
| dfreq10 | CA10X.chr10_ | 173645704 G/A | chr10 | 173,645,704 | G | G | A | A |
| dfreq10 | CA10X.chr10_ | 173651310 A/G | chr10 | 173,651,310 | G | G | A | A |
| dfreq10 | CA10X.chr10_ | 173653215 T/C | chr10 | 173,653,215 | C | C | T | T |
| dfreq10 | CA10X.chr10_ | 173653216 G/A | chr10 | 173,653,216 | G | G | A | A |
| dfreq10 | CA10X.chr10_ | 173653338 A/G | chr10 | 173,653,338 | A | A | G | G |
| dfreq10 | CA10X.chr10_ | 173653495 C/T | chr10 | 173,653,495 | C | C | T | T |
| dfreq10 | CA10X.chr10_ | 173653535 A/G | chr10 | 173,653,535 | G | G | A | A |
| dfreq10 | CA10X.chr10_ | 173654591 A/T | chr10 | 173,654,591 | T | T | A | A |
| dfreq10 | CA10X.chr10_ | 173654915 G/T | chr10 | 173,654,915 | G | G | T | T |
| dfreq10 | CA10X.chr10_ | 173656247 G/C | chr10 | 173,656,247 | C | C | G | G |
| dfreq10 | CA10X.chr10_ | 173656324 T/G | chr10 | 173,656,324 | G | G | T | T |
| dfreq10 | CA10X.chr10_ | 173656410 A/G | chr10 | 173,656,410 | A | A | G | G |
| dfreq10 | CA10X.chr10_ | 173674574 A/G | chr10 | 173,674,574 | A | A | G | G |
| dfreq10 | CA10X.chr10_ | 173695892 C/G | chr10 | 173,695,892 | C | C | G | G |

-continued

| QTL | Marker | alleles | chrom | pos | Garnet | Maor | UCD14 | favorable allele |
|---|---|---|---|---|---|---|---|---|
| dfreq10 | CA10X.chr10_ 173710615 | T/C | chr10 | 173,710,615 | C | C | T | T |
| dfreq10 | CA10X.chr10_ 173750662 | C/T | chr10 | 173,750,662 | C | C | T | T |
| dfreq10 | CA10X.chr10_ 173750705 | T/C | chr10 | 173,750,705 | C | C | T | T |
| dfreq10 | CA10X.chr10_ 173750792 | T/C | chr10 | 173,750,792 | T | T | C | C |
| dfreq10 | CA10X.chr10_ 173750893 | C/T | chr10 | 173,750,893 | T | T | C | C |
| dfreq10 | CA10X.chr10_ 173750917 | G/A | chr10 | 173,750,917 | A | A | G | G |
| dfreq10 | CA10X.chr10_ 173760566 | A/G | chr10 | 173,760,566 | A | A | G | G |
| dfreq10 | CA10X.chr10_ 173760665 | T/G | chr10 | 173,760,665 | T | T | G | G |
| dfreq10 | CA10X.chr10_ 173760688 | A/C | chr10 | 173,760,688 | A | A | C | C |
| dfreq10 | CA10X.chr10_ 173760692 | C/T | chr10 | 173,760,692 | T | T | C | C |
| dfreq10 | CA10X.chr10_ 173807360 | T/C | chr10 | 173,807,360 | T | T | C | C |
| dfreq10 | CA10X.chr10_ 173808234 | G/A | chr10 | 173,808,234 | G | G | A | A |
| dfreq10 | CA10X.chr10_ 173808287 | A/G | chr10 | 173,808,287 | A | A | G | G |
| dfreq10 | CA10X.chr10_ 173808473 | T/C | chr10 | 173,808,473 | T | T | C | C |
| dfreq10 | CA10X.chr10_ 173810341 | A/G | chr10 | 173,810,341 | G | G | A | A |
| dfreq10 | CA10X.chr10_ 173810344 | C/T | chr10 | 173,810,344 | C | C | T | T |
| dfreq10 | CA10X.chr10_ 173843277 | G/C | chr10 | 173,843,277 | G | G | C | C |
| dfreq10 | CA10X.chr10_ 173843292 | T/A | chr10 | 173,843,292 | A | A | T | T |
| dfreq10 | CA10X.chr10_ 173847933 | A/T | chr10 | 173,847,933 | A | A | T | T |
| dfreq10 | CA10X.chr10_ 173861356 | C/T | chr10 | 173,861,356 | T | T | C | C |
| dfreq10 | CA10X.chr10_ 173861358 | G/A | chr10 | 173,861,358 | A | A | G | G |
| dfreq10 | CA10X.chr10_ 173861367 | G/A | chr10 | 173,861,367 | A | A | G | G |
| dfreq10 | CA10X.chr10_ 173861415 | C/T | chr10 | 173,861,415 | T | T | C | C |
| dfreq10 | CA10X.chr10_ 173861444 | C/T | chr10 | 173,861,444 | C | C | T | T |
| dfreq10 | CA10X.chr10_ 173862194 | G/T | chr10 | 173,862,194 | G | G | T | T |
| dfreq10 | CA10X.chr10_ 173862216 | T/C | chr10 | 173,862,216 | T | T | C | C |
| dfreq10 | CA10X.chr10_ 173862325 | A/C | chr10 | 173,862,325 | C | C | A | A |
| dfreq10 | CA10X.chr10_ 173863294 | G/A | chr10 | 173,863,294 | G | G | A | A |
| dfreq10 | CA10X.chr10_ 173863397 | C/T | chr10 | 173,863,397 | C | C | T | T |
| dfreq10 | CA10X.chr10_ 173874442 | T/G | chr10 | 173,874,442 | G | G | T | T |
| dfreq10 | CA10X.chr10_ 173883008 | C/T | chr10 | 173,883,008 | C | C | T | T |
| dfreq10 | CA10X.chr10_ 173883029 | A/G | chr10 | 173,883,029 | A | A | G | G |
| dfreq10 | CA10X.chr10_ 173883160 | A/G | chr10 | 173,883,160 | G | G | A | A |
| dfreq10 | CA10X.chr10_ 173883316 | T/G | chr10 | 173,883,316 | T | T | G | G |
| dfreq10 | CA10X.chr10_ 173883330 | T/C | chr10 | 173,883,330 | T | T | C | C |
| dfreq10 | CA10X.chr10_ 173883344 | T/A | chr10 | 173,883,344 | T | T | A | A |
| dfreq10 | CA10X.chr10_ 173884617 | A/G | chr10 | 173,884,617 | A | A | G | G |
| dfreq10 | CA10X.chr10_ 173884618 | G/A | chr10 | 173,884,618 | A | A | G | G |
| dfreq10 | CA10X.chr10_ 173892556 | T/C | chr10 | 173,892,556 | C | C | T | T |
| dfreq10 | CA10X.chr10_ 173892668 | G/A | chr10 | 173,892,668 | A | A | G | G |
| dfreq10 | CA10X.chr10_ 173897633 | C/T | chr10 | 173,897,633 | C | C | T | T |
| dfreq10 | CA10X.chr10_ 173897634 | A/G | chr10 | 173,897,634 | A | A | G | G |
| dfreq10 | CA10X.chr10_ 173897798 | C/T | chr10 | 173,897,798 | C | C | T | T |
| dfreq10 | CA10X.chr10_ 173897927 | C/A | chr10 | 173,897,927 | A | A | C | C |
| dfreq10 | CA10X.chr10_ 173898267 | T/C | chr10 | 173,898,267 | T | T | C | C |
| dfreq10 | CA10X.chr10_ 173901012 | G/A | chr10 | 173,901,012 | G | G | A | A |
| dfreq10 | CA10X.chr10_ 173901145 | A/G | chr10 | 173,901,145 | A | A | G | G |
| dfreq10 | CA10X.chr10_ 173906389 | C/T | chr10 | 173,906,389 | C | C | T | T |
| dfreq10 | CA10X.chr10_ 173908354 | T/C | chr10 | 173,908,354 | T | T | C | C |
| dfreq10 | CA10X.chr10_ 173908412 | C/T | chr10 | 173,908,412 | C | C | T | T |
| dfreq10 | CA10X.chr10_ 173912958 | C/T | chr10 | 173,912,958 | C | C | T | T |
| dfreq10 | CA10X.chr10_ 173929444 | A/G | chr10 | 173,929,444 | G | G | A | A |
| dfreq10 | CA10X.chr10_ 173937601 | G/C | chr10 | 173,937,601 | G | G | C | C |
| dfreq10 | CA10X.chr10_ 173952471 | A/G | chr10 | 173,952,471 | G | G | A | A |
| dfreq10 | CA10X.chr10_ 173952558 | T/C | chr10 | 173,952,558 | T | T | C | C |
| dfreq10 | CA10X.chr10_ 173954778 | A/G | chr10 | 173,954,778 | G | G | A | A |
| dfreq10 | CA10X.chr10_ 173954791 | G/A | chr10 | 173,954,791 | G | G | A | A |
| dfreq10 | CA10X.chr10_ 173954891 | T/G | chr10 | 173,954,891 | T | T | G | G |
| dfreq10 | CA10X.chr10_ 173956862 | A/G | chr10 | 173,956,862 | G | G | A | A |
| dfreq10 | CA10X.chr10_ 173956887 | G/A | chr10 | 173,956,887 | G | G | A | A |
| dfreq10 | CA10X.chr10_ 173967763 | A/G | chr10 | 173,967,763 | A | A | G | G |
| dfreq10 | CA10X.chr10_ 173971807 | G/A | chr10 | 173,971,807 | A | A | G | G |
| dfreq10 | CA10X.chr10_ 173971821 | A/T | chr10 | 173,971,821 | T | T | A | A |
| dfreq10 | CA10X.chr10_ 173973473 | C/T | chr10 | 173,973,473 | T | T | C | C |
| dfreq10 | CA10X.chr10_ 173994067 | G/A | chr10 | 173,994,067 | A | A | G | G |
| dfreq10 | CA10X.chr10_ 173994344 | A/G | chr10 | 173,994,344 | A | A | G | G |
| dfreq10 | CA10X.chr10_ 173994405 | C/T | chr10 | 173,994,405 | C | C | T | T |
| dfreq10 | CA10X.chr10_ 174002559 | G/A | chr10 | 174,002,559 | A | A | G | G |
| dfreq10 | CA10X.chr10_ 174002561 | G/T | chr10 | 174,002,561 | T | T | G | G |
| dfreq10 | CA10X.chr10_ 174002660 | G/C | chr10 | 174,002,660 | G | G | C | C |
| dfreq10 | CA10X.chr10_ 174002678 | G/T | chr10 | 174,002,678 | T | T | G | G |
| dfreq10 | CA10X.chr10_ 174002713 | A/G | chr10 | 174,002,713 | A | A | G | G |
| dfreq10 | CA10X.chr10_ 174022356 | A/T | chr10 | 174,022,356 | A | A | T | T |
| dfreq10 | CA10X.chr10_ 174051460 | G/A | chr10 | 174,051,460 | G | G | A | A |
| dfreq10 | CA10X.chr10_ 174071242 | T/C | chr10 | 174,071,242 | T | T | C | C |
| dfreq10 | CA10X.chr10_ 174071365 | A/G | chr10 | 174,071,365 | A | A | G | G |

| QTL | Marker | alleles | chrom | pos | Garnet | Maor | UCD14 | favorable allele |
|---|---|---|---|---|---|---|---|---|
| dfreq10 | CA10X.chr10_ | 174071392 C/T | chr10 | 174,071,392 | C | C | T | T |
| dfreq10 | CA10X.chr10_ | 174071443 C/T | chr10 | 174,071,443 | T | T | C | C |
| dfreq10 | CA10X.chr10_ | 174071476 C/T | chr10 | 174,071,476 | C | C | T | T |
| dfreq10 | CA10X.chr10_ | 174074412 C/T | chr10 | 174,074,412 | T | T | C | C |
| dfreq10 | CA10X.chr10_ | 174074416 A/G | chr10 | 174,074,416 | A | A | G | G |
| dfreq10 | CA10X.chr10_ | 174074457 C/T | chr10 | 174,074,457 | C | C | T | T |
| dfreq10 | CA10X.chr10_ | 174074486 C/A | chr10 | 174,074,486 | C | C | A | A |
| dfreq10 | CA10X.chr10_ | 174074534 T/C | chr10 | 174,074,534 | T | T | C | C |
| dfreq10 | CA10X.chr10_ | 174074553 T/G | chr10 | 174,074,553 | T | T | G | G |
| dfreq10 | CA10X.chr10_ | 174107455 G/T | chr10 | 174,107,455 | T | T | G | G |
| dfreq10 | CA10X.chr10_ | 174107502 G/A | chr10 | 174,107,502 | A | A | G | G |
| dfreq10 | CA10X.chr10_ | 174107529 G/A | chr10 | 174,107,529 | G | G | A | A |
| dfreq10 | CA10X.chr10_ | 174107530 C/T | chr10 | 174,107,530 | T | T | C | C |
| dfreq10 | CA10X.chr10_ | 174107556 T/C | chr10 | 174,107,556 | T | T | C | C |
| dfreq10 | CA10X.chr10_ | 174107571 A/G | chr10 | 174,107,571 | A | A | G | G |
| dfreq10 | CA10X.chr10_ | 174111055 A/G | chr10 | 174,111,055 | A | A | G | G |
| dfreq10 | CA10X.chr10_ | 174111451 C/T | chr10 | 174,111,451 | T | T | C | C |
| dfreq10 | CA10X.chr10_ | 174111511 A/C | chr10 | 174,111,511 | C | C | A | A |
| dfreq10 | CA10X.chr10_ | 174111550 G/A | chr10 | 174,111,550 | G | G | A | A |
| dfreq10 | CA10X.chr10_ | 174111568 G/A | chr10 | 174,111,568 | G | G | A | A |
| dfreq10 | CA10X.chr10_ | 174123278 A/C | chr10 | 174,123,278 | A | A | C | C |
| dfreq10 | CA10X.chr10_ | 174123319 T/C | chr10 | 174,123,319 | T | T | C | C |
| dfreq10 | CA10X.chr10_ | 174873248 A/G | chr10 | 174,873,248 | G | G | A | A |
| dfreq10 | CA10X.chr10_ | 174986954 C/T | chr10 | 174,986,954 | T | T | C | C |
| dfreq10 | CA10X.chr10_ | 174987185 A/G | chr10 | 174,987,185 | A | A | G | G |
| dfreq10 | CA10X.chr10_ | 174987202 T/G | chr10 | 174,987,202 | G | G | T | T |
| dfreq10 | CA10X.chr10_ | 176405366 T/C | chr10 | 176,405,366 | T | T | C | C |
| dfreq10 | CA10X.chr10_ | 176407620 C/T | chr10 | 176,407,620 | T | T | C | C |
| dfreq10 | CA10X.chr10_ | 176436785 A/G | chr10 | 176,436,785 | A | A | G | G |
| dfreq10 | CA10X.chr10_ | 176436812 C/T | chr10 | 176,436,812 | T | T | C | C |
| dfreq10 | CA10X.chr10_ | 176436844 A/C | chr10 | 176,436,844 | A | A | C | C |
| dfreq10 | CA10X.chr10_ | 176437011 G/T | chr10 | 176,437,011 | G | G | T | T |
| dfreq10 | CA10X.chr10_ | 176437023 T/G | chr10 | 176,437,023 | G | G | T | T |
| dfreq10 | CA10X.chr10_ | 176437108 C/T | chr10 | 176,437,108 | C | C | T | T |
| dfreq10 | CA10X.chr10_ | 176437176 G/A | chr10 | 176,437,176 | G | G | A | A |
| dfreq10 | CA10X.chr10_ | 176437177 T/C | chr10 | 176,437,177 | T | T | C | C |
| dfreq10 | CA10X.chr10_ | 176437178 G/A | chr10 | 176,437,178 | G | G | A | A |
| dfreq10 | CA10X.chr10_ | 176437276 C/T | chr10 | 176,437,276 | T | T | C | C |
| dfreq10 | CA10X.chr10_ | 176437419 T/C | chr10 | 176,437,419 | T | T | C | C |
| dfreq10 | CA10X.chr10_ | 176815719 C/T | chr10 | 176,815,719 | T | T | C | C, | wherein the positions are as indicated in Pepper Genome UCD10X v1.0.

2. A method of harvesting peppers, the method comprising removing pepper fruit from one or more cultivated pepper of claim 1.

3. The method of claim 2, wherein the peppers are removed by shaking the pepper plant.

* * * * *